US010258690B2

(12) United States Patent
Babic et al.

(10) Patent No.: US 10,258,690 B2
(45) Date of Patent: Apr. 16, 2019

(54) 5-ALA DERIVATIVES AND USE THEREOF

(71) Applicant: UNIVERSITE DE GENEVE, Geneva (CH)

(72) Inventors: Andrej Babic, Veigy-Foncenex (FR); Norbert Lange, Nyon (CH)

(73) Assignee: UNIVERSITE DE GENEVE, Geneva (CH)

( * ) Notice: Subject to any disclaimer, the term of this patent is extended or adjusted under 35 U.S.C. 154(b) by 0 days.

(21) Appl. No.: 15/575,025

(22) PCT Filed: May 17, 2016

(86) PCT No.: PCT/IB2016/052840
§ 371 (c)(1),
(2) Date: Nov. 17, 2017

(87) PCT Pub. No.: WO2016/185368
PCT Pub. Date: Nov. 24, 2016

(65) Prior Publication Data
US 2018/0133320 A1    May 17, 2018

(30) Foreign Application Priority Data

May 19, 2015   (EP) .................................. 15168276

(51) Int. Cl.
| | |
|---|---|
| *A61K 41/00* | (2006.01) |
| *A61P 17/06* | (2006.01) |
| *A61P 31/00* | (2006.01) |
| *A61P 31/12* | (2006.01) |
| *A61P 17/00* | (2006.01) |
| *A61P 19/02* | (2006.01) |
| *A61P 31/04* | (2006.01) |
| *A61P 1/00* | (2006.01) |
| *A61P 35/00* | (2006.01) |
| *A61N 5/06* | (2006.01) |
| *C07F 9/09* | (2006.01) |
| *C07F 9/24* | (2006.01) |
| *C07H 13/12* | (2006.01) |

(52) U.S. Cl.
CPC .......... *A61K 41/0061* (2013.01); *A61N 5/062* (2013.01); *A61P 1/00* (2018.01); *A61P 17/00* (2018.01); *A61P 17/06* (2018.01); *A61P 19/02* (2018.01); *A61P 31/00* (2018.01); *A61P 31/04* (2018.01); *A61P 31/12* (2018.01); *A61P 35/00* (2018.01); *C07F 9/091* (2013.01); *C07F 9/2458* (2013.01); *C07H 13/12* (2013.01); *A61N 2005/0663* (2013.01)

(58) Field of Classification Search
CPC ................................................ A61K 41/0061
See application file for complete search history.

(56) References Cited

U.S. PATENT DOCUMENTS

2014/0010761 A1    1/2014    Parent et al.

FOREIGN PATENT DOCUMENTS

| WO | WO 96/28412 | 9/1996 |
|---|---|---|
| WO | WO 02/10120 | 2/2002 |
| WO | WO 2005/092838 | 10/2005 |

OTHER PUBLICATIONS

Babič, A. et al. "Tunable phosphatase-sensitive stable prodrugs of 5-aminolevulinic acid for tumor fluorescence photodetection" *Journal of Controlled Release*, 2016, pp. 155-164, vol. 235.
Berger, Y. et al. "Evaluation of Dipeptide-Derivatives of 5-Aminolevulinic Acid as Precursors for Photosensitizers in Photodynamic Therapy" *Bioorganic & Medicinal Chemistry*, 2003, pp. 1343-1351, vol. 11.
Blencowe, C. A. et al. "Self-immolative linkers in polymeric delivery systems" *Polymer Chemistry*, 2011, pp. 773-790, vol. 2.
Casas, A. et al. "ALA and ALA hexyl ester in free and liposomal formulations for the photosensitisation of tumour organ cultures" *British Journal of Cancer*, 2002, pp. 837-842, vol. 86, No. 5.
Chitambar, C. R. "Medical Applications and Toxicities of Gallium Compounds" *International Journal of Environmental Research and Public Health*, 2010, pp. 2337-2361, vol. 7.
Collery, P. et al. "Gallium in cancer treatment" *Critical Reviews in Oncology/Hematology*, 2002, pp. 283-296, vol. 42.
Di Venosa, G. et al. "Distribution of 5-aminolevulinic acid derivatives and induced porphyrin kinetics in mice tissues" *Cancer Chemotherapy and Pharmacology*, 2006, pp. 478-486, vol. 58.
Fotinos, N. et al. "5-Aminolevulinic Acid Derivatives in Photomedicine: Characteristics, Application and Perspectives" *Photochemistry and Photobiology*, 2006, pp. 994-1015, vol. 82.
Giuntini, F. et al. "Improved Peptide Prodrugs of 5-ALA for PDT: Rationalization of Cellular Accumulation and Protoporphyrin IX Production by Direct Determination of Cellular Prodrug Uptake and Prodrug Metabolization" *Journal of Medicinal Chemistry*, 2009, pp. 4026-4037, vol. 52, No. 13.
Herceg, V. et al. "Activity of phosphatase-sensitive 5-aminolevulinic acid prodrugs in cancer cell lines" *Journal of Photochemistry & Photobiology, B: Biology*, 2017, pp. 34-42, vol. 171.
Ignatius, A. A. et al. "In vitro biocompatibility of bioresorbable polymers: poly(L, DL-lactide) and poly(L-lactide-co-glycolide)" *Biomaterials*, 1996, pp. 831-839, vol. 17, No. 8.
Kloek, J. et al. "Prodrugs of 5-Aminolevulinic Acid for Photodynamic Therapy" *Photochemistry and Photobiology*, 1996, pp. 994-1000, vol. 64, No. 6.
Larsen, P. F. et al. "Intraspecific variation in expression of candidate genes for osmoregulation, heme biosynthesis and stress resistance suggests local adaptation in European flounder (*Platichthys flesus*)" *Heredity*, 2008, pp. 247-259, vol. 101.

(Continued)

*Primary Examiner* — Golam M Shameem
(74) *Attorney, Agent, or Firm* — Saliwanchik, Lloyd & Eisenschenk

(57) ABSTRACT

The present invention is directed to new 5-ALA derivatives, particles and formulation thereof, related methods of preparation and methods of use thereof. In particular, the invention relates to compounds of the invention, particles and formulation thereof useful in the treatment of a cancer and/or the diagnosis of a cancer cell such as in photodynamic therapy or photodynamic diagnosis.

17 Claims, 4 Drawing Sheets

(56) References Cited

OTHER PUBLICATIONS

Perotti, C. et al. "ALA and ALA hexyl ester induction of porphyrins after their systemic administration to tumour bearing mice" *British Journal of Cancer*, 2002, pp. 790-795, vol. 87, No. 7.
Vallinayagam, R. etal. "Synthesis of Novel and Stable 5-Aminolevulinic Acid Derivatives for the Efficient Synthesis of 5-Aminolevulinic Acid Based Prodrugs" *Synthesis*, 2007, pp. 3731-3735, No. 23.
Van Den Bergh, H. "Light and porphyrins in cancer therapy" *Chemistry in Britain*, May 1986, pp. 430-439, vol. 22, No. 5.
Williams, D. F. "On the mechanisms of biocompatibility" *Biomaterials*, 2008, pp. 2941-2953, vol. 29.
Written Opinion in International Application No. PCT/IB2016/052840, dated Aug. 1, 2016, pp. 1-7.
Babič, A. et al. "5-Aminolevulinic Acid-Squalene Nanoassemblies for Tumor Photodetection and Therapy: In Vitro Studies" *Nanoscale Research Letters*, 2018, pp. 1-9, vol. 13, No. 10.
Herceg, V. et al. "Design, synthesis and in vitro evaluation of β-glucuronidase-sensitive prodrug of 5-aminolevulinic acid for photodiagnosis of breast cancer cells" *Bioorganic Chemistry*, 2018, pp. 372-380, vol. 78.

A

B

5-ALA DERIVATIVES AND USE THEREOF

CROSS-REFERENCE TO RELATED APPLICATION

This application is the U.S. national stage application of International Patent Application No. PCT/IB2016/052840, filed May 17, 2016.

FIELD OF THE INVENTION

The present invention is directed to 5-Aminolevulinic acid (5-ALA) mediated photodynamic therapy (PDT) and fluorescence photodetection (FD) of neoplastic diseases.

BACKGROUND OF THE INVENTION

Photochemotherapy or photodynamic therapy is a technique based on the discovery that cancer cells treated with certain chemicals will die when exposed to light. This technique consists in the administering of a tumor-localizing photosensitizer (photochemotherapeutic) followed by the irradiation of the targeted tumor site with photoactivating light of a suitable wavelength, in order to activate the photosensitizing agent that in turn converts oxygen into cytotoxic forms, whereby the affected cells are killed or their proliferative potential diminished.

5-ALA is known to specifically induce the in-situ formation of high amounts of photoactive porphyrins in neoplastic and (non-) neoplastic cells with high cellular turnover. Beside the use of 5-ALA for treatment by PDT the use of its ability to induce preferential accumulation of photoactive porphyrins in neoplasia was suggested for improving detection of neoplastic lesions in order to guide biopsies, improve surgery, or allow for appropriate patient's management. However, the clinical development of 5-ALA-mediated phototherapy and fluorescence photodetection (FD) of neoplastic diseases, which are those of the most selective cancer treatment techniques, have been hampered by the limited local bioavailability of 5-ALA. In fact, the short plasma half-life of 5-ALA and its low bioavailability largely hinders its application for neoplastic lesions that are not accessible by topical administration.

The development of 5-ALA derivatives and especially 5-ALA esters (WO 96/28412, WO 02/10120, Fotinos et al., 2006, *Photochemistry and Photobiology*, 82: 994-1015) such as methylaminolevulinate (MAL) and hexylaminolevulinate (HAL), led to market approval of those for the treatment of actinic keratinosis and difficult-to-treat basal cell carcinoma (Metvix®; Galderma, Switzerland) and for improving detection of superficial bladder cancer (Hexvix®; Photocure ASA, Oslo, Norway), respectively. Acid addition salts of 5-ALA and 5-ALA derivatives (WO 2005/092838) have been further developed for improving their physico-chemical properties such as for increasing their stability (e.g. lower hygroscopicity), notably for topical formulations (e.g. creams) as compared to the corresponding hydrochloride salts.

However, the use of 5-ALA esters remains restricted to organs that are accessible by topical administration as they have been shown to be unstable in the gastrointestinal tract when given orally or in the blood plasma. Their systemic use has shown to induce acute toxicity after bolus injections in numerous in vivo models (Perotti et al., 2002, *British Journal of Cancer*, 87: 790-795; Di Venosa et al., 2006, *Cancer Chemotherapy and Pharmacology*, 58, 478-486 or Fotinos et al., 2006, *Photochemistry Photobiology*, 82: 994-1015). Furthermore, the systemic use of 5-ALA esters induces the formation of porphyrins in a much less effective way than 5-ALA. Finally, those compounds have been shown to be poorly stable overtime.

Therefore, important life-threatening diseases including brain cancer, prostate cancer, mama carcinoma, breast cancer, ovarian cancer, lung cancer, and lymphoma can hardly be detected/treated by 5-ALA-mediated phototherapy technology. Thus, there is a big need for alternative photochemotherapeutic agents or agents for fluorescence photodetection via parenteral routes, namely oral, intravenous, intraperitoneal, intramuscular, or subcutaneous.

SUMMARY OF THE INVENTION

The invention relates to the unexpected finding of specific 5-ALA derivatives according to the invention which are particularly suitable for injection route, presenting unexpected stability over months and which, for some derivatives, can form nanoparticles which lead to the in vivo release of 5-ALA through a mechanism of activation by enzymes ubiquitously expressed in mammalian cells. The invention is further related to the unexpected finding of formulations of 5-ALA derivatives according to the invention comprising nanoparticle-forming 5-ALA derivatives according to the invention presenting a controlled release of 5-ALA once systemically administered, an increased bioavailability and increased plasma half-life together with a reduced toxicity as compared to formulations comprising known 5-ALA esters. According to a particular aspect, the compounds of the invention provide stable and non-toxic prodrugs of 5-ALA which lead to the release of 5-ALA with controllable release profiles and reduced systemic toxicity. The invention further relates to 5-ALA derivatives, formulations thereof, related methods of preparation and methods of use thereof, those derivatives presenting a substantially increased ability in inducing the formation of photoactive porphyrins in cancer cells as compared to their corresponding esters. In particular, the methods, uses, formulations and compositions according to the invention are useful in patients in the diagnosis of cancer cells and/or treatment of a cancer or other pathologies.

As a consequence, formulations according to the invention advantageously present an increased therapeutic index as compared to known agents useful for photochemotherapy and fluorescence photodetection of neoplastic diseases.

One aspect of the invention provides new 5-ALA derivatives and pharmaceutically acceptable salts thereof.

Second aspect of the invention provides new 5-ALA derivatives according to the invention for use as a medicament.

Another aspect of the invention provides a pharmaceutical formulation comprising at least one 5-ALA derivative according to the invention and at least one pharmaceutically acceptable carrier.

Another aspect of the invention provides a particle formed by at least one 5-ALA derivative according to the invention.

Another aspect of the invention provides a kit comprising in one or more container(s) a formulation or a particle according to the invention together with instruction of use of said formulation.

Another aspect of the invention provides a formulation or a particle according the invention for use as a medicament.

Another aspect of the invention provides a compound, a particle or a formulation according the invention for the treatment or repression of a disease or disorder including any malignant, pre-malignant and non-malignant abnormalities responsive to photochemotherapy, including, but not limited to, tumors or other hyperproliferative conditions such as cancers, skin disorders such as psoriasis, skin cancer, or actinic keratosis, infectious diseases (e.g. viral, bacterial, fungal infections), inflammatory diseases like Morbus Crohn, arthritis and rheumatoid arthritis, Barrett's esophagus or arterial restenosis.

Another aspect of the invention provides a compound, a particle or a formulation according the invention for the treatment or repression of a cancer or for the detection of a cancer cell. Another aspect of the invention provides a use of a compound, a particle or a formulation of the invention for the preparation of a pharmaceutical composition for the treatment or repression of a disease or disorder including any malignant, pre-malignant and non-malignant abnormalities responsive to photochemotherapy, including, but not limited to, tumors or other hyperproliferative conditions such as cancers, skin disorders such as psoriasis, skin cancer, or actinic keratosis, infectious diseases (e.g. viral, bacterial, fungal infections), inflammatory diseases like Morbus Crohn, arthritis and rheumatoid arthritis, Barrett's esophagus or arterial restenosis.

Another aspect of the invention provides a use of a compound, a particle or a formulation according to the invention for the preparation of a pharmaceutical composition for the treatment or repression of a cancer or for detection of a cancer cell.

Another aspect of the invention provides a process for the preparation of a compound according to the invention.

Another aspect of the invention provides intermediate compounds for the preparation of compounds of the invention.

Another aspect of the invention provides a process for the preparation of a particle according to the invention.

Another aspect of the invention provides a method of treating or repressing a disease or disorder including any malignant, pre-malignant and non-malignant abnormalities responsive to photochemotherapy, including, but not limited to, tumors or other hyperproliferative conditions such as cancers, skin disorders such as psoriasis, skin cancer, or actinic keratosis, infectious diseases (e.g. viral, bacterial, fungal infections), inflammatory diseases like Morbus Crohn, arthritis and rheumatoid arthritis, Barrett's esophagus or arterial restenosis, said method comprising administering in a subject in need thereof a therapeutically effective amount of a compound, a particle or a pharmaceutical formulation according to the invention and exposing malignant, pre-malignant or non-malignant abnormal cells to light.

Another aspect of the invention provides a method of treating or repressing a cancer, said method comprising administering in a subject in need thereof a therapeutically effective amount of a compound, a particle or a pharmaceutical formulation according to the invention and exposing cancer cells to light.

Another aspect of the invention provides a method of diagnosis of a cancer cell, said method comprising the following steps:
  a) administering to a subject in need thereof a detectably effective amount of a compound, a particle or a pharmaceutical formulation according to the invention;
  b) exposing the site of investigation of the subject's body to light.

Another aspect of the invention provides a method of treating or repressing a cancer, said method comprising administering in a subject in need thereof a therapeutically effective amount of a compound, a particle or a pharmaceutical formulation according to the invention in combination with a metal ion or a radioisotope thereof.

Another aspect of the invention provides a method of diagnosis of a cancer cell, said method comprising the following steps:
  a) administering in a subject in need thereof a detectably effective amount of a compound, a particle or a pharmaceutical formulation according to the invention;
  b) administering in a subject in need thereof a radioisotope of a metal ion;
  c) detecting the distribution of the radioisotope within said subject;
wherein administrations under steps a) and b) may be carried out simultaneously or sequentially.

DETAILED DESCRIPTION OF THE INVENTION

Figure 1:
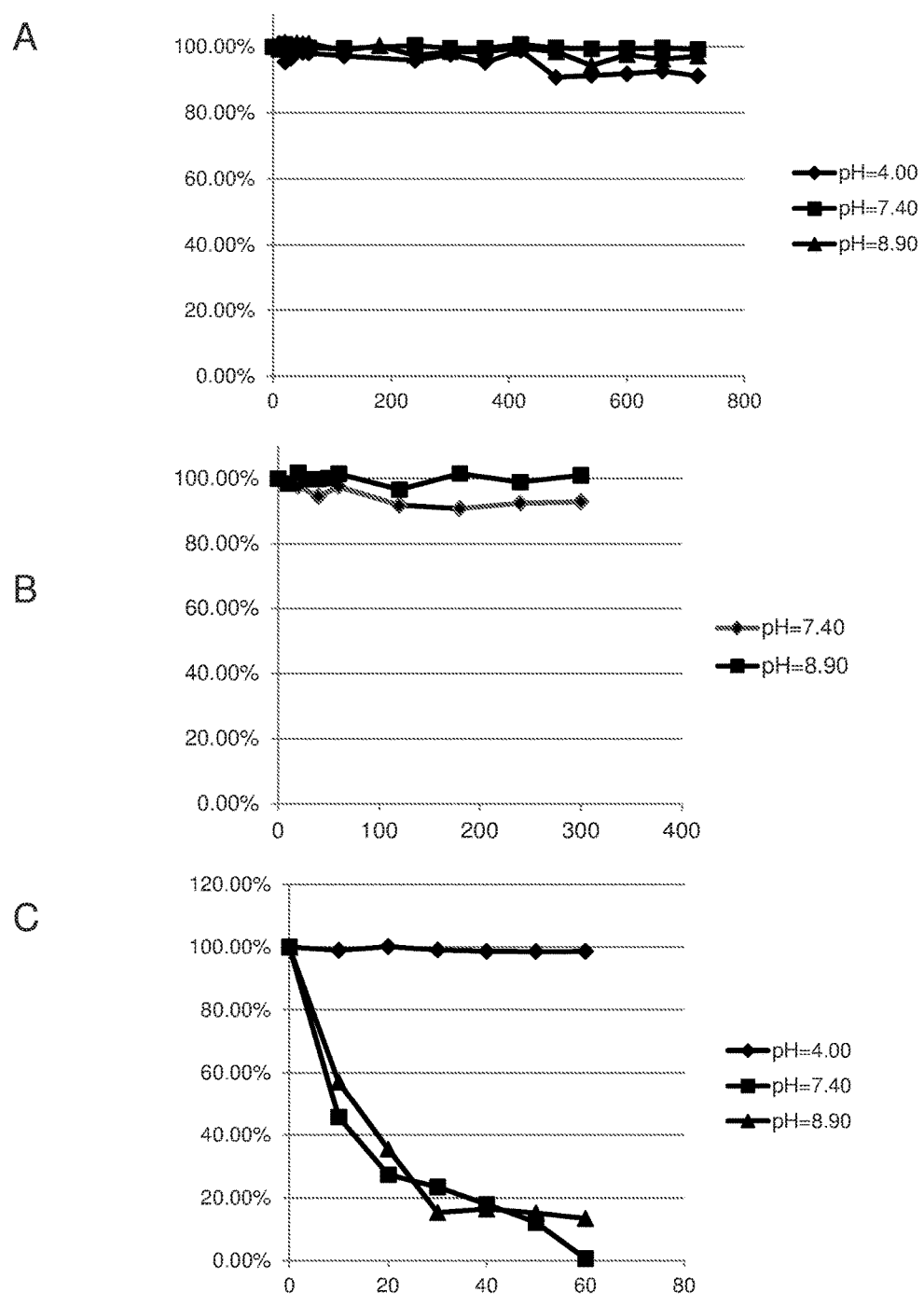
FIG. 1 represents the chemical stability of compounds of the invention versus the ester 5-ALA-hexyl ester (ALA-hex) (C) at 5 mM at 37° C. as described in Example 8 as measured by % of compound remaining in solution versus time (in min) at various pH. A: compound 1; B: compound 7.

The term "non-peptidic moiety cleavable by ubiquitous enzymes present in mammalian cells" comprises non-peptidic moiety that are cleavable by enzymes including phosphatases (e.g. alkaline phosphatases, acid phosphatases), phosphoamidases, nitroreductases, azoreductases, glycosidases (e.g. mono-, di-, tri-, poly-saccharides glycosidases), glucuronisidases and those as described in Rautio et al., 2010, *Prodrugs and targeted delivery; towards better ADME properties*; Wiley with the proviso that the non-peptidic moiety cleavable by ubiquitous enzymes present in mammalian cells is not an acetyl group. Those groups are well known to the person skilled in the art (Casas et al., 2002, *Curr Med Chem Anticancer Agents*, 2(4):465-75; Giuntini, 2009, *J. Med. Chem.*, 9, 52(13):4026-37; Berger et al., 2003, *Bioorg. Med. Chem.*, 3, 11(7):1343-51). Those groups includes one or more phosphate groups, phosphoamide groups, β-D-glucuronic acid groups, α-glycosyl groups, carbohydrates, mono-, di-, tri-saccharides groups, diazo groups, nitro groups and the like The term "self-removable" linker includes any moiety that is spontaneously self-removable upon cleavage of the group B from the compound of the invention. Examples of reaction mechanism of self-removal of the linkers of the invention are provided herein.

The term "biocompatible", refers to an agent that does not induce an adverse response when inserted or injected into a living subject, for example, without inducing significant inflammation and/or acute rejection of the agent by the immune system, for instance, via a T-cell response. As opposed, a non-biocompatible material implanted/administered into a subject provokes an immune response in the subject that can be severe enough such that the rejection of the material by the immune system cannot be adequately controlled, and often is of a degree such that the material must be removed from the subject. Biocompatibility can be determined for example by exposing an agent to cells in vitro where biocompatible agents are agents that typically will not result in significant cell death at moderate concentrations. Biocompatibility may be assayed as described in Williams, 2008, *Biomaterials*, 29: 2941-2953 or Ignatius et al., 1996, *Biomaterials*, 17: 831-9, for example. The term "biodegradable" as applied to particles of the invention means compounds of the invention, i.e. compounds which are degradable within a physiological environment, such as within the body, either enzymatically or non-enzymatically to produce biocompatible or non-toxic by-products which can be further metabolized or excreted via normal physiological pathways.

The term "5-ALA ester" includes esters of 5-Aminolevulinic acid such as those described in WO 96/28412, WO 02/10120 or Fotinos et al., 2006, above and derivatives thereof. Exemplary 5-ALA esters include hexyl aminolevulinate and methyl aminolevulinate.

The term "5-ALA ester derivative" refers to any derivative of a 5-ALA ester, which is capable of providing directly or indirectly, the activity disclosed herein.

The term "cancer" includes metastatic and non-metastatic cancers such as colon cancer, rectal cancer, breast cancer, mama carcinoma, lymphoma, brain cancer, ovarian cancer, non-small cell lung cancer, colorectal carcinoma, glioblastoma, gastric, bronchus cancer, pancreatic cancer, urinary bladder cancer, hepatic cancer, non-melanoma skin cancer, oesophageal cancer, oral cancer, duodenal cancer, cervix cancer, uterus cancer, kidney cancer and prostate cancer. "Cancer cells" can occur in form of tumor tissue, be present as isolated cells in a subject (e.g., leukemia cells), or be cell lines derived from a cancer.

As used herein, "treatment" and "treating" and the like generally mean obtaining a desired pharmacological and physiological effect. The term "treatment" as used herein covers any treatment of a disease in a mammal, particularly a human, and includes inhibiting the disease, i.e., arresting its development; or relieving the disease, i.e. causing regression of the disease and/or its symptoms or conditions such as tumor growth arrest or tumor regression. Diseases or disorders, which may be treated or diagnosed according to the present invention include any malignant, pre-malignant and non-malignant abnormalities responsive to photochemotherapy.

The term "subject" as used herein refers to mammals. For examples, mammals contemplated by the present invention include human, primates, domesticated animals such as cattle, sheep, pigs, horses, laboratory rodents and the like.

The term "effective amount" as used herein refers to an amount of at least one particle or a pharmaceutical formulation thereof according to the invention that elicits the biological or medicinal response in a tissue, system, animal, or human that is being sought. In one embodiment, the effective amount is a "therapeutically effective amount" for the alleviation of the symptoms of the disease or condition being treated. Typically, an effective amount can be used to inhibit the growth of cancer cells, e.g., prostate cancer cells, i.e. any slowing of the rate of cancer cell proliferation and/or migration, arrest of cancer cell proliferation and/or migration, or killing of cancer cells, such that the rate of cancer cell growth is reduced in comparison with the observed or predicted rate of growth of an untreated control cancer cell. The term "inhibits growth" can also refer to a reduction in size or disappearance of a cancer cell or tumor, as well as to a reduction in its metastatic potential. Preferably, such an inhibition at the cellular level may reduce the size, deter the growth, reduce the aggressiveness, or prevent or inhibit metastasis of a cancer in a patient. Those skilled in the art can readily determine, by any of a variety of suitable indicia, whether cancer cell growth is inhibited.

The term "efficacy" of a treatment according to the invention can be measured based on changes in the course of a disease in response to a use or a method according to the invention. The efficacy of a treatment of a cancer according to the invention can be measured by a reduction of tumor volume, and/or an increase of progression free survival time and/or increased health and well-being of the subject (e.g. repressing a cancer). Inhibition of cancer cell growth may be evidenced, for example, by arrest of cancer cells in a particular phase of the cell cycle, e.g., arrest at the G2/M phase of the cell cycle. Inhibition of cancer cell growth can also be evidenced using well known imaging methods such as magnetic resonance imaging, computerized axial tomography, PET, SPECT, photoacoustic imaging, X-rays and fluorescence imaging/detection. Cancer cell growth can also be determined indirectly, for example by determining the levels of circulating carcinoembryonic antigen, prostate specific antigen or other cancer-specific antigens that are correlated with cancer cell growth.

The term "detectably effective amount" as used herein refers to an amount of at least one particle or a pharmaceutical formulation thereof according to the invention that elicits a detectable fluorescence emission response in a cancer cell from a tissue, system, animal, or human that is being investigated. In one embodiment, the "detectably effective amount" is an amount necessary for the detection of a fluorescence emission signal between about 600 and about 750 nm in a cancer cell from a tissue, system, animal or human that is being investigated induced by the exposure of said tissue, system, animal or human to an excitation signal at about 300 and about 700 nm.

The term "radioisotope of a metal ion" includes a radioisotope of a metal ion useful in imaging and/or therapy, notably in cancer imaging and/or therapy such as radioisotopes of $Mg^{2+}$, $Fe^{2+}$, $Ca^{2+}$, $Gd^{3+}$, $Ga^{3+}$, and $Zn^{2+}$ (for example $Ga^{67}$, $Ga^{68}$ $Zn^{65}$, $Fe^{59}$). Detection techniques useful in metal ion imaging include MRI (Magnetic Resonance Imaging), SPECT (Single-photon emission computed tomography), and X-ray imaging techniques as described in *Textbook of in vivo Imaging in Vertebrates* Edited by Vasilis Ntziachristos, Anne Leroy-Willig and Bertrand Tavitian ISBN: 978-0-470-01528-5. Metal ions according to the invention and isotopes thereof include metal ion salts such as citrate, nitrate, chloride, maltolate, bromide, sulfate, or phosphate salts.

The term "particle" according to the invention means particles which are solid, semi-solid or liquid and which are formed in aqueous solution, i.e. particles that are formed by compounds of the invention and are not soluble in aqueous solution. For example, solid particles according to the invention may be characterized by scanning electron microscopy, transmission electron microscopy, imaging or light scattering, sedimentation velocity. According to a particular aspect, particles of the invention have a diameter comprised from about 10 nm and about 800 nm.

The term "self-removable linker" according to the invention refers to a "self-immolative linker" which means a linker which forms a stable bond between protecting and leaving groups, which becomes labile upon activation, leading to the rapid disassembly of the parent molecule. Examples of self-removable linker are described in Self-immolative linkers in polymeric delivery systems Blencowe at al., 2011, *Polym. Chem.*, 2, 773-790.

The term "$C_1$-$C_{30}$ alkyl" when used alone or in combination with other terms, comprises monovalent straight chain or branched alkyl groups having 1 to 30 carbon atoms. This term is exemplified by groups such as methyl, ethyl, n-butyl, sec-butyl, iso-butyl, propyl, tert-butyl, t-butyl, n-pentyl, 1-ethylpropyl, 2-methylbutyl, 3-methylbutyl, 2,2-dimethylpropyl, n-hexyl, 2-methylpentyl, 3-methylpentyl, 4-methylpentyl, n-heptyl, 2-methylhexyl, 3-methylhexyl, 4-methylhexyl, 5-methylhexyl, n-octyl, n-nonyl, n-decanyl and the like. Particularly, those include $C_1$-$C_8$ alkyl, in particular $C_1$-$C_6$ alkyl, which, by analogy, refer respectively to monovalent straight chain or branched alkyl groups having 1 to 8 and 1 to 6, respectively carbon atoms.

The term "$C_2$-$C_{30}$ alkenyl" when used alone or in combination with other terms, comprises a straight or branched alkenyl chains with a carbon number of 2-30 having any available number of double bonds in any available positions, and the configuration of the double bond may be the (E) or (Z) configuration. This term is exemplified by groups such as vinyl, allyl, isopropenyl, 1-propenyl and the like.

The term "$C_2$-$C_{30}$ alkynyl" when used alone or in combination with other terms, comprises a straight or branched alkynyl chains with a carbon number of 2-30 having any available number of triple bonds in any available positions. This term is exemplified by groups such as ethynyl (—C≡CH), 1-propynyl, 2-propynyl (propargyl: —CH$_2$C≡CH), 2-butynyl, 2-pentene-4-ynyl, and the like.

The term "aryl" refers to an unsaturated aromatic carbocyclic group of from 6 to 30 carbon atoms having a single ring (e.g., phenyl) or multiple condensed rings (e.g., indenyl, naphthyl). In a particular embodiment, aryl refers to aromatic carbocyclic group of from 6 to 12 carbons, typically 6 to 10 carbons. Aryl include phenyl, naphthyl, anthryl, phenanthrenyl and the like.

The term "heteroaryl" refers to a monocyclic heteroaromatic, or a bicyclic or a tricyclic fused-ring heteroaromatic group. Particular examples of heteroaromatic groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxa-zolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

The term "C3-C8-cycloalkyl" refers to a saturated carbocyclic group of from 3 to 8 carbon atoms having a single ring (e.g., cyclohexyl) or multiple condensed rings (e.g., norbornyl). C3-C8-cycloalkyl includes cyclopentyl, cyclohexyl, norbornyl and the like.

The term "heterocycloalkyl" refers to a C3-C8-cycloalkyl group according to the definition above, in which up to 3 carbon atoms are replaced by heteroatoms chosen from the group consisting of O, S, NR, R being defined as hydrogen or methyl. Heterocycloalkyl include pyrrolidinyl, piperidinyl, piperazinyl, morpholinyl, tetrahydrofuranyl and the like. The term "alkoxy" refers to the group —O—R where R includes "$C_1$-$C_6$ alkyl", "aryl", "heteroaryl", "aryl $C_1$-$C_6$ alkyl" or "heteroaryl $C_1$-$C_6$ alkyl". Preferred alkoxy groups include for example, methoxy, ethoxy, phenoxy and the like.

The term "aryl C1-C6 alkyl" refers to C1-C6 alkyl groups having an aryl substituent, including 3-phenylpropanyl, benzyl and the like.

The term "$C_1$-$C_6$ alkyl aryl" refers to aryl groups having a $C_1$-$C_6$ alkyl substituent, including methyl phenyl, ethyl phenyl and the like.

Unless otherwise constrained by the definition of the individual substituent, all the above substituents should be understood as being all optionally substituted.

Unless otherwise constrained by the definition of the individual substituent, the term "substituted" refers to groups substituted with from 1 to 5 substituents selected from the group consisting of "C1-C6 alkyl," "C2-C6 alkenyl," "C2-C6 alkynyl," "C3-C8-cycloalkyl," "heterocycloalkyl," "C1-C6 alkyl aryl," "C1-C6 alkyl heteroaryl," "C1-C6 alkyl cycloalkyl," "C1-C6 alkyl heterocycloalkyl," "cycloalkyl C1-C6 alkyl," "heterocycloalkyl C1-C6 alkyl," "amino," "amido," "aminosulfonyl," "ammonium," "alkoxy," "acyl amino," "amino carbonyl," "azido", "diaza", "aryl," "aryl C1-C6 alkyl," "C1-C6 alkyl aryl," "heteroaryl," "heteroaryl C1-C6 alkyl," "C1-C6 alkyl heteroaryl," "sulfinyl," "sulfonyl," "sulphonamide", "alkoxy," "alkoxy carbonyl," "carbamate," "sulfanyl," "halogen," "carboxy," trihalomethyl, cyano, hydroxy, mercapto, nitro, ether, ester, reverse ester, carboxylic acid, carboxylic ester, carbonate, acetal, hemiacetal, ketal, thiol, thioether, N-oxide, disulfide, sulfone, sulfonate, sulfoxide, sulfonamide, imine, carbamide, aziridine, nitro, ketoxime, aldoxime, nitroso, hydroxylamine, phosphodiester, phosphonate, and phosphate, and the like. The term "halogen" refers to fluoro, chloro, bromo and iodo atoms.

The term "lipidic group" includes alcohols or amino derivatives of unbranched or branched, saturated or (poly) unsaturated $C_{12}$ to $C_{30}$ lipids such as squalenol, squalanol, squalene amine, farnesol, geraniol, myristyl alcohol, phytol, stearyl alcohol, palmityl alcohol, arachidyl alocohol and the like.

The term "pharmaceutical formulation" refers to preparations which are in such a form as to permit biological activity of the active ingredient(s) to be unequivocally effective and which contain no additional component which would be toxic to subjects to which the said formulation would be administered.

According to one aspect, the invention provides a 5-Aminolevulinic derivative of Formula (I) and any pharmaceutically acceptable salts thereof:

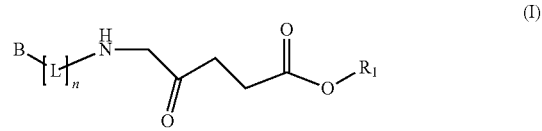

wherein B is a biocompatible non-peptidic moiety cleavable by ubiquitous or specific enzymes present in mammalian cells, L is a biocompatible self-removable linker and $R^1$ is selected from H, optionally substituted C1-C30 alkyl (such as C1-C6 alkyl, like hexyl or methyl), optionally substituted $C_2$-$C_{30}$ alkenyl (e.g. $C_2$-$C_6$ alkenyl), optionally substituted $C_2$-$C_{30}$ alkynyl (e.g. $C_2$-$C_6$ alkynyl), optionally substituted alkoxy, optionally substituted aryl and optionally substituted aryl C1-C6 alkyl (e.g. such as benzyl) and n is an integer selected from 0 and 1.

According to a particular embodiment, B is a biocompatible non-peptidic moiety cleavable by phosphatases or glycosidases.

According to a particular embodiment, is provided a 5-Aminolevulinic derivative according to the invention, n is 0.

According to a particular embodiment, is provided a 5-Aminolevulinic derivative according to the invention, n is 1.

According to a particular embodiment, is provided a 5-Aminolevulinic derivative according to the invention, wherein the biocompatible self-removable linker L is of Formula (L):

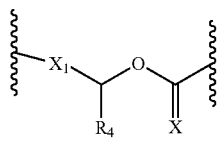
(L)

wherein $R^4$ is selected from H, optionally substituted $C_1$-$C_{30}$ alkyl (e.g. $C_1$-$C_6$ alkyl such as methyl), optionally substituted $C_2$-$C_{30}$ alkenyl (e.g. $C_2$-$C_6$ alkenyl), optionally substituted $C_2$-$C_{30}$ alkynyl (e.g. $C_2$-$C_6$ alkynyl), optionally substituted alkoxy, optionally substituted aryl, optionally substituted heteroaryl, optionally substituted $C_1$-$C_6$ alkyl aryl and optionally substituted aryl $C_1$-$C_6$ alkyl, X is absent or selected from O and S and $X_1$ is selected from the following groups:

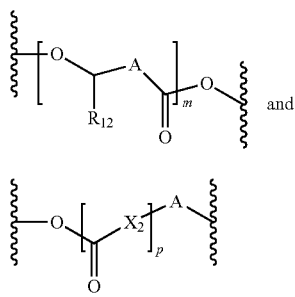
(X1a)

(X1b)

and wherein m is an integer selected from 0 or 1 and p is an integer selected from 0 or 1, $X_2$ is selected from 0, S and NH, $R^{12}$ is selected from H, optionally substituted $C_1$-$C_{30}$ alkyl (e.g. $C_1$-$C_6$ alkyl), optionally substituted $C_2$-$C_{30}$ alkenyl (e.g. $C_2$-$C_6$ alkenyl), optionally substituted $C_2$-$C_{30}$ alkynyl (e.g. $C_2$-$C_6$ alkynyl), optionally substituted alkoxy, optionally substituted aryl and optionally substituted $C_1$-$C_6$ alkyl aryl and A is an optionally substituted aromatic ring.

According to a particular embodiment, is provided a 5-Aminolevulinic derivative according to the invention, wherein B is a phosphate group.

According to a particular embodiment, is provided a 5-Aminolevulinic derivative according to the invention, wherein B is at least one glucuronic acid group.

According to a particular embodiment, is provided a 5-Aminolevulinic derivative according to the invention, wherein B is at least one glycoside group.

According to a particular aspect, is provided a 5-Aminolevulinic derivative according to the invention, wherein B is at least one glycoside group as follows:

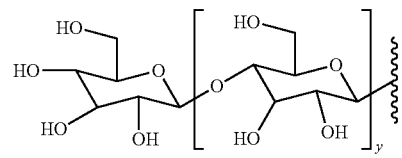

wherein y is an integer selected from 0 and 1'000, for example from 0 to 50, such as from 0 to 10 or from 0 to 1.

According to a particular embodiment, is provided a 5-Aminolevulinic derivative according to the invention, wherein B is a group selected from the following groups:

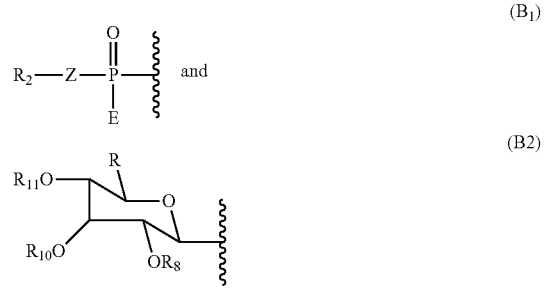
(B1)

(B2)

wherein Z is selected from O and NH and E is selected from —$OR^3$ and a group D2:

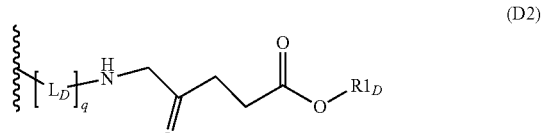
(D2)

$R^2$ and $R^3$ are independently selected from H, optionally substituted $C_1$-$C_{30}$ alkyl (e.g. $C_1$-$C_6$ alkyl), optionally substituted $C_2$-$C_{30}$ alkenyl (e.g. $C_2$-$C_6$ alkenyl), optionally substituted $C_2$-$C_{30}$ alkynyl (e.g. $C_2$-$C_6$ alkynyl), optionally substituted alkoxy, optionally substituted aryl, optionally substituted heteroaryl, optionally substituted $C_3$-$C_8$-cycloalkyl, optionally substituted heterocycloalkyl and a lipidic group; $R1_D$ is selected from H, optionally substituted C1-C30 alkyl (e.g. $C_1$-$C_6$ alkyl), optionally substituted C2-C30 alkenyl (e.g. $C_2$-$C_6$ alkenyl), optionally substituted C2-C30 alkynyl (e.g. $C_2$-$C_6$ alkynyl), optionally substituted alkoxy, optionally substituted aryl, optionally substituted heteroaryl and optionally substituted aryl C1-C6 alkyl (e.g. such as benzyl), q is an integer selected from 0 and 1 and $L_D$ is a biocompatible self-removable linker, R is selected from —$COOR^9$ and —$CH_2OH$, $R^8$, $R^{10}$ and $R^{11}$ are independently selected from H, or an appropriate protective group for hydroxyl groups such as for example optionally substituted $C_1$-$C_6$ alkyl, optionally substituted $C_2$-$C_6$ alkenyl, optionally substituted $C_2$-$C_6$ alkynyl, optionally substituted acyl, optionally substituted acyl sulfonyl, optionally substituted acyl, optionally substituted alkoxy, optionally substituted aryl, optionally substituted heteroaryl, for example forming some of the following groups: esters such as formate, benzoyl formate, optionally substituted acetate such as chloroacetate, dichloroacetate, trichloroacetate, trifluoroacetate, methoxyacetate, phenoxyacetate, phenylacetate, 4-penenoate, 4-oxopentanoate, benzoate, 4-phenylbenzoate, 4-bromobenzoate, 4-nitrobenzoate, picolinate, nicotinate, propanoate, 2-(azidomethyl)benzoate, 4-azidobutyrate, 2-iodobenzoate, 2-(allyloxy)phenylacetate, 4-benzyloxybutyrate, 4-nitro-4methylpentanoate, 2(chloroacetoxymethyl)benzoate, 4-(methylthiomethoxy)butyrate, 4-trialkylsiloxybutyrate, 2-formylbenzenesulfonate, tosylate, allylsulfonate, isobutyrate, 2-chlorobenzoate, 2-trifluoromethylsulfonate, isobutyrate, or carbonates such as methoxymethyl, ethyl, optionally substituted ethyl such as bromoethyl, 2-(methylthiomethoxy)ethyl, 2,2,2-trichloroethyl, 2-(phenylsulfonyl)ethyl, isobutyl, t-butyl, vinyl, allyl, propargyl, 4-chlorophenyl, 4-nitrophenyl, benzyl, 2-nitrobenzyl, 4-nitrobenzyl, 2-(4-nitrophenyl)ethyl, 2-(2,4-dinitrophenyl)ethyl, 2-(2-nitrophenyl)propyl, 2-cyano-1-phenylethyl, phenacetyl, S-benzyl thiocarbonate and $R^9$ is selected from H, optionally substituted $C_1$-$C_{30}$ alkyl, optionally substituted $C_2$-$C_{30}$ alkenyl, optionally substituted $C_2$-$C_{30}$ alkynyl, optionally substituted alkoxy, optionally substituted aryl, optionally substituted heteroaryl, optionally substituted $C_3$-$C_8$-cycloalkyl and optionally substituted heterocycloalkyl.

According to another specific embodiment, $R^4$ is H.

According to a particular embodiment, B is a group B1.

According to a further particular embodiment, B is a group B1 wherein E is —$OR^3$.

According to a further particular embodiment, B is a group B1 wherein Z is —O.

According to a further particular embodiment, $R^3$ is H.

According to a further particular embodiment, B is a group B1, wherein E is —$OR^3$ and at least one group from $R^2$ and $R^3$ is selected from the following group: H, optionally substituted $C_1$-$C_{30}$ alkyl, optionally substituted $C_2$-$C_{30}$ alkenyl, optionally substituted $C_2$-$C_{30}$ alkynyl, optionally substituted aryl (e.g. optionally substituted phenyl such as phenyl), optionally substituted heteroaryl, optionally substituted $C_3$-$C_8$-cycloalkyl, optionally substituted heterocycloalkyl and a lipid group.

According to a further specific embodiment, $R^2$ is an optionally substituted phenyl (e.g. phenyl).

According to another specific embodiment, $R^2$ is a lipid group.

According to a further specific embodiment, $R^2$ is a squalene.

According to another specific embodiment, $R^2$ is H.

According to another specific embodiment, $R^3$ is H.

According to another specific embodiment, $R^1$ is an optionally substituted C1-C30 alkyl such as an optionally substituted C1-C8 alkyl such as methyl, ethyl and hexyl.

According to a further particular embodiment, B is a group B1 wherein E is a group D2.

According to a further particular embodiment, B is a group B1 wherein E is a group D2 and q is 0.

According to another particular embodiment, B is a group B2.

According to another particular embodiment, B is a group B2 wherein R is —$COOR^9$, in particular —COOH According to another particular embodiment, $R^9$ is H.

According to another particular embodiment, $R^8$ is H.
According to another particular embodiment, $R^{10}$ is H.
According to another particular embodiment, $R^{11}$ is H.
According to another further particular embodiment, B is a group B2 wherein R is —$COOR^9$ and $R^8$, $R^9$, $R^{10}$ and $R^{11}$ are H.

According to another particular embodiment, n is 0.
According to another particular embodiment, n is 1.
According to another particular embodiment, n is 1 and X is O.
According to another particular embodiment, $X_1$ is X1a.
According to another particular embodiment, m is 0.
According to another particular embodiment, m is 1.
According to another particular embodiment, $X_1$ is X1a and m is 1.
According to another particular embodiment, $X_1$ is X1b.
According to another particular embodiment, p is 0.
According to another particular embodiment, p is 1.
According to another particular embodiment, $X_1$ is X1b and p is 0.
According to another particular embodiment, $X_1$ is X1b and p is 1
According to another particular embodiment, $X_1$ is X1b and $X_2$ is NH.
According to another particular embodiment, X is O.

According to a particular embodiment, is provided a 5-Aminolevulinic derivative according to the invention, wherein the biocompatible self-removable linker $L_D$ is of Formula (L) or (LD):

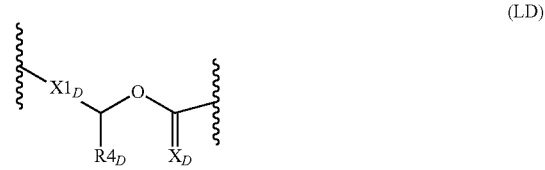

(LD)

wherein $R^{4D}$ is selected from H, optionally substituted $C_1$-$C_{30}$ alkyl (e.g. methyl), optionally substituted $C_2$-$C_{30}$ alkenyl, optionally substituted $C_2$-$C_{30}$ alkynyl, optionally substituted alkoxy, optionally substituted aryl and optionally substituted alkyl-aryl, $X_D$ is absent or selected from O, NH, and S and $X_{1D}$ is selected from

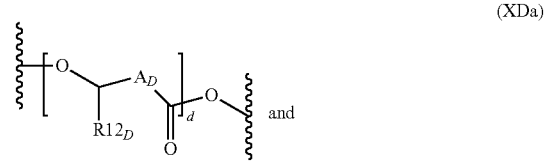

(XDa)

and

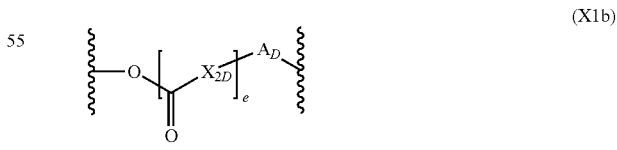

(X1b)

and wherein d is an integer selected from 0 or 1 and e is an integer selected from 0 or 1, $X_{2D}$ is selected from O, S, NH and AD is an optionally substituted aromatic ring, $R^{12D}$ is selected from H, optionally substituted $C_1$-$C_{30}$ alkyl (e.g. methyl), optionally substituted $C_2$-$C_{30}$ alkenyl, optionally substituted $C_2$-$C_{30}$ alkynyl, optionally substituted alkoxy, optionally substituted aryl and optionally substituted alkyl.

According to another further specific embodiment, A is an optionally substituted phenyl ring (e.g. phenyl, nitro phenyl).

According to another further specific embodiment, A is an optionally substituted phenyl ring selected from the following group:

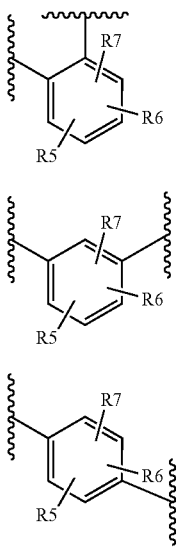

A1

A2

A3 wherein $R^5$, $R^6$ and $R^7$ are independently selected from H, halogen (such as F, Cl, Br, I), amino (such as $NH_2$), nitro and the like or optionally at least one group among $R^5$, $R^6$ and $R^7$ is a group of Formula D3:

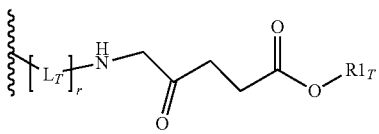

(D3)

$R1_T$ is $R^4$ or is selected from H, optionally substituted C1-C30 alkyl, optionally substituted C2-C30 alkenyl, optionally substituted C2-C30 alkynyl, optionally substituted alkoxy, optionally substituted aryl, optionally substituted C1-C6 alkyl aryl and optionally substituted heteroaryl, r is an integer selected from 0 and 1 and $L_T$ is a biocompatible self-removable linker.

According to a particular embodiment, is provided a 5-Aminolevulinic derivative according to the invention, wherein the biocompatible self-removable linker $L_T$ is of Formula (L) Formula (LD) or (LT):

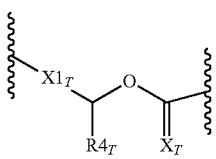

(LT)

wherein $R_{4T}$ is selected from H, optionally substituted $C_1$-$C_{30}$ alkyl (e.g. methyl), optionally substituted $C_2$-$C_{30}$ alkenyl, optionally substituted $C_2$-$C_{30}$ alkynyl, optionally substituted alkoxy, optionally substituted aryl and optionally substituted alkyl-aryl, $X_T$ is absent or selected from O and S and $X_{1T}$ is absent or selected from the following groups:

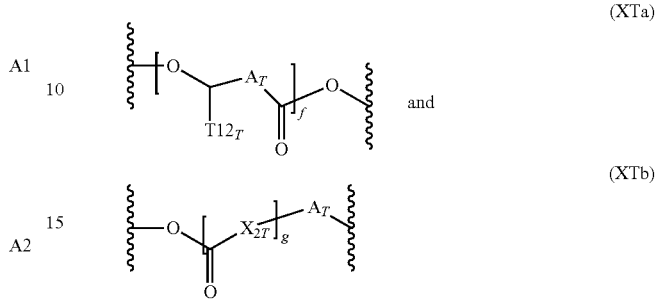

(XTa)

(XTb)

and wherein f is an integer selected from 0 or 1 and g is an integer selected from 0 or 1, $X_{2T}$ is selected from O, S, NH and AT is an optionally substituted aromatic ring, $R^{12T}$ is selected from H, optionally substituted $C_1$-$C_{30}$ alkyl (e.g. methyl), optionally substituted $C_2$-$C_{30}$ alkenyl, optionally substituted $C_2$-$C_{30}$ alkynyl, optionally substituted alkoxy, optionally substituted aryl and optionally substituted alkyl-aryl.

According to another further specific embodiment, AD is an optionally substituted phenyl ring.

According to another further specific embodiment, AD is an optionally substituted phenyl ring selected from the following group:

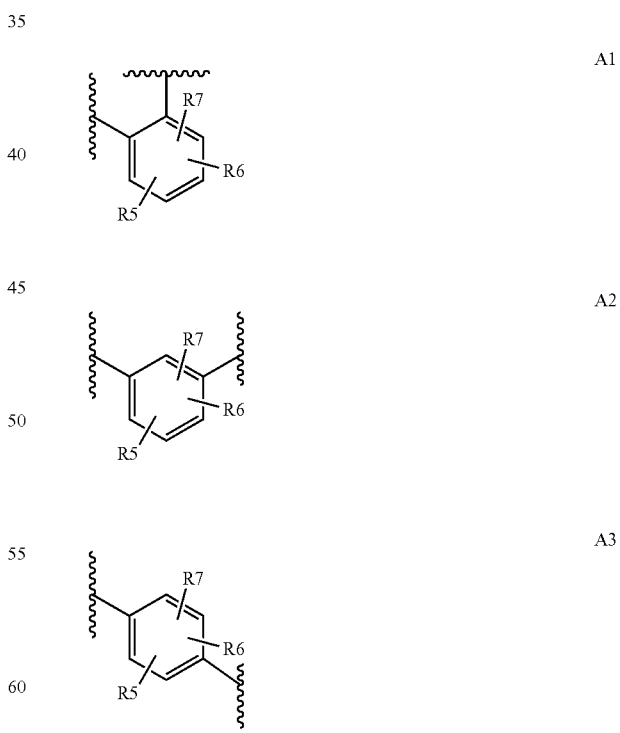

A1

A2

A3 wherein $R^5$, $R^6$ and $R^7$ are independently selected from H, halogen (such as F, Cl, Br, I), amino (such as $NH_2$), nitro and the like or optionally at least one group among $R^5$, $R^6$ and $R^7$ is a group of Formula D4:

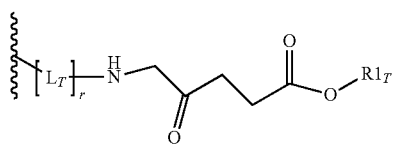
(D4)

R1$_T$ is selected from H, optionally substituted C1-C30 alkyl, optionally substituted C2-C30 alkenyl, optionally substituted C2-C30 alkynyl, optionally substituted alkoxy, optionally substituted aryl and optionally substituted heteroaryl, q is an integer selected from 0 and 1 and L$_T$ is a biocompatible self-removable linker.

In particular, AT is an optionally substituted phenyl.

According to a further aspect, the invention provides a 5-ALA derivative selected from the following group:

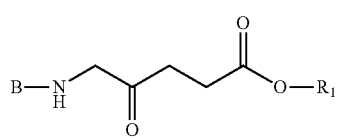
(Ia)

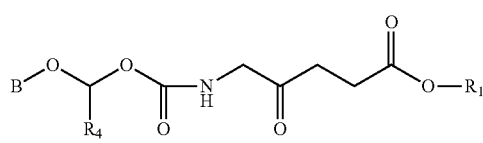
(Ib)

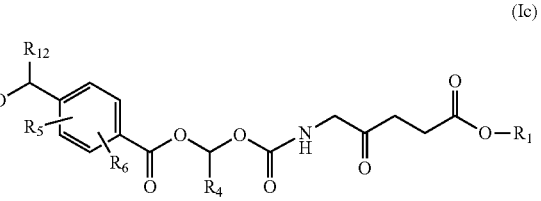
(Ic)

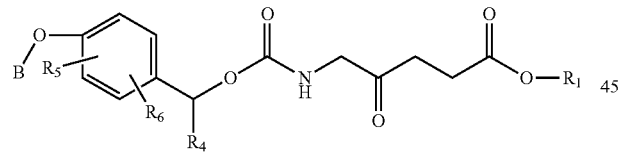
(Id)

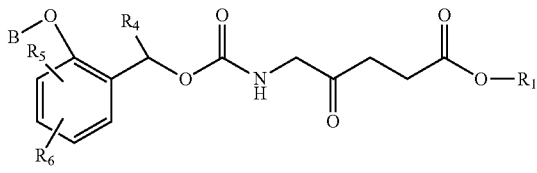
(Ie)

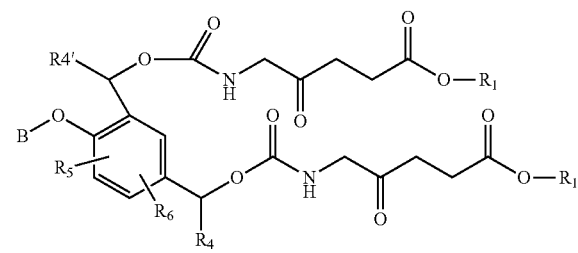
(If)

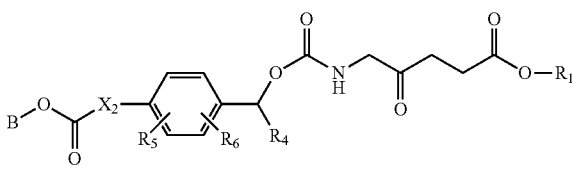
(Ig)

Wherein $R^1$, $R^2$, $R^3$, $R^4$, $R^5$, $R^6$ and $R^{12}$ are as defined in the present description and R4' can be $R^4$ or selected from H, optionally substituted $C_1$-$C_{30}$ alkyl (e.g. methyl), optionally substituted $C_2$-$C_{30}$ alkenyl, optionally substituted $C_2$-$C_{30}$ alkynyl, optionally substituted alkoxy, optionally substituted aryl and optionally substituted alkyl-aryl.

According to a particular embodiment, $R_4'$ is $R^4$ or selected from H, optionally substituted $C_1$-$C_{30}$ alkyl, optionally substituted $C_2$-$C_{30}$ alkenyl, optionally substituted $C_2$-$C_{30}$ alkynyl, optionally substituted alkoxy, optionally substituted aryl and optionally substituted alkyl-aryl, $R^5$ and $R^6$ are independently selected from H, halogen, amino, nitro or optionally at least one group among R5 and $R^6$ is a group of Formula D3 as defined above.

According to another further aspect, the invention provides a 5-ALA derivative of Formula (I), wherein $R^1$ is H.

According to another further aspect, the invention provides a 5-ALA derivative of Formula (I), wherein $R^1$ is an optionally substituted C1-C30 alkyl (such as C1-C6 alkyl, like hexyl or methyl).

According to another further aspect, the invention provides a 5-ALA derivative of Formula (I), wherein $R^1$ is an optionally substituted aryl C1-C6 alkyl (e.g. such as benzyl).

According to a further aspect, the invention provides a 5-ALA derivative selected from the following group:

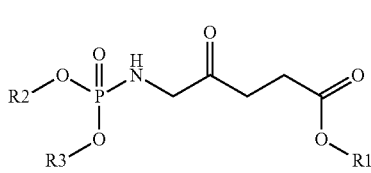
(IB1a1)

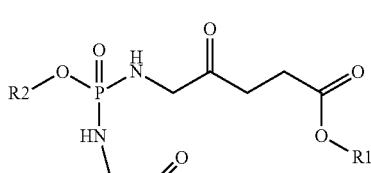
(IB1a2)

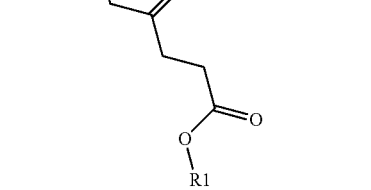

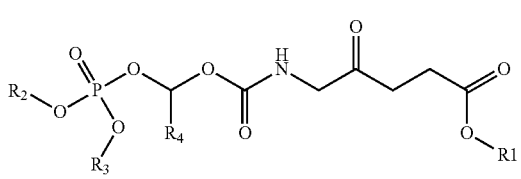
(IB1b)

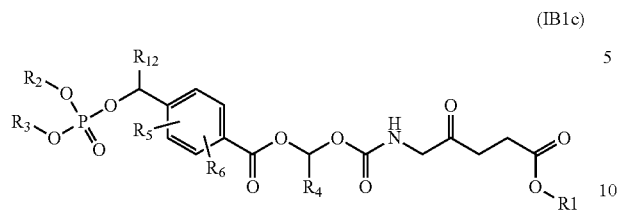

(IB1c)

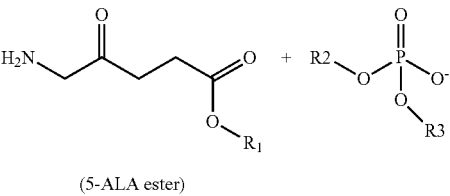

(5-ALA ester)

Scheme 2

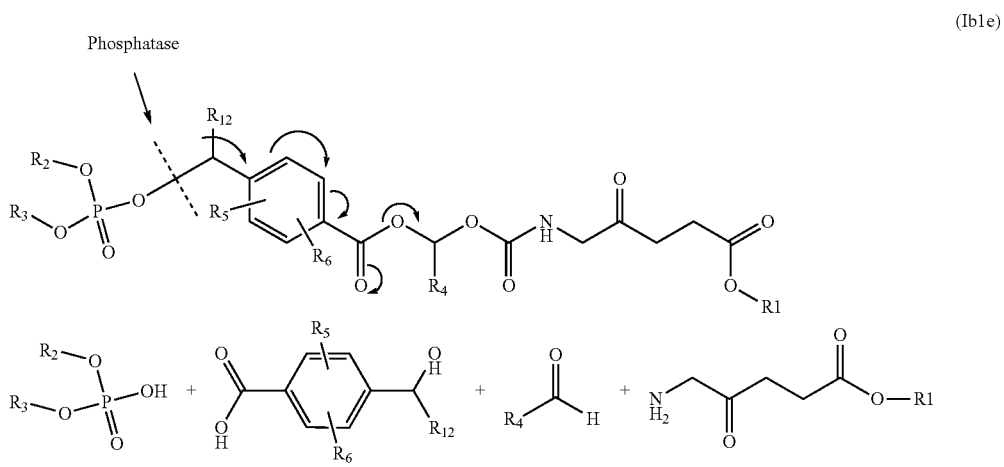

-continued (IB1d)

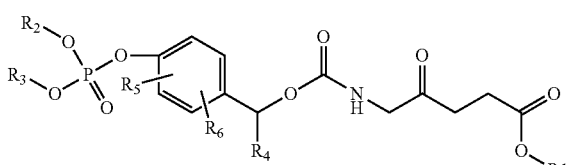

Wherein $R^1$, $R^2$, $R^3$, $R^4$, $R^5$, $R^6$ and $R^{12}$ are as defined in the present description. The following Schemes 1, 2 and 3 illustrate the mechanisms of activation of a compound of the invention (IB1a1), (IB1c) and (IB1d), respectively:

Scheme 3

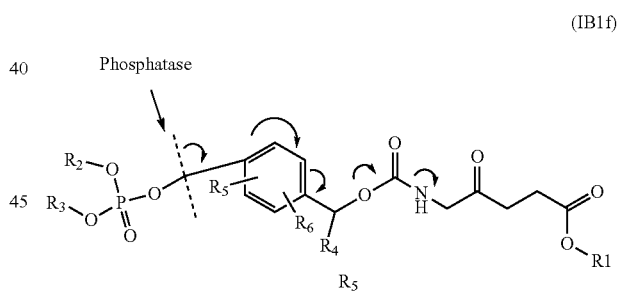

According to another further aspect, the invention provides a 5-ALA derivative of Formula (IB1a).

According to another further aspect, the invention provides a 5-ALA derivative of Formula (IB1a) selected from the following group:

triethylammonium salt of hexyl 5-((hydroxy(phenoxy)phosphoryl)amino)-4-oxopentanoate;

Scheme 1

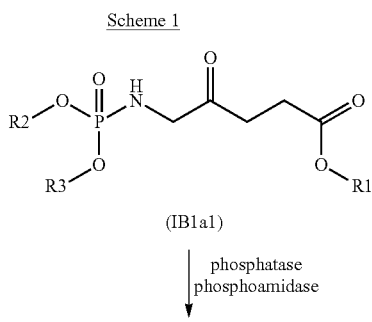

(IB1a1)

↓ phosphatase
phosphoamidase triethylammonium salt of methyl 5-((hydroxy(phenoxy)phosphoryl) amino)-4-oxopentanoate
triethylammonium salt of benzyl 5-((hydroxy(phenoxy)phosphoryl) amino)-4-oxopentanoate and
hexyl 5-((hydroxy(((4E,8E,12E,16E)-4,8,13,17,21-pentamethyldocosa-4,8,12,16,20-pentaen-1-yl)oxy)phosphoryl) amino)-4-oxopentanoate.

According to another further aspect, the invention provides a 5-ALA derivative of Formula (IB1b) selected from the following group:
Bis(hexyl) 5-((hydroxy(phenoxy)phosphoryl)bis(amino)-4-oxopentanoate) and Bis-hexyl 5-((hydroxy(((4E,8E,12E,16E)-4,8,13,17,21-pentamethyldocosa-4,8,12,16,20-pentaen-1-yl)oxy)phosphoryl)bis-amino)-4-oxopentanoate.

According to another further aspect, the invention provides a 5-ALA derivative of Formula (IB1c) selected from the following group:
Triethylammonium salt of hexyl 4-oxo-5-((((phosphonooxy)methoxy)carbonyl)amino) pentanoate; and
Triethylammonium salt of methyl 4-oxo-5-((((phosphonooxy)methoxy)carbonyl)amino) pentanoate.

According to a further aspect, the invention provides the 5-ALA derivative selected from the following group:

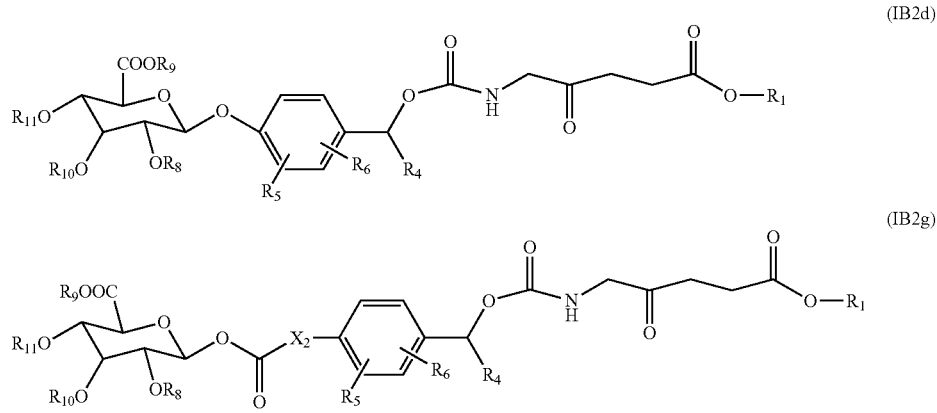

wherein $X_2$, $R^1$, $R^4$, $R^5$, $R^6$, $R^8$, $R^9$, $R^{10}$ and $R^{11}$ are as defined in the present description. The following Scheme 4 illustrates the mechanisms of activation of a compound of the invention (IB2g).

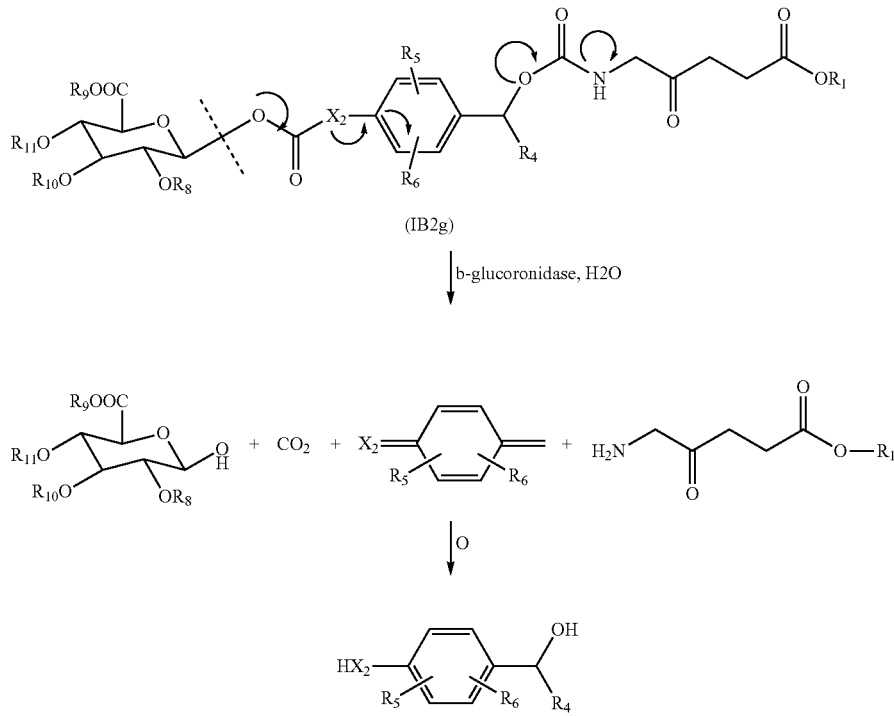

According to a further aspect, the invention provides the 5-ALA derivative of Formula (IB2f) selected from the following group:
(2S,3S,4S,5R,6R)-6-(((4-((((5-(hexyloxy)-2,5-dioxopentyl)carbamoyl)oxy)methyl) phenyl)carbamoyl)oxy)-3,4,5-trihydroxytetrahydro-2H-pyran-2-carboxylic acid.

According to a further aspect, the invention provides the 5-ALA derivative of Formula (IB2c) selected from the following group:
(2S,3S,4S,5R,6R)-6-(4-((((4-carboxy-2-oxobutyl)carbamoyl)oxy)methyl)-2-nitrophenoxy)-3,4,5-trihydroxytetrahydro-2H-pyran-2-carboxylic acid.

Preparation of the Derivatives According to the Invention

Compounds of the invention can be synthesized by standard methods of the art, for example, as described below. A general scheme for synthesis of compounds of the invention, in particular, compounds of Formula (IB1a1) can be synthesized as described under Scheme 5 below, wherein R1, R2 and R3 are as defined in the present description and R2p and R3p correspond to either groups R2 and R3, respectively or to groups R2 and R3, respectively protected with appropriate protective groups such to form one of the following groups: H, optionally substituted $C_1$-$C_{30}$ alkyl, optionally substituted $C_2$-$C_{30}$ alkenyl, optionally substituted $C_2$-$C_{30}$ alkynyl, methyl, ethyl, propyl, isopropyl, cyclohexyl, t-butyl, 1-adamantyl, allyl, 2-trimethylsilylprop-2-enyl, hexafluoro-2-butyl, 2-mercaptoethyl, ethyleneglycolyl, 3-pivaloyl-1,3-dihydroxypropyl, 4-methylthio-1-butyl, 4-(N-trifluoroacetylamino)butyl, 2-(S-acetylthio)ethyl, 4-oxopentyl, 3-(N-t-butylcarboxamido)-1-propyl, 3-(pyridyl)-1-propyl, 2-(N-methyl-N-(2-pyridyl)amino-ethyl, 2-(N-formyl-N-methyl)aminoethyl, 2-(N-isopropyl-N-methyl)aminoethyl, 2-((1-naphtyl)carbamoyloxy)ethyl, 2-cyanoethyl, 2-cyano-1,1-dimethylethyl, 4-cyano-2-butenyl, 2-(methyldiphenylsilyl)ethyl, 2-(trimethylsilyl)ethyl, 2-(triphenylsilyl)ethyl, 2-(4-nitrophenyl)ethyl, 2-(alfa-pyridyl)ethyl, 2-(4'-pyridyl)ethyl, 2-(phenylthio)ethyl, 2-(4-nitrophenyl)thioethyl, 2-(methylsulfonyl)ethyl, 2-(benzylsulfonyl)ethyl, 2-(t-butylsulfonyl)ethyl, 2,2,2-trichloroethyl, 2,2,2-trichloro-1,1dimethylethyl, 2,2,2-tribromoethyl, 2,2,2-trifluoroethyl, 1,1,1,3,3,3-hexafluoro-2-propyl, benzyl, 4-methoxybenzyl, 4-nitrobenzyl, 2,4,-dinitrobenzyl, 4-chlorobenzyl, 4-chloro-2-nitrobenzyl, 4-acyloxybenzyl, 1-oxido-4-methoxy-2-picolyl, fluorenyl-9-methyl, 5-benzisoxazolylmethylene, 2-(9,10-anthraquinonyl)methyl, diphenylmethyl, phenyl, 2,-xylenyl, 2-methylphenyl, 2-chlorophenyl, 4-chlorophenyl, 2,4-dichlorophenyl, 2,5-dichlorophenyl, 2,6-dichlorophenyl, 2-bromophenyl, 4-bromophenyl, 4-nitrophenyl, 4-chloro-2-nitrophenyl, 2-chloro-4-tritylphenyl, 2-methoxy-5-nitrophenyl, 4-tritylaminophenyl, 4-benzylaminophenyl, 8-quinolyl, thiophenyl, 5-chloro-8-quinolyl, pyrenylmethyl, 3,5-dinitrophenyl, 4-hydroxyphenacyl, benzoin, 4-methoxyphenacyl, ethoxycarbonyl.

Scheme 5

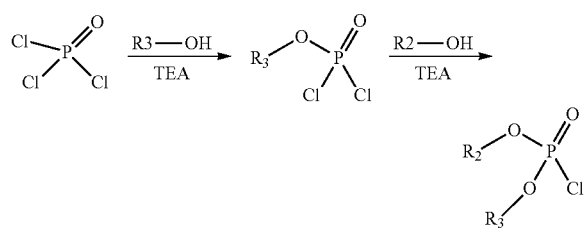

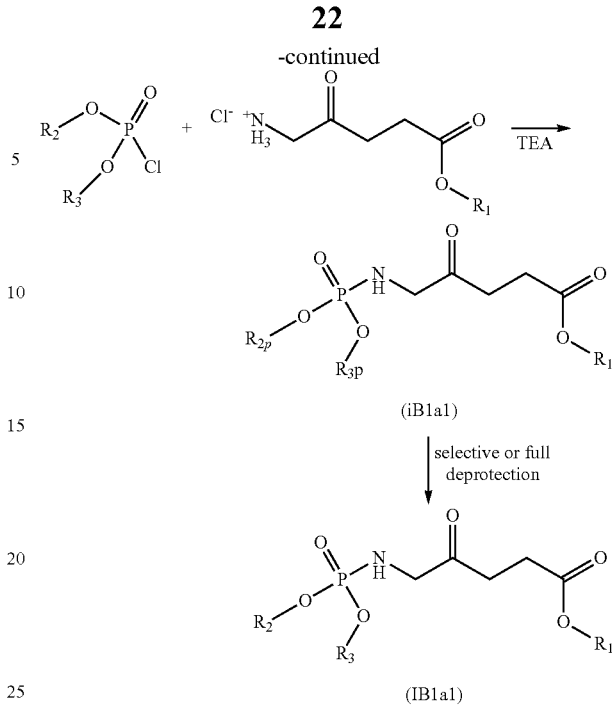

selective or full deprotection (IB1a1)

Phosphoryl trichloride (1.0 mmol) was dissolved in dry dichloromethane (100 mL) and alcohol (R3-OH) (1.0 mmol) is added at 0° C. followed by slow addition of dry triethylamine (1.1 mmol) and DMAP (0.2 mmol). The reaction mixture was stirred for 2h at 0° C. when the second alcohol (R2-OH) (1.0 mmol) was added followed by triethylamine (1.1 mmol) and the reaction mixture stirred at 0° C. After 4h the aminolevulinic acid ester (ALA-R1) (1.5 mmol) was added followed by very slow dropwise addition of triethylamine (3.0 mmol). The reaction mixture was allowed to warm up to ambient temperature and stirred overnight. Water was added and extracted with dichloromethane (3×50 mL). The organic fraction pooled, washed with brine, dried over sodium sulfate and evaporated under reduced pressure. The crude product was purified by Flash chromatography using DCM/MeOH gradient. The fractions containing the product pooled and evaporated under reduced pressure. Colorless product was obtained.

In particular, compounds of Formula (IB1a2) can be synthesized as described under Scheme 6 below, wherein R1 and R2 are as defined in the present description and R2p corresponds to group R2 or to R2 protected with appropriate protective groups such as such to form one of the following groups: H, optionally substituted $C_1$-$C_{30}$ alkyl, optionally substituted $C_2$-$C_{30}$ alkenyl, optionally substituted $C_2$-$C_{30}$ alkynyl, methyl, ethyl, propyl, isopropyl, cyclohexyl, t-butyl, 1-adamantyl, allyl, 2-trimethylsilylprop-2-enyl, hexafluoro-2-butyl, 2-mercaptoethyl, ethyleneglycolyl, 3-pivaloyl-1,3-dihydroxypropyl, 4-methylthio-1-butyl, 4-(N-trifluoroacetylamino)butyl, 2-(S-acetylthio)ethyl, 4-oxopentyl, 3-(N-t-butylcarboxamido)-1-propyl, 3-(pyridyl)-1-propyl, 2-(N-methyl-N-(2-pyridyl)amino-ethyl, 2-(N-formyl-N-methyl)aminoethyl, 2-(N-isopropyl-N-methyl)aminoethyl, 2-((1-naphtyl)carbamoyloxy)ethyl, 2-cyanoethyl, 2-cyano-1,1-dimethylethyl, 4-cyano-2-butenyl, 2-(methyldiphenylsilyl)ethyl, 2-(trimethylsilyl)ethyl, 2-(triphenylsilyl)ethyl, 2-(4-nitrophenyl)ethyl, 2-(alfa-pyridyl)ethyl, 2-(4'-pyridyl)ethyl, 2-(phenylthio)ethyl, 2-(4-nitrophenyl)thioethyl, 2-(methylsulfonyl)ethyl, 2-(benzylsulfonyl)ethyl, 2-(t-butylsulfonyl)ethyl, 2,2,2-trichloroethyl, 2,2,2-trichloro-1,1dimethylethyl, 2,2,2-tribromoethyl, 2,2,2-trifluoroethyl, 1,1,1,3,3,3-hexafluoro-2-propyl, benzyl, 4-methoxybenzyl, 4-nitrobenzyl, 2,4,-dinitrobenzyl, 4-chlorobenzyl, 4-chloro-2-nitrobenzyl, 4-acyloxybenzyl, 1-oxido-4-methoxy-2-picolyl, fluorenyl-9-methyl, 5-benzisoxazolylmethylene, 2-(9,10-anthraquinonyl)methyl, diphenylmethyl, phenyl, 2,-xylenyl, 2-methylphenyl, 2-chlorophenyl, 4-chlorophenyl, 2,4-dichlorophenyl, 2,5-dichlorophenyl, 2,6-dichlorophenyl, 2-bromophenyl, 4-bromophenyl, 4-nitrophenyl, 4-chloro-2-nitrophenyl, 2-chloro-4-tritylphenyl, 2-methoxy-5-nitrophenyl, 4-tritylaminophenyl, 4-benzylaminophenyl, 8-quinolyl, thiophenyl, 5-chloro-8-quinolyl, pyrenylmethyl, 3,5-dinitrophenyl, 4-hydroxyphenacyl, benzoin, 4-methoxyphenacyl, ethoxycarbonyl.

dropwise addition of triethylamine (7.0 mmol). The reaction mixture was kept at 0° C. for 6h and then allowed to warm up to ambient temperature and stirred overnight. Water was added and extracted with dichloromethane (3×50 mL). The organic fraction pooled, washed with brine, dried over sodium sulfate and evaporated under reduced pressure. The crude product was purified by Flash chromatography using DCM/MeOH gradient. The fractions containing the product pooled and evaporated under reduced pressure. Colorless product was obtained.

In particular, compounds of Formula (IB1b) can be synthesized as described under Scheme 7 below, wherein R1, R2 and R3 are as defined in the present description and R2p and R3p are as defined herein:

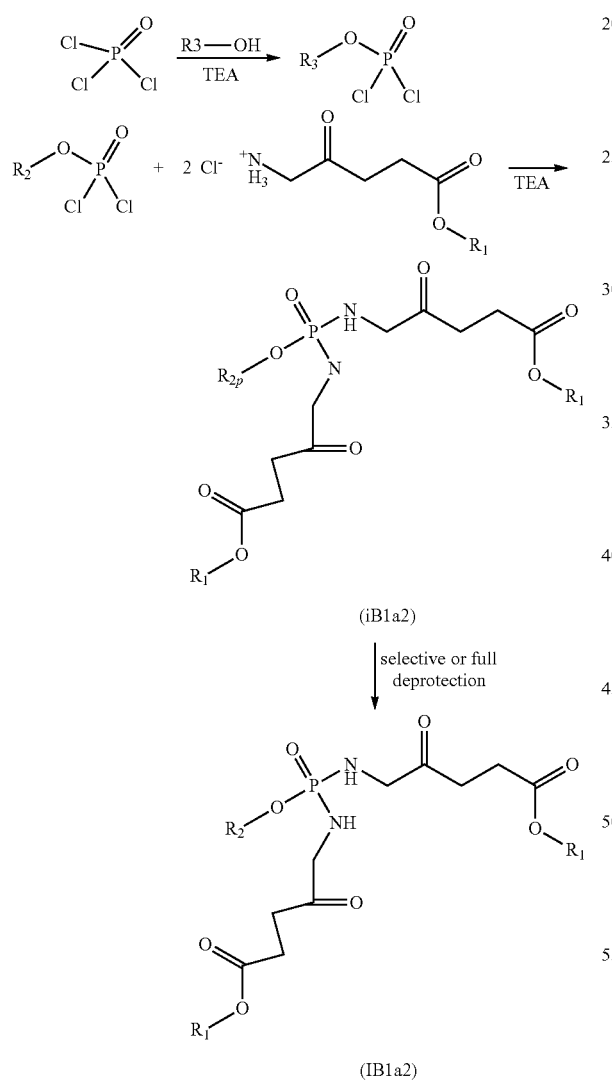

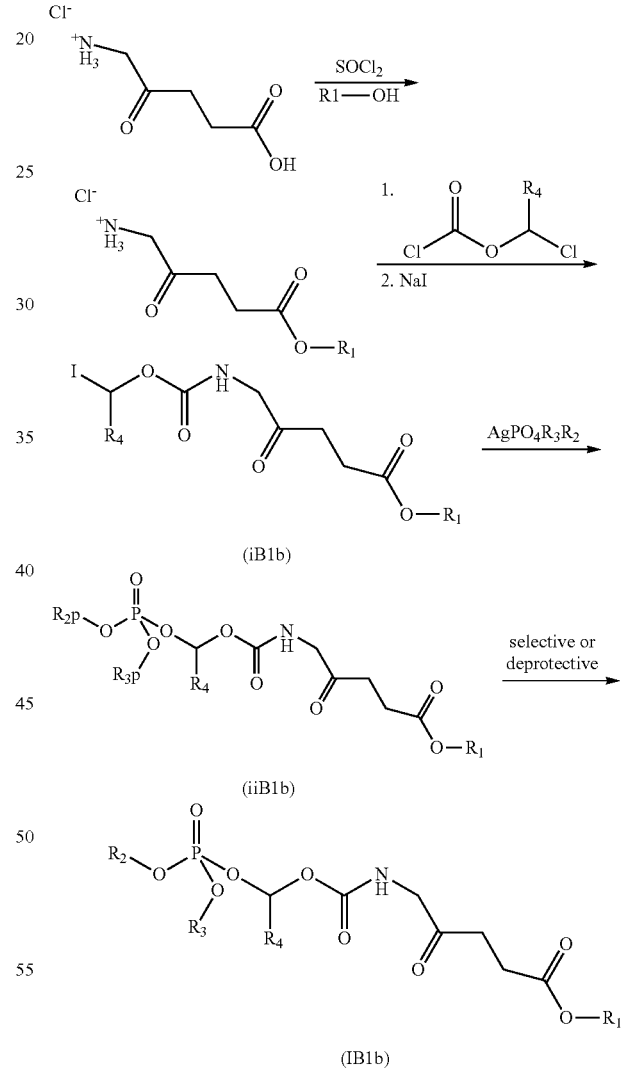

Phosphoryl trichloride (1.0 mmol) was dissolved in dry dichloromethane (100 mL) and alcohol (R3-OH) (1.0 mmol) is added at 0° C. followed by slow addition of dry triethylamine (1.1 mmol) and DMAP (0.2 mmol). The reaction mixture was stirred for 2h at 0° C. Aminolevulinic acid ester (ALA-R1) (3.5 mmol) was added followed by very slow Ester of 5-amino-4-oxopentanoate hydrochloride salt (1.00 mmol) was dissolved in dry DCM (20.0 mL) and cooled to −20° C. under argon atmosphere. Chloroalkyl chloroformate (1.10 mmol) was added under stirring in one portion followed by dropwise addition of triethylamine (417 μL, 3.00 mmol) dissolved in dry DCM (5.0 mL). The reaction mixture was stirred for 1h at −20° C. and allowed to warm up to ambient temperature. After quenching the reaction with water (5.0 mL) the reaction mixture was extracted with DCM (2×20 mL). The organic phase was washed with diluted HCl (2×10 mL) and saturated NaHCO$_3$ solution and dried over Na$_2$SO$_4$. The product was purified by Flash chromatography using DCM/MeOH gradient giving colorless oil.

Ester of 5-(((chloroalkoxy)carbonyl)amino)-4-oxopentanoate (0.60 mmol) was added to a suspension of sodium iodide (2.93 mmol) in acetone (20.0 mL) and refluxed at 60° C. for 1h. The solvent was evaporated under reduced pressure and water (10 mL) added. The product was extracted with ether (3×20 mL) and dried over Na$_2$SO$_4$. After the solvent was evaporated colorless oil was obtained and used immediately in the next step without purification. Ester of 5-(((iodoalkoxy)carbonyl)amino)-4-oxopentanoate (0.1 mmol) was dissolved in toluene (10.0 mL) followed by the addition of silver salt of R2,R3-substituted phosphate (0.13 mmol) synthesized previously according to published procedures. The suspension was stirred at ambient temperature in the dark overnight. The brown precipitate was filtered off and the solvent evaporated under reduced pressure. The crude product was purified by Flash chromatography using DCM/MeOH gradient yielding colourless oil.

In particular, compounds of Formula (IB1c) can be synthesized as described under Scheme 8 below, wherein R1, R2 and R3 are as defined in the present description and R2p and R3p are as defined herein:

Scheme 8

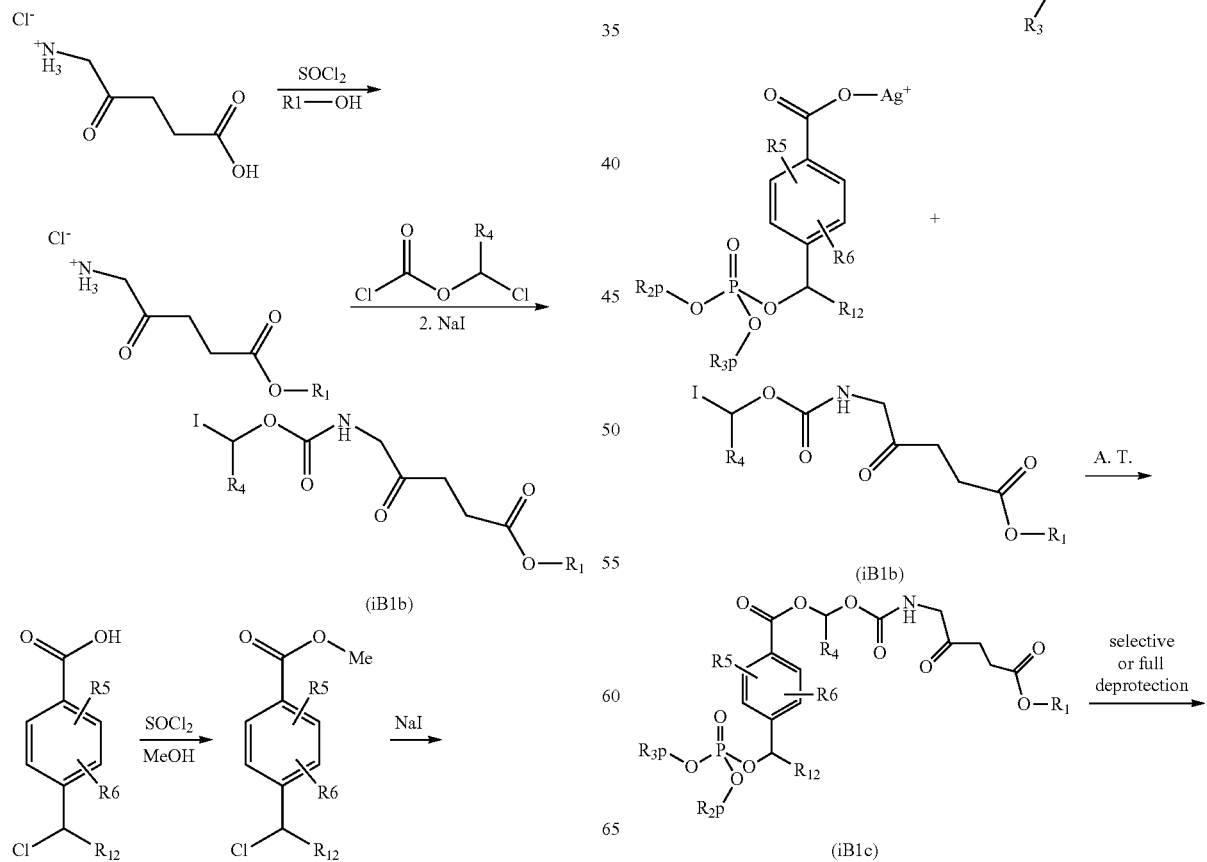

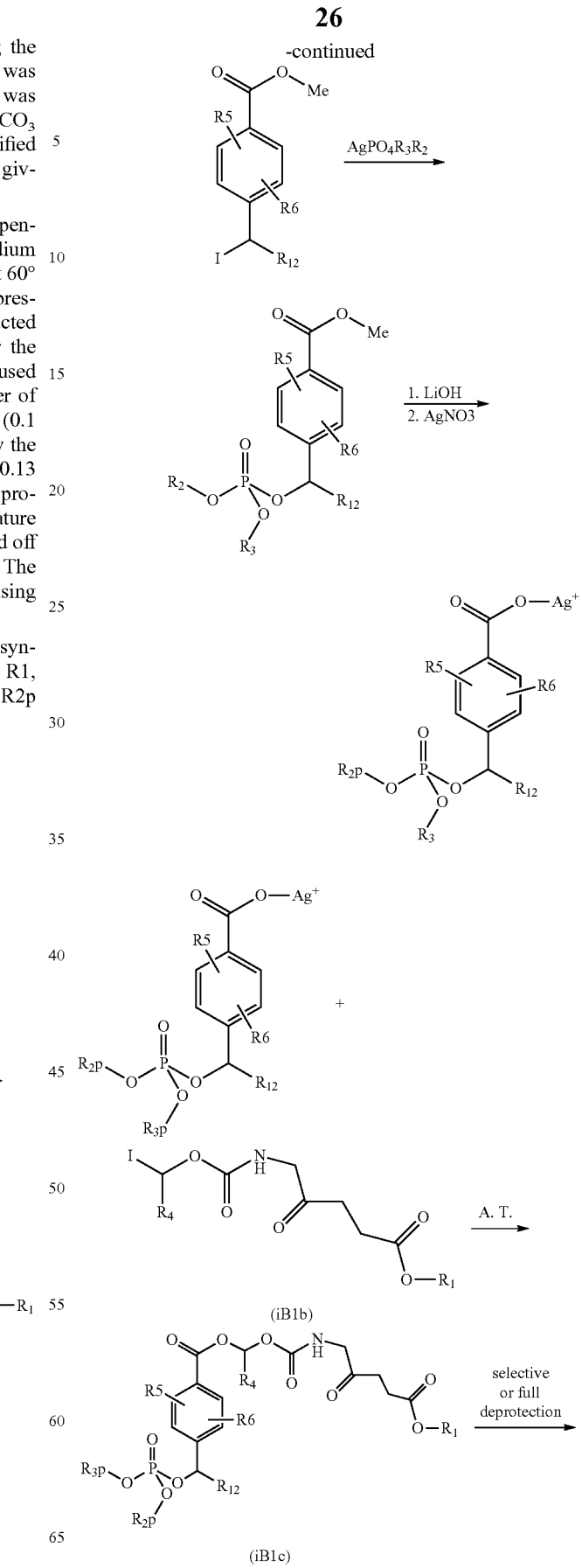

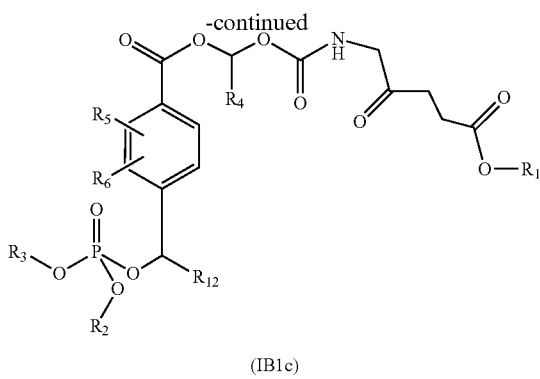

(IB1c)

R1-ester of 5-amino-4-oxopentanoate hydrochloride salt (1.00 mmol) was dissolved in dry DCM (20.0 mL) and cooled to −20° C. under argon atmosphere. Chloro-R7-alkyl chloroformate (1.10 mmol) was added under stirring in one portion followed by dropwise addition of triethylamine (417 μL, 3.00 mmol) dissolved in dry DCM (5.0 mL). The reaction mixture was stirred for 1 h at −20° C. and allowed to warm up to ambient temperature. After quenching the reaction with water (5.0 mL) the reaction mixture was extracted with DCM (2×20 mL). The organic phase was washed with diluted HCl (2×10 mL) and saturated NaHCO$_3$ solution and dried over Na$_2$SO$_4$. The product was purified by Flash chromatography using DCM/MeOH gradient giving colorless oil.

R1-ester of 5-(((chloro-R7-alkoxy)carbonyl)amino)-4-oxopentanoate (0.60 mmol) was added to a suspension of sodium iodide (2.93 mmol) in acetone (20.0 mL) and refluxed at 60° C. for 1h. The solvent was evaporated under reduced pressure and water (10 mL) added. The product was extracted with ether (3×20 mL) and dried over Na$_2$SO$_4$. After the solvent was evaporated colorless oil was obtained and used immediately in the next step without purification.

Thionyl chloride (12.0 mmol) was added dropwise to a cooled methanol (3.0 mL). Once the formation of HCl gas stops R5,R6-substituted-4-(R4-methyl-chloride) benzoic acid (6.0 mmol) dissolved in dichloromethane (20.0 mL) was added to the cooled reaction mixture. After 24h at ambient temperature the starting material was consumed and the solvents were evaporated under reduced pressure. The crude product was dissolved in ether (50.0 mL) and washed with saturated sodium bicarbonate solution (3×20 mL), dried with sodium sulfate and the solvent evaporated under reduced pressure to yield colourless product. Methyl R5,R6-substituted-4-(R4-methyl-chloride) benzoate (4.47 mmol) was dissolved in acetone (100 mL) and sodium iodide (22.35 mmol) was added and the suspension refluxed at 70° C. After 3h the solvent was evaporated under reduced pressure and the crude product suspended in ether (50 mL) and washed with water (2×20 mL), brine (20 mL), dried over sodium sulphate and evaporated under reduced pressure. Colourless solid was obtained after crystallization from ether.

Methyl R5,R6-substituted-4-(R4-methyl-iodide) benzoate (1.81 mmol) and silver salt of R2,R3-phosphate (2.0 mmol) were suspended in toluene (50 mL) and stirred at ambient temperature overnight protected from light. The yellow precipitate was filtered off and the solvent evaporated under reduced pressure. The crude product was purified by Flash chromatography using hexane/ether gradient yielding colourless product.

Methyl R5,R6-substituted-4-(R4-methyl-R2,R3-phospho) benzoate (0.270 mmol) was dissolved in a mixture of water/methanol/tetrahydrofurane 1/1/1 (3.0 mL) followed by the addition of 1M lithium hydroxide solution (0.81 mL). After 2h at ambient temperature the pH was adjusted to 7-8 with diluted HCl and silver nitrate (0.32 mmol) dissolved in water (1.0 mL) was added. A solid precipitated from the solution and was filtered off, washed with water (2.0 mL) and extensively dried in vacuo yielding colourless solid.

Silver salt of R5,R6-substituted-4-(R4-methyl-R2,R3-phospho) benzoate (0.124 mmol) and R1-ester of 5-(((chloro-R7alkoxy)carbonyl)amino)-4-oxopentanoate (0.60 mmol) were suspended in toluene and heated at 60° C. for 30 min. After the evaporation of the solvent under reduced pressure the crude product was purified by Flash chromatography using dichloromethane/methanol gradient. Colourless product was obtained.

According to the substituents R2, R3 and R1 selective or full deprotection was performed using standard methods to one skilled in the art for functional group deprotection (Wuts, P. G. M, Greene, T. W. *Greene's Protective Groups in Organic Synthesis*, 4th Ed. John Wiley&Sons, 2007).

In particular, compounds of Formula (IB1d) can be synthesized as described under Scheme 9 below, wherein R1, R2 and R3 are as defined in the present description and R2p and R3p are as defined herein:

Scheme 9

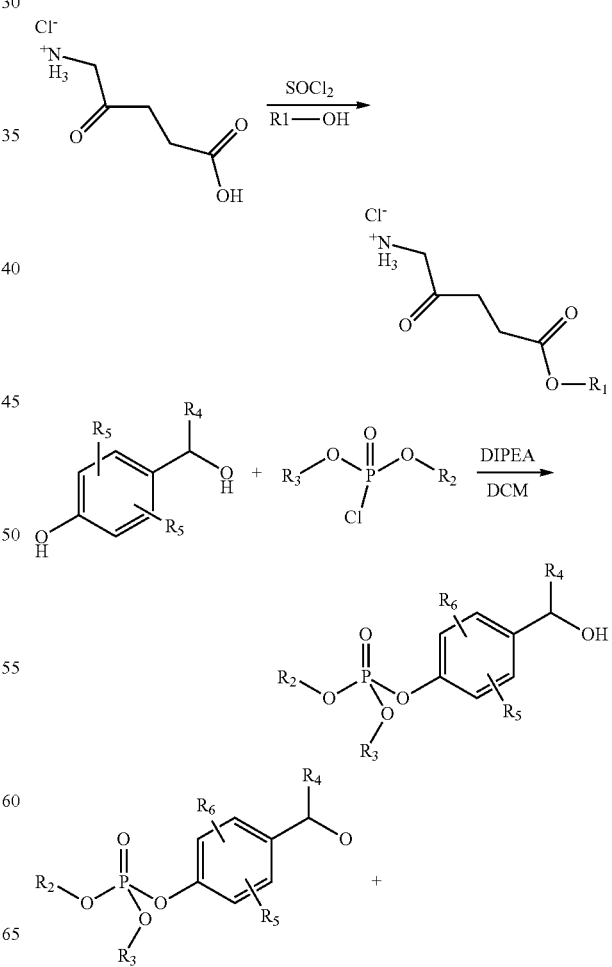

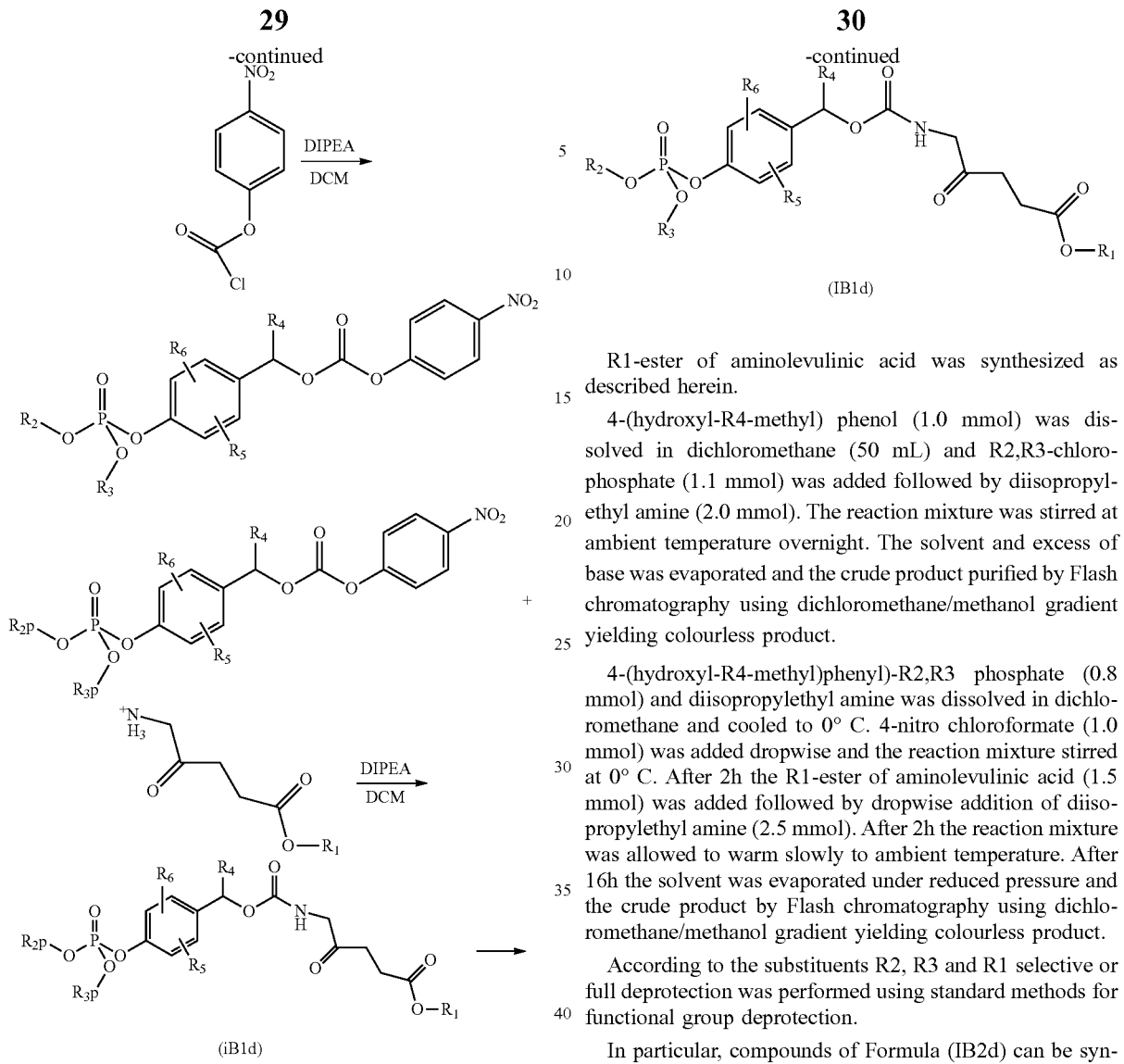

R1-ester of aminolevulinic acid was synthesized as described herein.

4-(hydroxyl-R4-methyl) phenol (1.0 mmol) was dissolved in dichloromethane (50 mL) and R2,R3-chlorophosphate (1.1 mmol) was added followed by diisopropylethyl amine (2.0 mmol). The reaction mixture was stirred at ambient temperature overnight. The solvent and excess of base was evaporated and the crude product purified by Flash chromatography using dichloromethane/methanol gradient yielding colourless product.

4-(hydroxyl-R4-methyl)phenyl)-R2,R3 phosphate (0.8 mmol) and diisopropylethyl amine was dissolved in dichloromethane and cooled to 0° C. 4-nitro chloroformate (1.0 mmol) was added dropwise and the reaction mixture stirred at 0° C. After 2h the R1-ester of aminolevulinic acid (1.5 mmol) was added followed by dropwise addition of diisopropylethyl amine (2.5 mmol). After 2h the reaction mixture was allowed to warm slowly to ambient temperature. After 16h the solvent was evaporated under reduced pressure and the crude product by Flash chromatography using dichloromethane/methanol gradient yielding colourless product.

According to the substituents R2, R3 and R1 selective or full deprotection was performed using standard methods for functional group deprotection.

In particular, compounds of Formula (IB2d) can be synthesized as described under Scheme 10 below:

Scheme 10

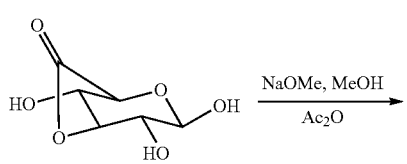

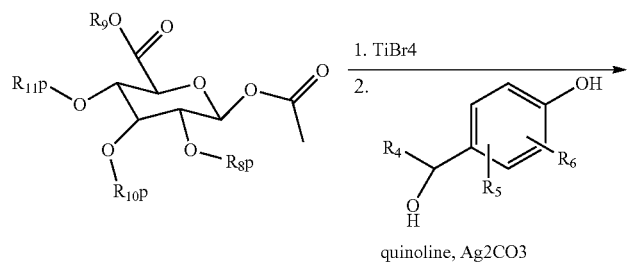

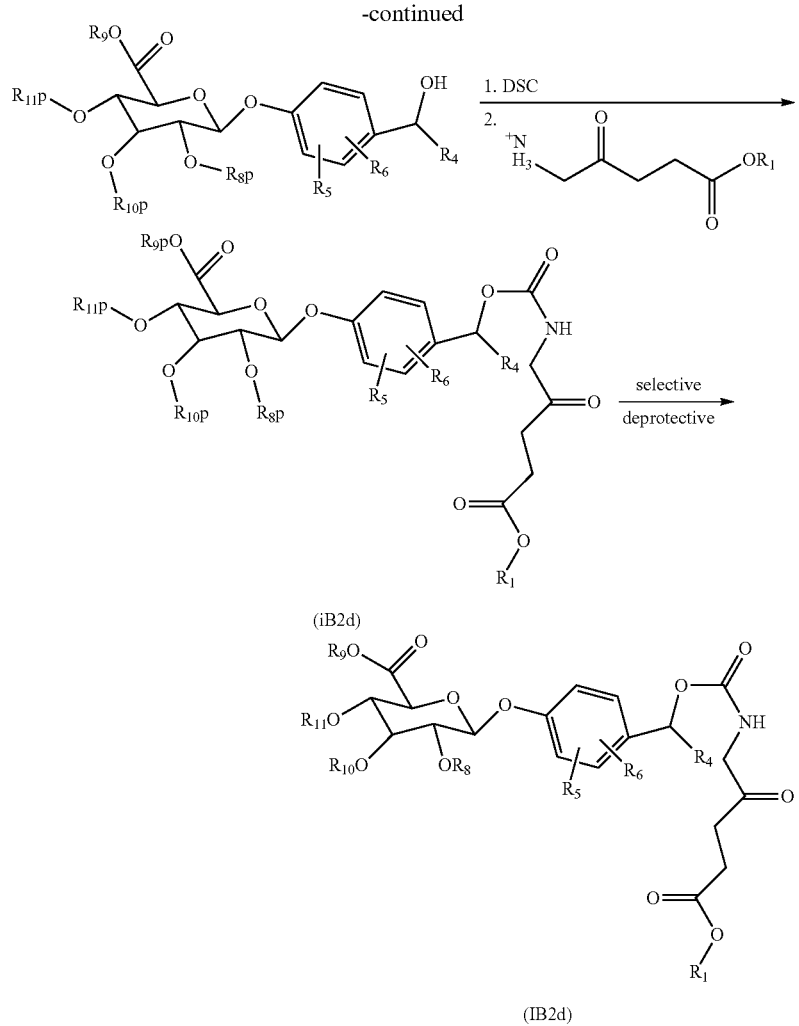

(IB2d)

wherein $R^1$, $R^8$, $R^9$, $R^{10}$ and $R^{11}$ are as defined in the present description and R8p, R9p, R10p and R11p correspond to either groups $R^8$, $R^9$, $R^{10}$ and $R^{11}$, respectively or to groups $R^8$, $R^9$, $R^{10}$ and $R^{11}$, respectively protected with protective group such as to form of the following groups: OH, formate, benzoyl formate, optionally substituted acetate such as chloroacetate, dichloroacetate, trichloroacetate, trifluoroacetate, methoxyacetate, phenoxyacetate, phenylacetate, 4-penenoate, 4-oxopentanoate, benzoate, 4-phenylbenzoate, 4-bromobenzoate, 4-nitrobenzoate, picolinate, nicotinate, propanoate, 2-(azidomethyl)benzoate, 4-azidobutyrate, 2-iodobenzoate, 2-(allyloxy)phenylacetate, 4-benzyloxybutyrate, 4-nitro-4methylpentanoate, 2(chloroacetoxymethyl) benzoate, 4-(methylthiomethoxy)butyrate, 4-trialkylsiloxybutyrate, 2-formylbenzenesulfonate, tosylate, allylsulfonate, isobutyrate, 2-chlorobenzoate, 2-trifluoromethylsulfonate, isobutyrate, or carbonates such as methoxymethyl, ethyl, optionally substituted ethyl such as bromoethyl, 2-(methylthiomethoxy)ethyl, 2,2,2-trichloroethyl, 2-(dimethylsilyl) ethyl, 2-(dimethyl(2-naphtylmethyl)silyl)ethyl, 2-(phenylsulfonyl)ethyl, isobutyl, t-butyl, vinyl, allyl, propargyl, 4-chlorophenyl, 4-nitrophenyl, benzyl, 2-nitrobenzyl, 4-nitrobenzyl, 2-(4-nitrophenyl)ethyl, 2-(2,4-dinitrophenyl) ethyl, 2-(2-nitrophenyl)propyl, 2-cyano-1-phenylethyl, phenacetyl and S-benzyl thiocarbonate.

β-D-glucuronolactone (0.1 mol) of was dissolved in MeOH (100 mL) containing 0.15 g (2.77 mmol) of sodium methylate. The suspension was stirred for 1 h at ambient temperature finally turning into brownish syrup. Acetic acid anhydride (70 mL, 0.74 mol) and perchloric acid (0.3 mL, 5.0 mmol) were added slowly and the reaction mixture stirred at ambient temperature. After 4 h methanol (100 mL) and ether/petrolether (300 mL) were added and the filtrate was suction-filtered off. After drying in vacuo colorless product was obtained (20.5 g, 54.5% yield). LRMS, ESI: m/z 394.0 [M+NH$_4$]$^+$.

(2S,3S,4S,5R,6R)-6-(2-methoxy-2-oxoethyl)tetrahydro-2H-pyran-2,3,4,5-tetrayl tetraacetate (1.0 g, 2.66 mmol) was dissolved in dry dichloromethane (30 mL) and titanium tetrabromide (1.17, 3.19 mmol) was added dropwise. After 24h under stirring at ambient temperature the reaction mixture was diluted with dichloromethane (70 mL) and washed with water (3×20 mL) and saturated solution of sodium hydrogencarbonate (20 mL). The organic phase was dried with sodium sulfate and the solvent evaporated in vacuo yielding yellow oil. The crude product was dissolved in dry acetonitrile (100 mL). Silver oxide (712 mg, 3.08 mmol) and optionally substituted-4-hydroxyphenol (2.40 mmol) were added and the resulting yellow-green suspension stirred at ambient temperature. After 4h the reaction was stopped and the solvent evaporated. The crude product was purified by Flash chromatography using hexane/ethyl acetate as mobile phase. Colourless oil which slowly crystallized was obtained (565 mg, 44.0%). LRMS, ESI: m/z 500.8 [M+NH$_4$]$^+$.

(2S,3S,4S,5R,6R)-2-(4-(hydroxymethyl)-R5,R6-phenoxy)-6-(2-methoxy-2-oxoethyl) tetrahydro-2H-pyran-3,4,5-triyl triacetate (2S,3S,4S,5R,6R)-2-(4-formyl-SUBSTITUTED-phenoxy)-6-(2-methoxy-2-oxoethyl) tetrahydro-2H-pyran-3,4,5-triyl triacetate (500 mg, 1.03 mmol) was dissolved in dichloromethane (20 mL) and methanol (20 mL) and cooled to 0° C. on ice-bath. Sodium borohydride (65 mg, 1.50 mmol) was added and stirred. After 30 min TLC indicated complete conversion and saturated solution of ammonium sulphate (40 mL) was added to quench the reaction. The product was extracted with dichloromethane (3×30 mL), the organic phase dried with sodium sulphate. After solvent evaporation colourless solid was obtained which was purified by Flash chromatography using dichloromethane/methanol gradient yielding colourless product.

(2S,3S,4S,5R,6R)-2-(4-(hydroxymethyl)-R5,R6-phenoxy)-6-(2-methoxy-2-oxoethyl) tetrahydro-2H-pyran-3,4,5-triyl triacetate (41.2 µmol) was dissolved in a mixture of DMF (1.0 mL) and acetonitrile (3.0 mL) containing triethylamine (11.4 µL). The reaction mixture was cooled to 0° C. and disuccinimidyl carbonate (15.8 mg, 61.8 µmol) was added. After 1 h ester of 5-aminolevulinic acid hydrochloride (82.4 µmol) was added followed immediately by triethylamine (11.4 µL). The solvents were evaporated after 2h and the product extracted with dichloromethane from the water phase acidified to pH=5.0 with diluted HCl. The organic phase was washed with brine (5 mL) and dried over sodium sulphate. Crude product was purified by Flash chromatography using dichloromethane methanol gradient giving colorless product.

5-((((R5,R6-4-(((2S,SR,4S,5R,6R)-3,4,5-triacetoxy-6-(2-methoxy-2-oxoethyl)tetrahydro-2H-pyran-2-yl)oxy)benzyl)oxy)carbonyl)amino)-4-oxopentanoic acid (15.6 µmol) was dissolved in a mixture MeOH (5.0 mL) and 1M sodium hydroxide (5.0 mL) and stirred overnight at ambient temperature. The reaction mixture was neutralized by acetic acid and purified by reverse-phase HPLC using a H$_2$O (0.0025% TFA) and acetonitrile (0.0025%) gradient. The fractions containing the product (9) were freeze-dried yielding a fully deprotected colourless product.

In particular, compounds of Formula (IB2g) can be synthesized as described under Scheme 11 below Scheme 11

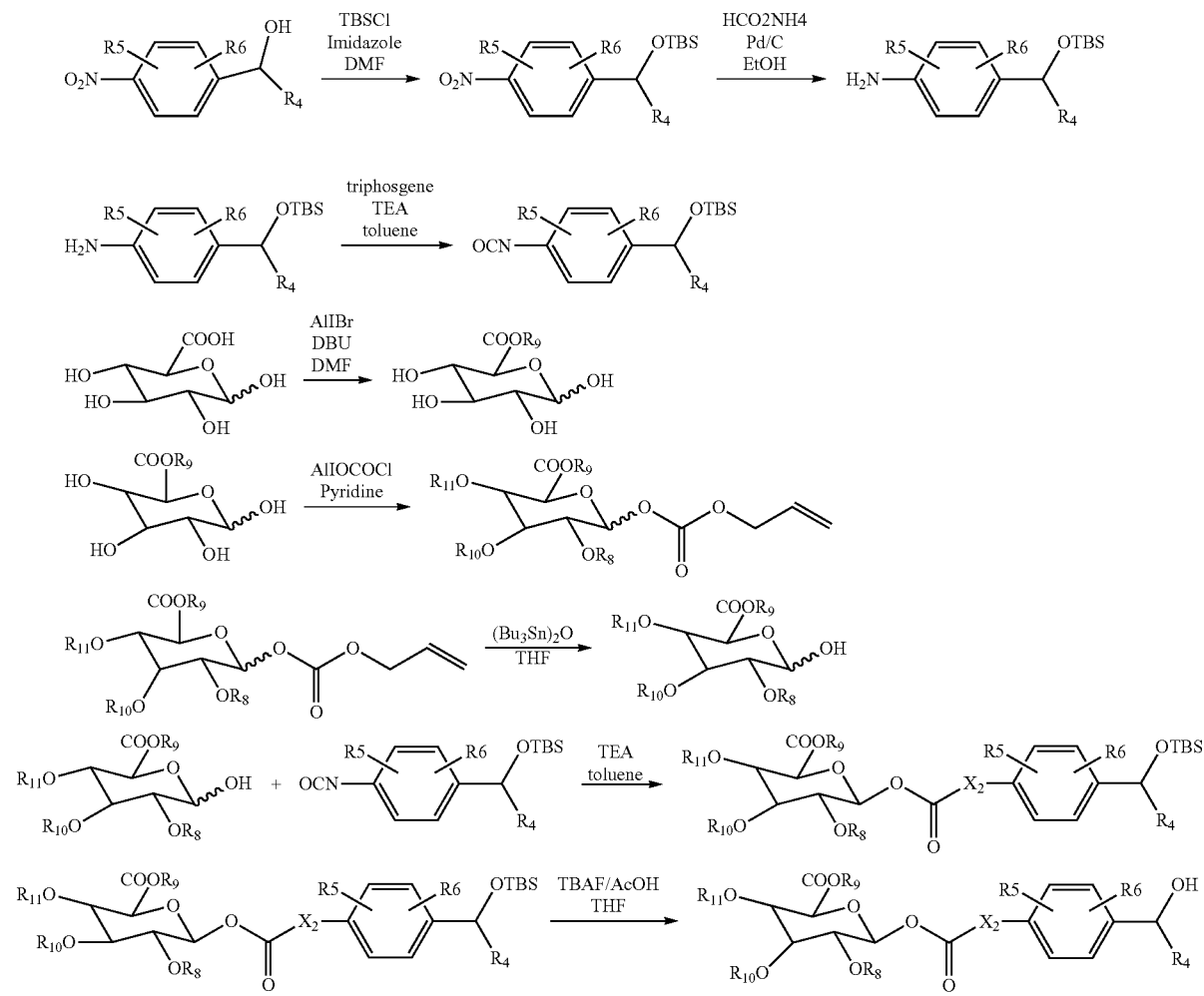

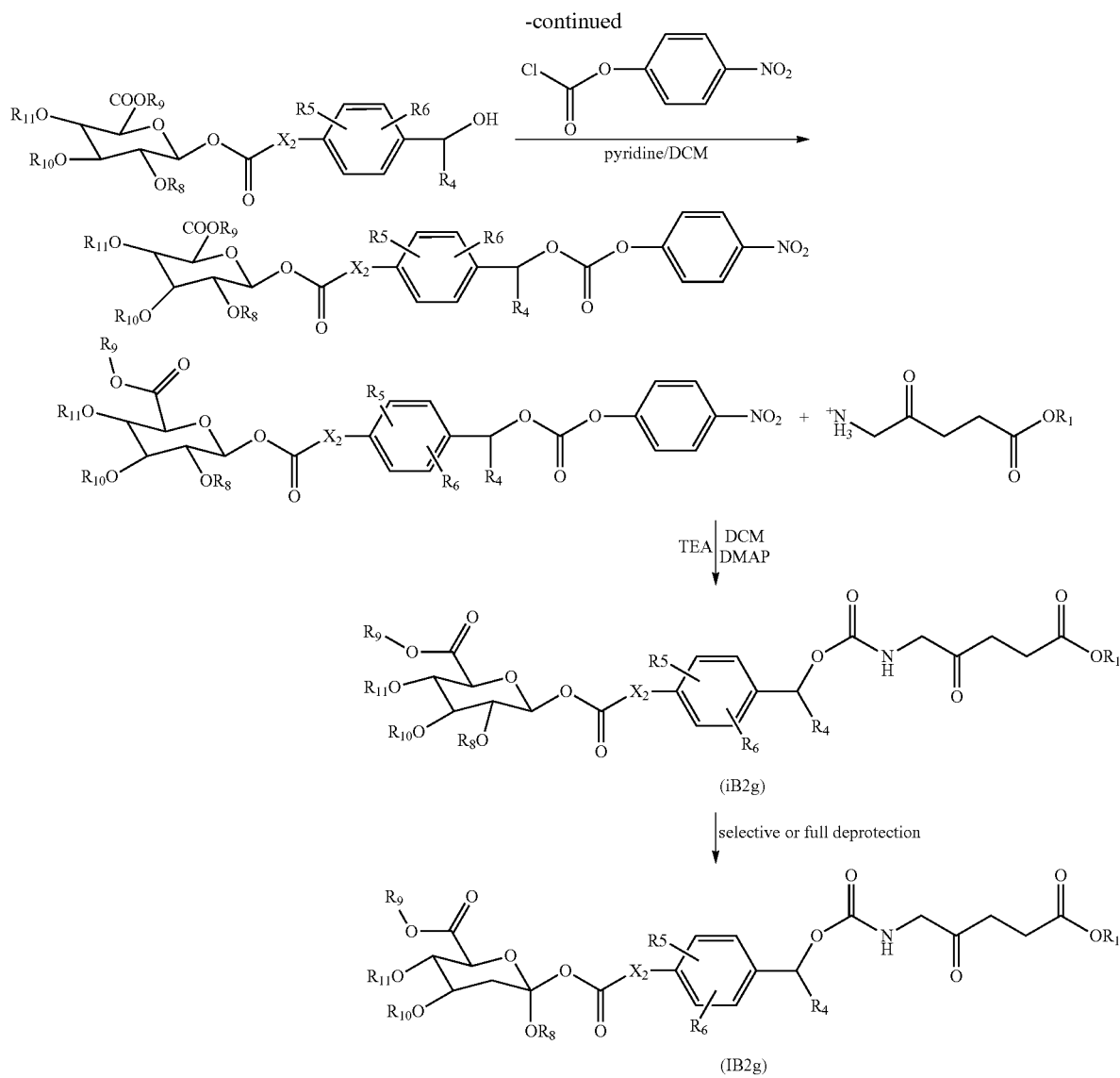

(iB2g)

(IB2g)

tert-Butyldimethyl-(4-nitrobenzyloxy)silane. To a solution of R2,R3-4-nitrobenzylic alcohol 5 (5 g, 0.032 mol) and imidazole (4.67 g, 0.068 mol) in anhydrous DMF (35 mL) was added tert-butyldimethylsilyl chloride (4.8 g, 0.032 mol) in small portions. After stirring for 2 h at room temperature, the mixture was diluted with EtOAc (250 mL), washed with water (6×70 mL), dried over MgSO4, and evaporated. The crude compound was purified over silica gel (eluent: cyclohexane/EtOAc 8/2). The product was isolated as an oil.

Tert-butyldimethyl(4-aminobenzyloxy)silane

Pd/C (10%, 2.5 g) and ammonium formate (8.6 g) were added to a solution of the nitro derivative 6 (8.3 g, 0.031 mol) in absolute ethanol (150 mL). After the solution was stirred for 5 h at room temperature, the catalyst was eliminated by filtration over Celite 545. The filtrate was evaporated and taken up in EtOAc (200 mL), washed with water (200 mL), dried over MgSO4, and evaporated to dryness. The oil was chromatographed over silica gel (eluent: cyclohexane/EtOAc 8/2) giving the desired product as oil.

Tert-Butyldimethyl(4-isocyanatobenzyloxy)silane

To a solution of the tert-butyldimethyl(4-aminobenzyloxy)silane compound (1.46 g, 6.1 mmol) and triethylamine (0.90 mL, 6.3 mmol) in freshly distilled toluene (40 mL) heated at 70° C. was added triphosgene (0.73 g, 2.4 mmol, 0.4 equiv). The solution became yellow with formation of a precipitate (triethylammonium salts). The mixture was heated for 3 h at 70° C. After filtration, washing with toluene, and evaporation, isocyanate product was obtained and directly used for the converging next step.

Allyl D-Glucuronate is synthesized according to Alaoui et al. 2006, *J. Org. Chem.*, 71, 9628-9636.

25 DBU (17.0 mL, 0.11 mol) was added dropwise to a solution of D-glucuronic acid (20 g, 0.103 mol) in DMF (200 mL). After the solution was stirred for 15 min at room temperature, 11 mL (0.12 mmol) of allyl bromide was added dropwise, and the mixture was stirred overnight. After evaporation, the residue was purified over silica gel with acetone as eluent. Product was (19.2 g, 79%) was isolated as a colourless oil.

Allyl 1.2.3.4-Tetra-(O-allyloxycarbonyl)-D-glucuronate

Allyl D-Glucuronate (9 g, 0.038 mol) was dissolved in anhydrous pyridine (100 mL). Allyl chloroformate (122 mL) was added dropwise in 15 min at 0° C. releasing gas. The solution turned brown. After 24 h under stirring, pyridine (30 mL) was added, and the mixture was stirred for another 24 h. The residue was then diluted in dichloromethane (250 mL) and washed twice with water, then three times with a saturated solution of copper sulfate. The last washing with water, drying over MgSO4, and evaporation gave a brown oil that was purified over silica gel (eluent: CH2Cl2/acetone 98/2) yielding colourless oil.

Allyl 2.3.4-tri-(O-Allyloxycarbonyl)-D-glucuronate

Bis(trin-butyltin) oxide (5.35 mL, 0.01 mol) was added to a solution (6 g, 0.01 mol) of the allyl 1.2.3.4-Tetra-(O-allyloxycarbonyl)-D-glucuronate in THF (240 mL), and the mixture was heated to reflux for 6 h. After evaporation of the solvent, the residue was chromatographed twice over silica gel (eluents: first elution CH2Cl2/acetone 96/4; second elution CH2-Cl2/acetone 95/5) to remove the tin derivatives, leading to product.

N-[4-(tert-Butyldimethylsilanyloxymethyl)phenyl]-O-[2,3,4-tri-(O-allyloxycarbonyl) allylester-β-D-glucopyranosyl]carbamate To a solution of Allyl 2.3.4-tri-(O-Allyloxycarbonyl)-D-glucuronate (1.8 g, 3.70 mmol) in freshly distilled toluene (100 mL) was added triethylamine (0.52 mL, 3.70 mmol) dropwise at 0° C. under argon, then tert-Butyldimethyl(4-isocyanatobenzyloxy)silane (1.26 g, 4.81 mmol) in toluene (10 mL), and the mixture was stirred for 1.5 h at 0° C. After evaporation, the residue was chromatographed over silica gel (eluent: CH2Cl2/acetone 99/1). The coupling product was isolated as an oil

N-[4-(Hydroxymethyl)phenyl]-O-[2,3,4-tri(O-allyloxycarbonyl)allylester-β-D-gluco pyranosyl]carbamate N-[4-(tert-Butyldimethylsilanyloxymethyl)phenyl]-O-[2,3,4-tri-(O-allyloxycarbonyl) allylester-β-D-glucopyranosyl]carbamate (800 mg, 1.067 mmol) and glacial acetic acid (80 μL, 1.387 mmol, 1.3 equiv) were dissolved in anhydrous THF (50 mL) at 0° C. TBAF (1 M, 420 μL, 1.387 mmol) in THF was added dropwise. After the solution was stirred for 18 h at room temperature, an additional 0.2 equiv of acetic acid and TBAF was added and the stirring was continued for 2 h. After cooling at 0° C., the mixture was diluted in dichloromethane and washed with a NaHCO3 saturated solution, then with water. The organic phase was dried over MgSO4 and evaporated to dryness. After purification over silica gel (eluent: CH2Cl2/acetone 92/8) the product was obtained as a lacquer.

O-[[N-[2,3,4-Tri(O-allyloxycarbonyl)allylester-β-D-glucopyranosyl]carbamoyl-4-oxy] benzyloxycarbonyl]-4-nitrophenol At 0° C., anhydrous pyridine (36 μL, 0.44 mmol) was added to a solution of compound 10 (140 mg, 0.22 mmol) in anhydrous dicholomethane (5 mL). Then, 4-nitrophenyl chloroformate (89 mg, 0.44 mmol, 2 equiv) was added and the mixture was stirred for 2 h at 0° C. After evaporation, the residue was chromatographed over silica gel (eluent: CH2Cl2/acetone 99/1), giving the product as a white lacquer.

allyl(2S,3S,4R,5R,6S)-3,4,5-triallyoxycarbonyl-6-(((4-(((((5-alkyloxy-2,5-dioxopentyl) carbamoyl)oxy) methyl)phenyl)carbamoyl)oxy)tetrahydro-2H-pyran-2-carboxylate 4-Nitrophenyl carbonate O-[[N-[2,3,4-Tri(O-allyloxycarbonyl)allylester-β-D-gluco pyranosyl]carbamoyl-4-oxy] benzyloxycarbonyl]-4-nitrophenol (43 mg, 0.053 mmol) and R1-ester of amino levulinic acid (32 mg, 0.078 mmol) were dissolved in freshly distilled dichloromethane (7 mL). Then, DMAP (9.8 mg, 0.080 mmol) was added under argon and the mixture was stirred for 24 h at room temperature. After evaporation, the compound obtained was purified over silica gel (CH2Cl2/acetone 9:1), giving the coupled product as a white solid.

allyl(2S,3S,4R,5R,6S)-3,4,5-triallyoxycarbonyl-6-(((4-(((((5-alkyloxy-2,5-dioxopentyl) carbamoyl)oxy)methyl) phenyl)carbamoyl)oxy)tetrahydro-2H-pyran-2-carboxylate was selectively or full deprotected using standard methods for functional group deprotection yielding final products of the IB2g class.

According to a particular embodiment, when R3 and/or R2 are H, compounds of the inventions are obtained in the form of a salt.

According to a particular embodiment, salts of compounds of the invention comprise Li, Na, K, Rb. Cs, Ca, Mg, Sr, Ba, Me3N, Et3N, Pr3N, Et2NisoPr and the like.

According to a particular embodiment, pharmaceutically acceptable salt include Na, K, Ca, Mg, Al, Zn, Tris, procaine, lysine, preferably Na, K, Ca or Mg.

According to a particular embodiment, is provided intermediates of Formula (iB1a1):

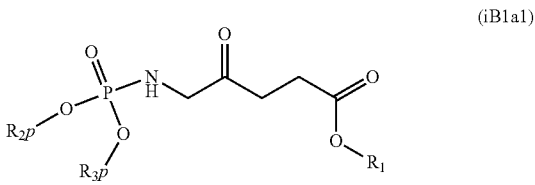

(iB1a1)

Wherein R1, R2p and R3p are as defined in the present description.

According to a particular embodiment, is provided intermediates of Formula (iB1a2).

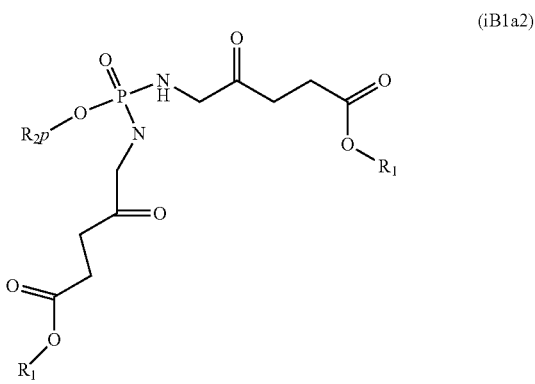

(iB1a2)

Wherein R1 and R2p are as defined in the present description.

According to a particular embodiment, is provided intermediates of Formula (iB1b).

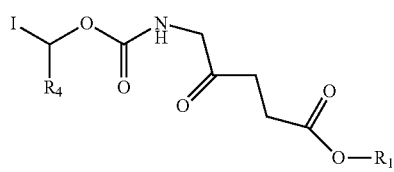
(iB1c)

Wherein R1 and R4 are is as defined in the present description.

According to a particular embodiment, is provided intermediates of Formula (iiB1b).

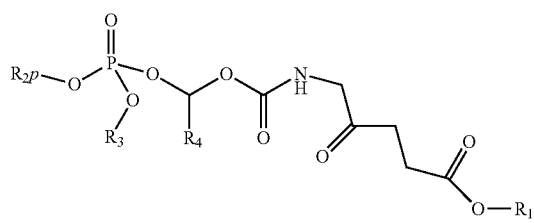
(iiB1b)

Wherein R1, R4 and R2p are as defined in the present description.

According to a particular embodiment, is provided intermediates of Formula (iB1c).

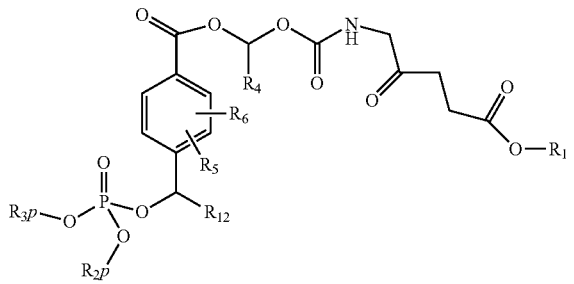
(iB1c)

Wherein R1, R4, R5, R6, R12 R2p and R3p are as defined in the present description.

According to a particular embodiment, is provided intermediates of Formula (iB1d).

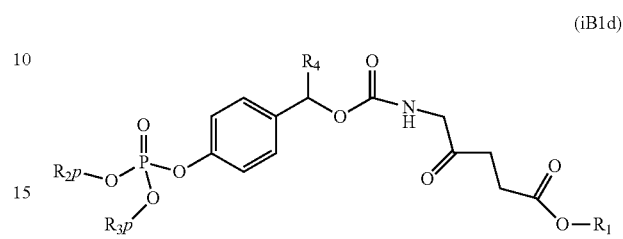
(iB1d)

Wherein R1, R4, R2p and R3p are as defined in the present description.

According to a particular embodiment, is provided intermediates of Formula (iB2d).

According to a particular embodiment, is provided intermediates of Formula (iB2d).

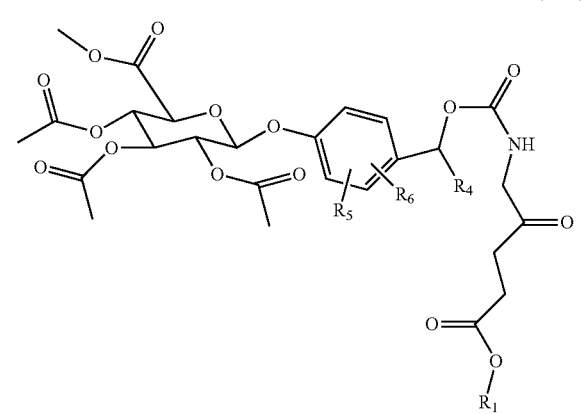
(iB2d)

Wherein R1, R4, R5 and R6 are as defined in the present description.

According to a particular embodiment, is provided intermediates of Formula (iB2g).

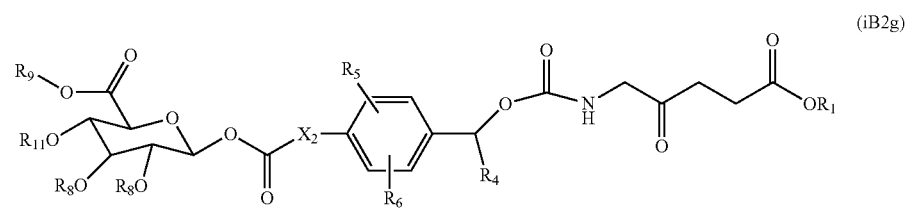
(iB2g)

Wherein X2, R1, R4, R5, R6 and R9 are as defined in the present description and R8, R10 and R11 are appropriate protective groups for hydroxyl group such as described above.

According to a particular embodiment, is provided a process for the preparation of compounds of Formula (I) comprising a step of reacting an intermediate compound according to the invention as described herein in any one of the reaction process to lead to a compound of Formula (I).

Particles

According to a further aspect, are provided particles made of at least one 5-ALA compounds of the invention.

According to one aspect, some compounds of the invention form particles (nanoassemblies) spontaneously in aqueous solution.

The control of such particle formation can be readily controlled by one of ordinary skill in the art using routine experimentation such as SEM, Transmission electron microscopy (TEM), Atomic force microscopy (AFM), laser diffractometry, and photon correlation spectroscopy and optimized by the choice of lipidic group as $R^2$ for example.

According to another further aspect, the invention provides a particle or a formulation thereof comprising a 5-ALA derivative of Formula (I) wherein $R^2$ is a lipid group, in particular a squalene group.

According to another further aspect, the invention provides a particle or a formulation thereof comprising a 5-ALA derivative selected from the following group: hexyl-((hydroxy(((4E,8E,12E,16E)-4,8,13,17,21-pentamethyldocosa-4,8,12,16,20-pentaen-1-yl)oxy)phosphoryl) amino)-4-oxopentanoate; and Bis-hexyl 5-((hydroxyl (((4E,8E,12E,16E)-4,8,13,17,21-pentamethyldocosa-4,8,12,16,20-pentaen-1-yl) oxy)phosphoryl)bis-amino)-4-oxopentanoate.

Particles according to the invention include micro or nanoparticles having a substantially spherical (i.e. particles generally appearing to be spherical) or non-spherical configuration. For instance, substantially spherical particles, upon swelling or shrinkage, may adopt a non-spherical configuration.

According to another further aspect, is provided a particle according to the invention, wherein the particle has a diameter from about 1 nm to about 10 μm, typically a diameter between 20 nanometers and 500 nanometers.

According to another further aspect, is provided a particle according to the invention for use as a medicament.

According to another further aspect, is provided a particle according to the invention for use in the photodiagnostic imaging (e.g. by fluorescence photodetection) of cancer.

In a particular aspect, the particles may present controlled release properties, e.g., may be capable of delivering an amount of 5-ALA to a patient, e.g., to specific site in a patient, over an extended period of time, e.g. over 24 hours or more. For example, in contrast to systemic delivery of known 5-ALA esters, the systemic delivery of particles disclosed herein may substantially prevent the agent from killing healthy cells or to induce severe side effects in a subject. Additionally, disclosed particles may allow the induction of higher amounts of photoactive porphyrins and/ or the long lasting of induced high photoactive porphyrin contents (as compared to an effective amount of known 5-ALA esters). Those properties confer to those particles and formulations thereof reduced undesirable side effects and increased efficacy as compared to agents commonly used in traditional chemotherapy, thus an increased therapeutic index.

Formulations According to the Invention

Compounds disclosed herein may be combined with one or more pharmaceutical acceptable carrier(s) to form a pharmaceutical composition.

According to an embodiment, is provided a pharmaceutical formulation, said formulation comprising at least one compound according to the invention and at least one pharmaceutically acceptable carrier.

According to another embodiment, is provided a compound, a particle or a formulation thereof obtainable by a process or a method according to the invention.

According to a further embodiment, the invention provides a pharmaceutical formulation for systemic administration in a mammal, typically a human.

According to a further embodiment, the invention provides a pharmaceutical formulation suitable for injection in humans (e.g. intravenous).

According to another further embodiment, the invention provides a formulation according to the invention for use as a medicament.

According to another further embodiment, the invention provides a kit comprising in one or more container(s) a formulation according to the invention together with instruction of use of said formulation.

According to a further aspect, the invention provides a kit for use in a method of treating or reducing a cancer comprising: a) a first container containing a formulation according to the invention and optionally b) one or more chelating agents contained either within said first container or in a second container. According to a further aspect, the invention provides a photodynamic therapy kit further comprising a light emitting device for irradiation of light of wavelength of about 300 nm to about 800 nm, typically about 380 nm to about 660 nm.

According to a further aspect, the invention provides a kit for use in a method of detection of a cancer cell comprising: a) a first container containing a formulation according to the invention and optionally b) one or more chelating agents contained either within said first container or in a second container. According to a further aspect, the invention provides a photodetection kit further comprising a light emitting device for irradiation of light of wavelength of about 300 nm to about 800 nm, typically about 380 nm to about 660 nm and a second device capable for visualizing the emitted fluorescence (typically from about 600 to about 750 nm).

According to another further embodiment, the invention provides a formulation according to the invention for the treatment of cancers (e.g. by photodynamic therapy).

According to another further embodiment, the invention provides a formulation according to the invention for the diagnosis of a cancer cell (e.g. by fluorescence photodetection).

According to another further embodiment, the invention provides a formulation according to the invention further comprising a co-agent useful in the treatment of cancer, such as substances useful for treating, stabilizing, preventing, and/or delaying cancer.

Particles according to the invention may be administered as a pharmaceutical formulation which can contain one or more particles according to the invention and a pharmaceutically acceptable carrier, in any form described herein.

In a particular aspect, a formulation of the invention is adapted for delivery by repeated administration.

In another aspect, the pharmaceutical compositions may be placed separately into the form of unit dosages.

As it would be appreciated by one skilled person in this art, the carriers may be chosen based on the route of administration as described below, the location of the target tissue, the drug being delivered, the time course of delivery of the drug, etc.

Formulations of this invention may further comprise one or more pharmaceutically acceptable additional ingredient(s) such as alum, stabilizers, antimicrobial agents, buffers, coloring agents, flavoring agents, adjuvants, and the like.

Formulations of the invention, together with a conventionally employed adjuvant, carrier, diluent or excipient may be employed as liquids such as solutions, suspensions, emulsions, elixirs, or capsules filled with the same, or in the form of sterile injectable solutions. Compositions of this invention may also be formulated for parenteral administration including, but not limited to, by injection or continuous infusion. Such liquid preparations may contain additives including, but not limited to, dispersing or wetting agents, suspending agents, emulsifying agents, non-aqueous vehicles and preservatives. Injectable preparations may be prepared for example as sterile injectable aqueous or oleaginous suspensions, or emulsion in a nontoxic parenterally acceptable diluent or solvent. Among the acceptable vehicles and solvents that may be employed are water, Ringer's solution, and isotonic sodium chloride solution or other injectable carriers known in the art. The injectable formulations can be sterilized, for example, by incorporating sterilizing agents in the form of sterile solid compositions which can be dissolved or dispersed in sterile water or other sterile injectable medium prior to use. The compositions may also be provided in a powder form for reconstitution with a suitable vehicle including, but not limited to, sterile, pyrogen-free water.

Suspending agents include, but are not limited to, sorbitol syrup, methyl cellulose, glucose/sugar syrup, gelatin, hydroxyethyl cellulose, carboxymethyl cellulose, aluminum stearate gel, and hydrogenated edible fats. Emulsifying agents include, but are not limited to, lecithin, sorbitan monooleate, and acacia. Preservatives include, but are not limited to, methyl or propyl p-hydroxybenzoate and sorbic acid. Dispersing or wetting agents include but are not limited to poly(ethylene glycol), glycerol, bovine serum albumin, Tween®, Span®.

Compositions of this invention may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

Compositions of this invention may also be formulated for inhalation, which may be in a form including, but not limited to, a solution, suspension, or emulsion that may be administered as a dry powder or in the form of an aerosol using a propellant, such as an inhaler (e.g. Turbohaler®, Spinhaler®, Diskhaler®, Easyhaler®) as described in *Pharmazeutische Technologie*, 9$^{th}$ Edition, 2000, Dt. Apotheker Verlag, Stuttgart. Typically, the aerosol is delivered to the airways from of the patient.

Compositions of this invention may also be formulated as transdermal formulations comprising aqueous or non-aqueous vehicles including, but not limited to, creams, ointments, lotions, pastes, medicated plaster, patch, or membrane.

Compositions of this invention may also be formulated for oral administration. Solid dosage forms for oral administration include capsules, tablets, pills, powders, and granules. In such solid dosage forms, the particles of the invention are mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethyl cellulose, alginates, gelatin, polyvinylpyrrolidinone, sucrose, and acacia, gelatine (c) humectants such as glycerol, (d) disintegrating agents such as agar-agar, calcium carbonate, potato or tapioca starch, alginic acid, certain silicates, and sodium carbonate, polyvinylpyrrolidone (e) solution retarding agents such as paraffin, ethyl cellulose, polyacrylate/methacrylate (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

In an exemplary embodiment, a pharmaceutical composition according to the invention includes a plurality of particles according to the invention and a pharmaceutically acceptable excipient.

In one embodiment, is provided a composition according to the invention suitable for freezing wherein the composition includes compounds or particles disclosed herein and a solution suitable for freezing, e.g. a cryoprotectant to prevent the compounds or particles from aggregating upon freezing such as a sucrose, trehalose, mannitol, glucose, lactose, sorbitol, polyvinylpyrrolidone, glycerol, glycine, gelatine, maltose or fructose solution or a mixtures thereof.

In another embodiment, is provided a composition suitable for use as a precursor for preparing tablets or preparation for compositions for inhalation.

In another embodiment, is provided a composition suitable for use in the photodiagnostic imaging of cancer (e.g. by fluorescence photodetection).

Further materials as well as formulation processing techniques and the like are set out in *Part 5 of Part 5 of Remington's "The Science and Practice of Pharmacy", 22nd Edition, 2012, University of the Sciences in Philadelphia*, which is incorporated herein by reference.

Mode of Administration

Formulations of this invention may be administered in any manner including orally, parenterally, vaginally, rectally, intranasally, intraarticularily, intravesically, intraauricularly, topically or by inhalation or combinations thereof.

In a particular embodiment, the particles of the present invention are administered to a subject in need thereof systemically, e.g. by i.v. infusion, injection, or parenteral administration.

In a particular embodiment, the particles of the present invention are orally administered to a subject in need thereof (e.g. as capsule, tablet, or suspension).

Parenteral administration includes, but is not limited to, intravenous, intra-arterial, intra-peritoneal, subcutaneous and intramuscular. According to a particular aspect, the compositions of this invention are administered in the form of an implant, which allows slow release of the compositions as well as a slow controlled i.v. infusion.

Uses and Methods According to the Invention

Photodynamic therapy based on the systemic administration of a compound according to the invention and formulations thereof, for the treatment of cancers uses the body's own biosynthetic ability to form the endogenous intracellular chromophore protoporphyrin IX (PpIX). In Photodynamic diagnosis (PDD), the strong fluorescence of this chromophore is induced by an excitation signal at 380-660 nm which yields a strong emission in the range 600-750 nm, enabling detection of the tissue in which PpIX is accumulated.

According to one aspect, the invention provides a method of treating or repressing a cancer, said method comprising administering in a subject in need thereof a therapeutically effective amount of a pharmaceutical formulation according to the invention and exposing cancer cells to light. Typically, in a method of treatment according to the invention, protoporphyrin IX intracellular accumulation into cancer cells is triggered by the administration of a formulation according to the invention and cancer cells are exposed to a light having a suitable wavelength (e.g. white light, for example light in the wavelength region 300-800 nm, typically light in the wavelength region 380-660 nm) in order to activate protoporphyrin IX and convert it into a cytotoxic form thereof.

According to another aspect, the invention provides a method of diagnosis of a cancer cell, said method comprising the following steps:
 a) administering in a subject in need thereof a detectably effective amount of a pharmaceutical formulation according to the invention;
 b) exposing the site of investigation of the subject's body to light.

Typically, in a method of diagnosis according to the invention, intracellular protoporfyrin IX accumulation at the site of investigation is triggered by the administration of a formulation according to the invention and the site of investigation of the subject's body is then exposed to a light having a suitable wavelength to excite the fluorescence of protoporphyrin IX (e.g. light in the wavelength region 300-800 nm, typically blue light in the wavelength region 350-440 nm) and measure the triggered fluorescence (e.g. in the wavelength region 550-750 nm) which may be used to visualize the size, extent and situation of an abnormality or disorder.

According to a further embodiment, the method of diagnosis according to the invention comprises the further steps of:
 c) ascertaining the level of fluorescence induced under step b);
 d) comparing the level of fluorescence measured under step c) to control levels.

According to a further embodiment, the method of diagnosis according to the invention wherein the level of fluorescence ascertained under step c) is measured at a wavelength equal to or between about 620 and about 720 nm.

The abnormality or disorder thus identified or confirmed at the site of investigation may then be treated through alternative therapeutic techniques e.g. surgical or chemical treatment, or by a method of treatment of the invention by continued build-up of fluorescence or through further application of formulations of the invention at the appropriate site. It will be appreciated that diagnostic techniques may require lower levels of fluorescence for visualization than used in therapeutic treatments.

Methods for irradiation of different areas of the body, e.g. by lamps or lasers are well known in the art (e.g. Van den Bergh, 1986, *Chemistry in Britain*, p. 430-439). For inaccessible regions this may conveniently be achieved using optical fibres as described in Hasselgren et al., 1990, *Applied Optics*, 29: 44481-44488.

According to a further aspect, the invention provides a method of treating or repressing a cancer or a method of diagnosis of a cancer cell, wherein cancer cells are only efficiently accessible systemically such as in the case of colon cancer, rectal cancer, breast cancer, mama carcinoma, lymphoma, brain cancer, ovarian cancer, non-small cell lung cancer, colorectal carcinoma, glioblastoma, gastric, bronchus cancer, pancreatic cancer, urinary bladder cancer, hepatic cancer, non-melanoma skin cancer, oesophageal cancer, oral cancer, duodenal cancer, cervix cancer, uterus cancer, kidney cancer and prostate cancer.

According to a further aspect of the invention, the invention provides a method of treating or repressing a cancer or a method of diagnosis of a cancer cell, wherein compounds, particles or formulations thereof according to the present invention are administered parenterally and then, between about 1 minute to about 48 hours, typically between about 30 minutes and about 24 hours after administration the cells/the site of investigation are then illuminated with visible light, typically in the region between about 350 and about 750 nm, allowing for said diagnosis or therapy.

According to a further aspect of the invention, the invention provides a method of treating or repress a cancer or a method of diagnosis of a cancer cell, wherein compounds, particles or formulations thereof according to the present invention are orally administered (e.g. as capsule or tablet).

According to a further aspect of the invention, is provided a use of a compound, a particle or formulations according to the invention for the treatment of a cancer.

According to a further aspect of the invention, is provided a use of a compound, a particle or a formulation according to the invention for the preparation of a pharmaceutical formulation for treatment of a cancer.

According to a further aspect of the invention, is provided a use of a compound, a particle or a formulation according to the invention for the diagnosis of a cancer cell.

According to a further aspect of the invention, is provided a use of a compound, a particle or a formulation according to the invention for the preparation of a pharmaceutical formulation for diagnosis of a cancer cell.

According to a further aspect, are provided uses and methods according to the invention wherein a pharmaceutical formulation according to the invention is to be systemically administered.

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

Combinations

According to one embodiment of the invention, the compound, particles and pharmaceutical formulations thereof can be administered alone or in combination with a co-agent useful in the treatment of cancer, in particular substances useful for treating, stabilizing, preventing, and/or delaying cancer such as substances used in conventional chemotherapy directed against solid tumors and for control of establishment of metastases or any other molecule that act by triggering programmed cell death e.g. for example a co-agent selected from angiogenesis inhibitors (e.g. anti-VEGF agents, anti-PDGF agents), immunotherapy agents (e.g. recombinant cytokines, interferones, interleukin, recombinant antibodies such as Herceptin®) and chemotherapeutic agents (e.g. cisplatin, paclitaxel, methotrexate, 5-fluoruracil, Gemcitabin, Vincristin, Vinblastin, Doxorubicin).

According to another aspect, the compounds, particles according to the invention and pharmaceutical formulations thereof be administered alone or in combination with a co-agent useful in improve the efficacy of PDT such as photosensitizing agents (e.g. psoralens, porphyrins such as Photofrin®, chlorins and the phthalocyanins) or with other active components which may enhance the photochemotherapeutic effect such as chelating agents (e.g. EDTA or desferrioxamine).

According to one embodiment of the invention, the compounds, particles according to the invention and pharmaceutical formulations thereof can be administered alone or in combination with a co-agent useful in the detection of a cancer cell, typically agents enhancing the detectivity of fluorescence such as Photofrin®.

According to one embodiment of the invention, the compounds, particles according to the invention and pharmaceutical formulations thereof can be administered in combination with a co-agent useful in the detection of a cancer cell, typically a metal ion such as $Mg^{2+}$, $Ca^{2+}$, $Gd^{3+}$, $Ga^{3+}$, and $Zn^{2+}$ or a radioisotope thereof useful in imaging techniques such as MRI (Magnetic Resonance Imaging), SPECT (Single-photon emission computed tomography), and X-ray imaging techniques as described. According to the invention, the metal ions or isotopes thereof can be administered in the form of salts such as nitrate, citrate, maltolate, bromide, sulfate, or phosphate salts.

According to one embodiment of the invention, the compounds, particles according to the invention and pharmaceutical formulations thereof can be administered in combination with a co-agent useful in the treatment a cancer cell, typically a metal ion such as $Mg^{2+}$, $Ca^{2+}$, $Gd^{3+}$, $Ga^{3+}$, and $Zn^{2+}$ or a radioisotope thereof.

According to a further embodiment, the compounds, particles according to the invention and pharmaceutical formulations thereof can be administered in combination with Gallium such combined regimen being useful in the detection and/or treatment of cancer based on the same principles as detection and/or treatment of cancer described for Gallium compounds (Chitambar et al., 2010, *Int. J. Environ. Res. Public Health*, 7, 2337-2361; Collery et al., 2002, *Critical Review in Oncology/Hematology*, 42, 283-296) but where imaging sensitivity and therapeutic efficacy benefit from the co-administration with particles of the invention.

The invention encompasses the administration of compounds, particles according to the invention or pharmaceutical formulations thereof, wherein the particles according to the invention or the pharmaceutical formulation thereof are administered to an individual prior to, simultaneously or sequentially with other therapeutic regimens or co-agents useful in the treatment of cancers or co-agents useful in the detection of a cancer cell (e.g. multiple drug regimens), in a therapeutically effective amount. Compounds, particles according to the invention or pharmaceutical formulations thereof, that are administered simultaneously with said co-agents can be administered in the same or different composition(s) and by the same or different route(s) of administration.

Patients

In an embodiment, patients according to the invention are patients suffering from a disease or disorder including any malignant, pre-malignant and non-malignant abnormalities responsive to photochemotherapy, including, but not limited to, tumors or other hyperproliferative conditions such as cancers, skin disorders such as psoriasis, skin cancer, or actinic keratosis, infectious diseases (e.g. viral, bacterial, fungal infections), inflammatory diseases like Morbus Crohn, arthritis and rheumatoid arthritis, Barrett's esophagus or arterial restenosis.

In a particular embodiment, patients according to the invention are suffering from a cancer. In another particular embodiment, patients according to the invention are suffering from bladder, kidney, colon, breast, brain, ovarian, skin, or prostate cancer.

In another particular embodiment, patients according to the invention are susceptible to suffer from a cancer or to present a cancer cell in their tissues.

References cited herein are hereby incorporated by reference in their entirety. The present invention is not to be limited in scope by the specific embodiments and drawings described herein, which are intended as single illustrations of individual aspects of the invention, and functionally equivalent methods and components are within the scope of the invention. The examples illustrating the invention are not intended to limit the scope of the invention in any way.

EXAMPLES

General Procedures & Conditions

The following studies are conducted to support stability, safety, efficiencies in in vivo releasing 5-ALA and efficiency in inducing porphyrins in cancer cells of the compounds and nanoparticles thereof according to the invention. Since systemic administration of known 5-ALA derivatives has shown to cause acute systemic toxicity, this study is of great importance for anticipating beneficial effects of compounds, particles and formulations thereof according to the invention in clinical use.

The following abbreviations refer respectively to the definitions below:

min (minute), ml (milliliter), mM (millimolar), nm (nanometers), DCM (dichloromethane), DMSO (Dimethyl sulfoxide), DPBS (Dulbecco's phosphate-buffered saline), NMR (Nuclear magnetic resonance), MTT ((3-(4,5-Dimethylthiazol-2-yl)-2,5-Diphenyltetrazolium Bromide), PDT (photodynamic therapy), TEA (triethylamine), THF (tetrahydrofurane), U (unit), DIPEA (diisopropylethylamine), DMAP (4-aminopyridine), TBAF (Tetra-n-butylammonium fluoride), AcOH (acetic acid), DBU (1,8-Diazabicyclo[5.4.0]undec-7-ene), DMF (dimethylformamide), Pd/C (palladium on charcoal), TBSCl (tert-Butyldimethylsilyl chloride).

Example 1

Preparation of Compounds of Formula (I)
According to Formula (IB1a1), wherein $R^2$ is Phenyl, $R^3$ is H and $R^1$ is Selected from Hexyl, Methyl and Benzyl, n is 0, Z is O and B is B1

Compounds were synthesized according to Scheme 5 above as detailed below.

Compound 1: Triethylammonium salt of hexyl 5-((hydroxy(phenoxy)phosphoryl)amino)-4-oxopentanoate (P1-ALA-Hex)

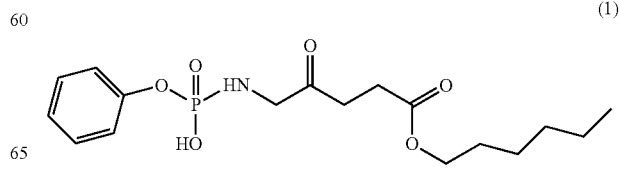

(1)

Phenyl dichlorophosphate (407 mg, 1.93 mmol) (Acros) was dissolved in dry THF (20 mL) and cooled to 0° C. on ice. Hexyl 5-amino-4-oxopentanoate was synthesized as described in Dabrowski et al., 2003, *Acta Poloniae Pharmaceutica*, 60(3), 219-224 (491 mg, 1.95 mmol) was added to the cooled solution followed immediately by dropwise addition of dry triethylamine (600 µL). The resulting suspension was stirred at 0° C. for 1 hour and then allowed to warm-up to ambient temperature. After 2h at ambient temperature the reaction mixture was quenched with water (5.0 g) and triethylamine (650 µL). After 30 min the solvents were evaporated and the crude product extracted with ethylacetate (3×30 mL) from water (30 mL). The organic phase was washed with brine and dried with sodium sulphate. The crude product was purified by Flash chromatography using DCM/MeOH+(1% TEA) gradient giving colourless oil (542 mg, 1.15 mmol, 57.8% yield). 1H NMR (300 MHz, CD3OD) δ 7.34-7.14 (m, 4H), 7.11-6.96 (m, 1H), 4.02 (t, J=6.6 Hz, 2H), 3.82 (d, J=8.3 Hz, 2H), 3.18 (q, J=7.3H, 6H), 2.73 (dd, J=7.2, 5.6 Hz, 2H), 2.53 (dd, J=7.2, 5.5 Hz, 2H), 1.67-1.48 (m, 2H), 1.31 (m, 17H), 0.96-0.84 (m, 3H). 13C NMR (75 MHz, CD3OD) δ 208.05 (d), 173.34, 153.34 (d), 129.12, 123.01, 120.66, 120.60, 64.66, 51.41, 48.77, 46.58, 33.94, 31.44, 28.51, 27.64, 25.52, 22.46, 13.30, 8.12. LRMS, ESI: m/z 370.4 [M−H]−, 741.5 [2M−H]−, 1112.7 [3M−H]−, 372.4 [M+H]+, 743.7 [2M+H]+, 1114.8 [3M+H]+.

Compound 2: Triethylammonium salt of methyl 5-((hydroxy(phenoxy)phosphoryl) amino)-4-oxopentanoate (1P1-ALA-Me)

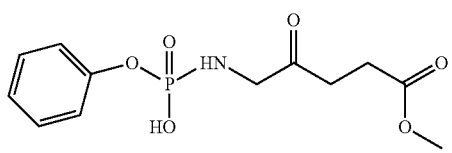

(2)

Compound 3: Triethylammonium salt of benzyl 5-((hydroxy(phenoxy)phosphoryl) amino)-4-oxopentanoate (1P1-ALA-Bn)

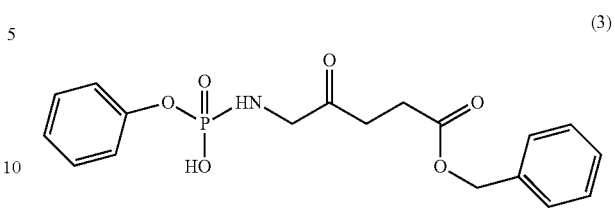

(3)

The compound was prepared using the same procedure as P1-ALA-Hex with benzyl 5-amino-4-oxopentanoate (synthesized as described in Dabrowski et al., 2003, supra) as starting material. Colourless oil (50.3% yield). 1H NMR (300 MHz, CDCl3) δ 7.33-7.04 (m, 9H), 6.89 (t, J=7.0 Hz, 1H), 4.97 (s, 2H), 3.73 (d, J=8.2 Hz, 2H), 2.92 (q, J=7.3 Hz, 4H), 2.49 (m, 4H), 1.20 (t, J=7.2, 9H). $^{13}$C NMR (75 MHz, CDCl3) δ 207.20 (d), 172.66, 153.62 (d), 153.53, 136.02, 129.29, 128.71, 128.37, 128.27, 122.85, 120.71 (d), 66.53, 52.28, 45.60, 34.27, 27.94, 8.69. LRMS, ESI: m/z 378.4 [M+H]+, 400.5 [M+Na]+, 755.5 [2M+H]+.

Example 2

Preparation of Compounds of Formula (I)
According to Formula (IB1a1), wherein $R^2$ is Squalene Alcohol, $R^3$ is H and $R^1$ is Hexyl, Z is O Compound was synthesized according to Scheme 5 above as detailed below.

Compound 4: Hexyl 5-((hydroxy(((4E,8E,12E, 16E)-4,8,13,17,21-pentamethyldocosa-4,8,12,16,20-pentaen-1-yl)oxy)phosphoryl)amino)-4-oxopentanoate (1P2-SQ-ALA-Hex))

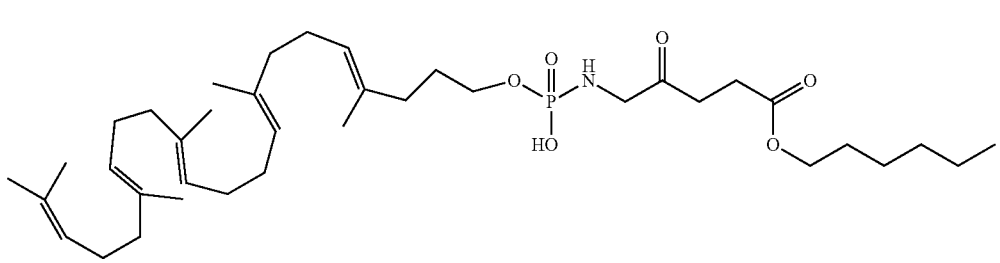

(4)

The compound was prepared using the same procedure as P1-ALA-Hex with methyl 5-amino-4-oxopentanoate (synthesized as described in Dabrowski et al., 2003, supra) as starting material. Colourless oil (39.6% yield). 1H NMR (300 MHz, CD3OD) δ 7.38-7.12 (m, 4H), 7.06 (m, 1H), 3.81 (d, J=8.7 Hz, 2H), 3.62 (s, 3H), 3.21-3.02 (m, 6H), 2.74 (dd, J=7.2, 5.6 Hz, 2H), 2.56 (dd, J=7.2, 5.6 Hz, 2H), 1.25 (t, J=7.3 Hz, 9H). 13C NMR (75 MHz, CD3OD) δ 207.25 (d), 173.64, 152.99 (d), 129.17, 123.30, 120.58, 120.52, 51.18, 46.31, 33.85, 27.36, 7.98. LRMS, ESI: m/z 300.4 [M−H]−, 601.2 [2M−H]−, 302.4 [M+H]+, 603.3 [2M+H]+.

Phosphoryl trichloride (Acros) (56 mg, 0.36 mmol) was dissolved in dioxane (10 mL). Squalene alcohol (synthesized as described in Ceruti et al., 1987, *Eur. J. Med. Chem.* 22, 199-208) 140 mg, 0.36 mmol) followed by dry triethylamine (50 µL, 0.36 mmol) were added and the resulting suspension stirred at ambient temperature. After 6 h hexyl 5-amino-4-oxopentanoate (synthesized as described in Dabrowski et al., 2003, supra) (100 mg, 0.40 mmol) was added followed by drop-wise addition of dry triethylamine (150 µL, 1.08 mmol) for 15 min. After additional 12h at room temperature the reaction mixture was quenched with water (3.0 mL). The solvents were evaporated after 1 h and the crude product purified by flash chromatography using DCM/MeOH+1% TEA gradient giving colourless oil (55 mg, 20.0% yield). $^1$H NMR (300 MHz, CDCl$_3$) δ 5.16-5.04 (m, 5H), 4.03 (t, J=6.8 Hz, 2H), 3.84 (m, 2H), 3.08 (q, J=7.3 Hz, 6H), 2.70 (dd, J=7.2, 6.5 Hz, 2H), 2.61 (d, J=7.2, 6.4 Hz, 2H), 2.08-1.91 (m, 22H), 1.70-1.53 (m, 22H), 1.37 (t, J=7.2, 9H), (1.32-1.22 (m, 8H), 0.93-0.82 (m, 3H). $^{13}$C NMR (75 MHz, CDCl$_3$) δ 207.45 (d), 191.21, 176.60, 153.53 (d), 135.46, 135.32, 135.10, 131.46, 124.61, 124.48, 124.29, 77.66, 77.24, 76.82, 65.25, 45.98, 40.09, 39.99, 39.95, 36.12, 31.72, 29.97, 28.77, 28.58, 27.93, 27.32, 26.98, 26.91, 25.93, 25.83, 22.78, 17.91, 16.34, 16.25, 16.22, 14.26, 8.84. LRMS, ESI: m/z 378.4 m/z 665.0 [M+H]$^+$, 1328.8 [2M+H]$^+$, 1992.8 [3M+H]$_+$.

Example 3

Preparation of Compounds of Formula (I) According to Formula (IB1a2), wherein R$^2$ is Phenyl, and R$^1$ and R1D are Hexyl, E is D2, n is 0, Z is O, q is 0

Compounds were synthesized according to Scheme 6 above as detailed below.

Compound 5: Bis(hexyl) 5-((hydroxy(phenoxy) phosphoryl)bis(amino)-4-oxopentanoate) (2P1-ALA-Hex)

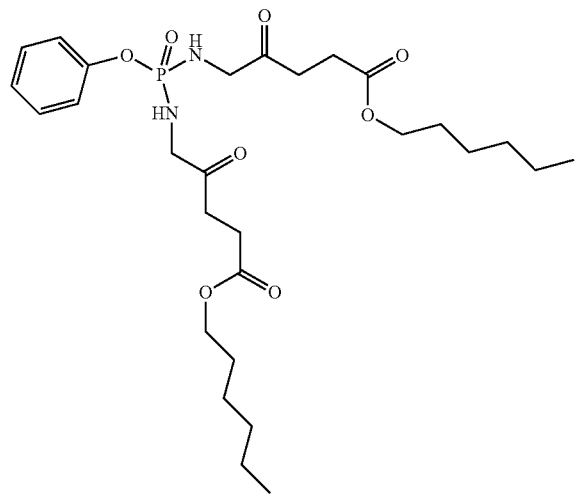

(5)

Phenyl dichlorophosphate (Acros) (208 mg, 0.98 mmol) was dissolved in dry THF (20 mL) and cooled to 0° C. on ice. Hexyl 5-amino-4-oxopentanoate (synthesized as described in Dabrowski et al., 2003, supra) (500 mg, 2.00 mmol) was added to the cooled solution followed immediately by slow dropwise addition of dry triethylamine (0.66 mL) over 1h. The resulting suspension was stirred at 0° C. for 2 hours and then allowed to warm-up to ambient temperature. After 12h at ambient temperature the solvents were evaporated and the crude product extracted with ethylacetate (3×30 mL) from water (30 mL). The organic phase was washed with brine and dried with sodium sulphate. The crude product was purified by Flash chromatography using DCM/MeOH gradient giving colourless oil (455 mg, 0.80 mmol, 81.6% yield). $^1$H NMR (300 MHz, CDCl$_3$) δ 7.36-7.09 (m, 5H), 4.10-4.01 (m, 4H), 3.98-3.91 (m, 4H), 3.08 (t, J=7.3 Hz 1H), 2.78 (t, J=7.3 Hz 1H), 2.73-2.56 (m, 4H), 1.68-1.51 (m, 4H), 1.46-1.19 (m, 12H), 0.94-0.81 (m, 6H). 13C NMR (75 MHz, CDCl3) δ 204.85 (d), 172.70, 129.93, 124.95, 120.58, 120.51, 65.29, 50.75, 50.72, 34.42, 31.62, 28.72, 28.11, 25.75, 22.75, 14.23. LRMS, ESI: m/z 569.5 [M+H]+, 587 [M+NH4]+.

Example 4

Preparation of Compounds of Formula (I) According to Formula (IB1a2), wherein R$^2$ is Squalene, and R$^1$ and R1D are Hexyl, n is 0, E is D2, q is 0 and Z is O Compounds were synthesized according to Scheme 6 above as detailed below.

Compound 6: Bis-hexyl 5-((hydroxy(((4E,8E,12E, 16E)-4,8,13,17,21-pentamethyldocosa-4,8,12,16,20-pentaen-1-yl)oxy)phosphoryl)bis-amino)-4-oxopentanoate (2P2-SQ-ALA-Hex)

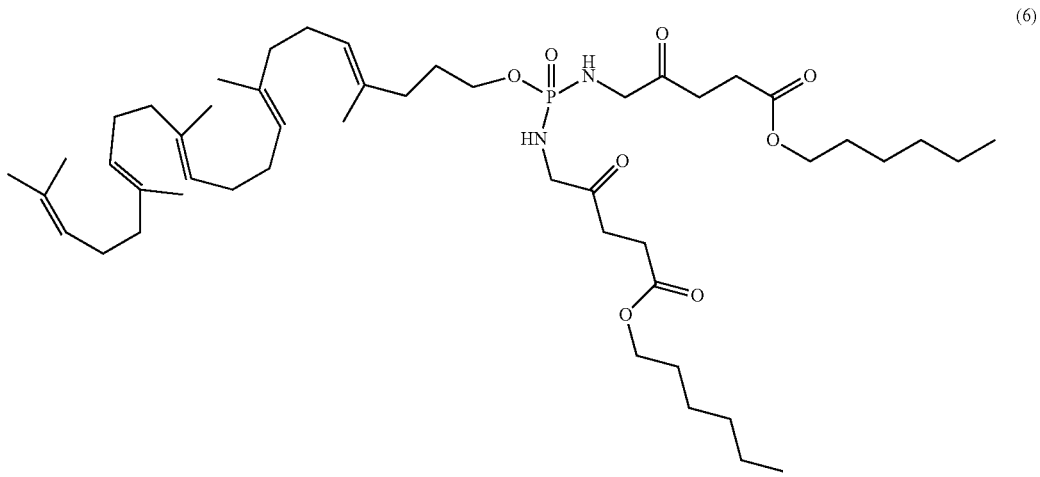 [SMILES: CCCCCCOC(=O)CCC(=O)CNP(=O)(NCC(=O)CCC(=O)OCCCCCC)OCCC/C(C)=C/CC/C(C)=C/CC/C=C(\C)CC/C=C(\C)CCC=C(C)C]

(6)

Phosphoryl trichloride (Acros) (56 mg, 0.36 mmol) was dissolved in dioxane (10 mL). Squalene alcohol (synthesized as described in Ceruti et al., 1987, *Eur. J. Med. Chem.* 22, 199-208) (140 mg, 0.36 mmol) followed by dry triethylamine (50 μL, 0.36 mmol) were added and the resulting suspension stirred at ambient temperature. After 6 h, hexyl 5-amino-4-oxopentanoate (synthesized as described in Dabrowski et al., 2003, supra) (250 mg, 1.00 mmol) was added followed by drop-wise addition of dry triethylamine (300 μL, 2.16 mmol) for 15 min. After additional 12h at room temperature the solvents were evaporated after 1 h and the crude product purified by flash chromatography using DCM/MeOH+1% TEA gradient giving colourless oil (115 mg, 37.1% yield). $^1$H NMR (300 MHz, CDCl$_3$) δ 5.17-5.01 (m, 5H), 4.09-3.85 (m, 10H), 2.70-2.59 (m, 4H), 2.08-1.92 (m, 18H), 1.62-1.52 (m, 24H), 1.35-1.24 (m, 12H), 0.93-0.82 (m, 6H). $^{13}$C NMR (75 MHz, CDCl$_3$) δ 205.16 (d), 172.71, 172.66, 135.33, 135.25, 135.23, 135.10, 133.91, 133.68, 133.63, 131.46, 125.44, 125.40, 125.28, 125.25, 124.60, 124.51, 124.47, 65.25, 50.95, 50.76, 39.97, 39.94, 39.91, 35.72, 35.66, 35.50, 34.42, 34.37, 33.02, 31.73, 31.63, 28.97, 28.73, 28.50, 28.09, 28.06, 27.01, 26.97, 26.87, 25.93, 25.80, 25.76, 22.75, 17.91, 16.29, 16.27, 16.22, 16.13, 14.23. LRMS, ESI: m/z 862.2 [M+H]$^+$, 1724.3 [2M+H]$^+$.

Example 5

Preparation of Compounds of Formula (I) According to Formula (IB1b), wherein R$^2$, R$^3$ and R$^4$ are H and R$^1$ is Hexyl, B is B1, Z is O, X is O, X1 is X1a, m is 0, n is 1

Compound was synthesized according to Scheme 7 above as detailed below.

Compound 7: hexyl 4-oxo-5-((((phosphonooxy)methoxy)carbonyl)amino)pentanoate (PSC1-Ala-Hex)

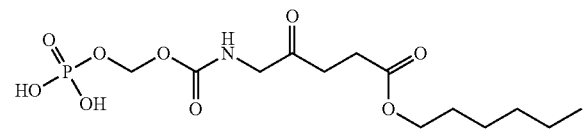

Hexyl 5-(((chloromethoxy)carbonyl)amino)-4-oxopentanoate

Hexyl 5-amino-4-oxopentanoate hydrochloride salt (251.0 mg, 1.00 mmol) was dissolved in dry DCM (20.0 mL) and cooled to −20° C. under argon atmosphere. Chloromethyl chloroformate (141.8 mg, 1.10 mmol) was added under stirring in one portion followed by dropwise addition of triethylamine (417 μL, 3.00 mmol) dissolved in dry DCM (5.0 mL). The reaction mixture was stirred for 1h at −20° C. and allowed to warm up to ambient temperature. After quenching the reaction with water (5.0 mL) the reaction mixture was extracted with DCM (2×20 mL). The organic phase was washed with diluted HCl (2×10 mL) and saturated NaHCO$_3$ solution and dried over Na$_2$SO$_4$. The product was purified by Flash chromatography using DCM/MeOH gradient giving colorless oil (272 mg, 0.886 mmol, 88.6% yield). $^1$H NMR (300 MHz, CDCl$_3$) δ 6.11 (t, J=5.3 Hz, 1H), 5.61 (s, 2H), 4.01 (d, J=5.3 Hz, 2H), 3.90 (t, J=6.8 Hz, 2H), 2.61 (t, J=6.4 Hz, 2H), 2.49 (t, J=6.4 Hz, 2H), 1.45 (q, J=6.9 Hz, 2H), 1.21-1.07 (m, 6H), 0.83-0.66 (m, 3H). $^{13}$C NMR (75 MHz, CD$_3$OD) δ 203.96, 172.67, 153.9, 70.81, 65.11, 50.49, 34.43, 31.49, 28.59, 27.89, 25.62, 22.60, 14.07. LRMS, ESI: m/z 308.4 [M+H]$^+$, 330.1 [M+Na]$^+$.

Hexyl 5-(((((bis(benzyloxy)phosphoryl)oxy)methoxy)carbonyl)amino)-4-oxopentanoate Hexyl 5-(((chloromethoxy)carbonyl)amino)-4-oxopentanoate (183 mg, 0.60 mmol) was added to a suspension of sodium iodide (440 mg, 2.93 mmol) in acetone (20.0 mL) and refluxed at 60° C. for 1h. The solvent was evaporated under reduced pressure and water (10 mL) added. The product was extracted with ether (3×20 mL) and dried over Na$_2$SO$_4$. After the solvent was evaporated colorless oil was obtained and used immediately in the next step without purification. $^1$H NMR (300 MHz, CDCl$_3$) δ 5.94 (s, 2H), 5.70 (t, J=4.6 Hz, 1H), 4.01 (d, J=5.3 Hz, 2H), 3.90 (t, J=6.8 Hz, 2H), 2.71 (t, J=6.4 Hz, 2H), 2.63 (t, J=6.4 Hz, 2H), 1.65-1.53 (m, 2H), 1.35-1.22 (m, 6H), 0.88-0.84 (m, 3H). LRMS, ESI: m/z 400.6 [M+H]$^+$, 417.1 [M+Na$_4$]$^+$, 422.1 [M+Na]$^+$.

Hexyl 5-(((iodomethoxy)carbonyl)amino)-4-oxopentanoate (40.0 mg, 0.1 mmol) was dissolved in toluene (10.0 mL) followed by the addition of silver salt of dibenzyl phosphate (50 mg, 0.13 mmol) synthesized previously according to published procedures. The suspension was stirred at ambient temperature in the dark overnight. The brown precipitate was filtered off and the solvent evaporated under reduced pressure. The crude product was purified by Flash chromatography using DCM/MeOH gradient yielding colourless oil (51 mg, 0.093 mmol, 92.9% yield). $^1$H NMR (300 MHz, CDCl$_3$) δ 7.33 (s, 10H), 5.60 (d, J=13.8 Hz, 2H), 5.06 (d, J=7.9 Hz, 4H), 4.16-3.98 (m, 4H), 2.82-2.50 (m, 4H), 1.67-1.51 (m, 2H), 1.40-1.21 (m, 6H), 0.88 (t, J=5.9 Hz, 3H). $^{13}$C NMR (75 MHz, CDCl$_3$) δ 203.23, 172.60, 154.07, 135.70, 128.77, 128.13, 83.86, 83.79, 77.67, 77.25, 76.82, 69.80, 69.73, 65.33, 50.60, 34.57, 31.61, 29.91, 28.72, 28.02, 25.74, 22.73, 14.21. LRMS, ESI: m/z 550.3 [M+H]$^+$, 567.3 [M+NH$_4$]$^+$, 572.5 [M+Na]$^+$.

Triethylammonium salt of hexyl 4-oxo-5-(((((phosphonooxy)methoxy)carbonyl)amino) pentanoate Hexyl 5-4(((((bis(benzyloxy)phosphoryl)oxy)methoxy)carbonyl)amino)-4-oxopentanoate (55.0 mg, 0.10 mmol) and triethylamine were dissolved in absolute ethanol. The reaction flask was flushed with argon before palladium on charcoal (5.0 mg) was added. Argon was exchanged with hydrogen and the reaction mixture stirred under hydrogen at 1 bar for 3 h. The catalyst was filtered off and washed with absolute ethanol (2×10 mL). The product (7) as colorless oil was obtained after evaporation of the solvent and extensive drying of the product in vacuo (38.0 mg, 0.10 mmol, 100% yield). $^1$H NMR (300 MHz, CD$_3$OD) δ 5.49 (d, J=12.6 Hz, 2H), 4.17-3.96 (m, 4H), 3.17 (q, J=7.3 Hz, 6H), 2.75 (t, J=6.3 Hz, 2H), 2.57 (t, J=6.3 Hz, 2H), 1.61-1.58 (m, 2H), 1.45-1.17 (m, 15H), 0.99-0.81 (m, 3H). $^{13}$C NMR (75 MHz, CD$_3$OD) δ 205.49, 173.20, 156.52, 83.39, 83.33, 64.66, 49.73, 48.69, 48.41, 48.12, 47.84, 47.56, 47.27, 46.99, 46.28, 33.82, 31.43, 28.49, 27.48, 25.51, 22.44, 13.20, 7.93. LRMS, ESI: m/z 368.0 [M–H]⁻, 737.3 [2M–H]⁻, 1106.7 [3M–H]⁻.

Example 6

Preparation of Compounds of Formula (I) According to Formula (IB2g), wherein $R^4$, $R^5$ and $R^6$ are H, $R^1$ is Hexyl, $X_2$ is NH, B is B2, R is COOH, X is O, X1 is X1b, p is 1, A is phenyl Compounds were synthesized according to Scheme 11 above as detailed below.

Compound 8: (2S,3S,4S,5R,6R)-6-(((4-((((5-(hexyloxy)-2,5-dioxopentyl)carbamoyl)oxy) methyl)phenyl)carbamoyl)oxy)-3,4,5-trihydroxytetrahydro-2H-pyran-2-carboxylic acid (1GLU-ALA-Hex)

(2S,3R,4 S,5S,6S)-6-(methoxycarbonyl)tetrahydro-2H-pyran-2,3,4,5-tetrayl tetraacetate (2S,3S,4S,5R,6R)-6-(2-methoxy-2-oxoethyl)tetrahydro-2H-pyran-2,3,4,5-tetrayl tetraacetate 17.6 g (0.1 mol) of β-glucuronolactone was dissolved in MeOH (100 mL) containing 0.15 g (2.77 mmol) of sodium methylate. The suspension was stirred for 1 h at ambient temperature finally turning into brownish syrup. Acetic acid anhydride (70 mL, 0.74 mol) and perchloric acid (0.3 mL, 5.0 mmol) were added slowly and the reaction mixture stirred at ambient temperature. After 4 h methanol (100 mL) and ether/petrolether (300 mL) were added and the filtrate was suction-filtered off. After drying in vacuo colorless product was obtained (20.5 g, 54.5% yield). LRMS, ESI: m/z 394.0 [M+NH₄]⁺.

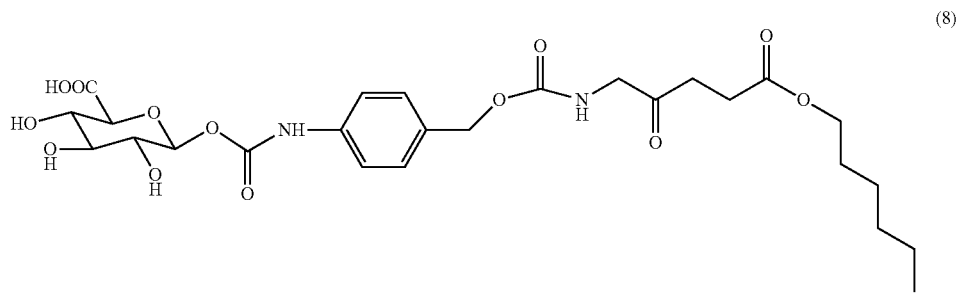 [SMILES: CCCCCCOC(=O)CCC(=O)CNC(=O)OCc1ccc(NC(=O)OC2OC(C(=O)O)C(O)C(O)C2O)cc1]

(8)

Example 7

Preparation of Compounds of Formula (I) According to Formula (IB2d), Wherein $R^5$ is $NO_2$, $R^1$, $R^4$ and $R^6$ are H, R is COOH, X1 is X1b, X is O, n is 1, p is 0, A is Nitrophenyl Compounds were synthesized according to Scheme 10 above as detailed below.

Compound 9: (2S,3S,4S,5R,6R)-6-(4-((((4-carboxy-2-oxobutyl)carbamoyl)oxy)methyl)-2-nitrophenoxy)-3,4,5-trihydroxytetrahydro-2H-pyran-2-carboxylic acid

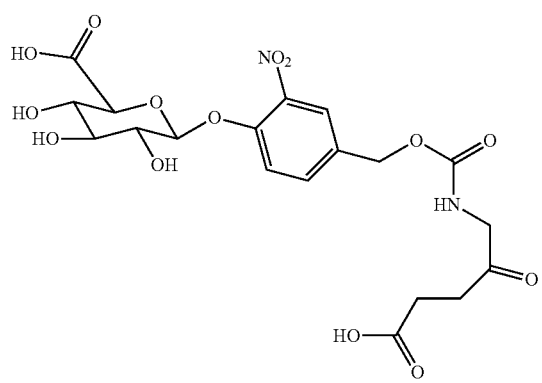

(9)

(2S,3S,4S,5R,6R)-2-(4-formyl-2-nitrophenoxy)-6-(2-methoxy-2-oxoethyl)tetrahydro-2H-pyran-3,4,5-triyl triacetate (2S,3S,4S,5R,6R)-6-(2-methoxy-2-oxoethyl)tetrahydro-2H-pyran-2,3,4,5-tetrayl tetraacetate (1.0 g, 2.66 mmol) was dissolved in dry dichloromethane (30 mL) and titanium tetrabromide (1.17, 3.19 mmol) was added dropwise. After 24h under stirring at ambient temperature the reaction mixture was diluted with dichloromethane (70 mL) and washed with water (3×20 mL) and saturated solution of sodium hydrogencarbonate (20 mL). The organic phase was dried with sodium sulfate and the solvent evaporated in vacuo yielding yellow oil.

The crude product was dissolved in dry acetonitrile (100 mL). Silver oxide (712 mg, 3.08 mmol) and 3-nitro-4-hydroxybenzaldehyde (400 mg, 2.40 mmol) were added and the resulting yellow-green suspension stirred at ambient temperature. After 4h the reaction was stopped and the solvent evaporated. The crude product was purified by Flash chromatography using hexane/ethyl acetate as mobile phase. Colourless oil which slowly crystallized was obtained (565 mg, 44.0%). LRMS, ESI: m/z 500.8 [M+NH₄]⁺

(2S,3S,4S,5R,6R)-2-(4-(hydroxymethyl)-2-nitrophenoxy)-6-(2-methoxy-2-oxoethyl) tetrahydro-2H-pyran-3,4,5-triyl triacetate (2 S,3S,4S,5R,6R)-2-(4-formyl-2-nitrophenoxy)-6-(2-methoxy-2-oxoethyl)tetrahydro-2H-pyran-3,4,5-triyl triacetate (500 mg, 1.03 mmol) was dissolved in dichloromethane (20 mL) and methanol (20 mL) and cooled to 0° C. on ice-bath. Sodium borohydride (65 mg, 1.50 mmol) was added and stirred. After 30 min TLC indicated complete conversion and saturated solution of ammonium sulphate (40 mL) was added to quench the reaction. The product was extracted with dichloromethane (3×30 mL), the organic phase dried with sodium sulphate. After solvent evaporation colourless solid was obtained which was purified by Flash chromatography using dichloromethane/methanol gradient yielding colourless product (360 mg, 74.2 mmol, 72.0%). $^1$H NMR (300 MHz, Acetonitrile-d3) δ 7.77 (d, J=2.0 Hz, 1H), 7.56 (dd, J=8.6, 2.1 Hz, 1H), 7.40 (d, J=8.6 Hz, 1H), 5.51-5.35 (m, 2H), 5.33-5.16 (m, 2H), 4.59 (s, 2H), 4.42 (d, J=9.7 Hz, 1H), 3.69 (s, 3H), 2.05 (s, 3H), 2.04 (s, 3H), 2.02 (s, 3H). $^{13}$C NMR (75 MHz, CD$_3$CN) δ 170.03, 169.89, 169.44, 167.30, 147.88, 140.97, 138.49, 132.19, 122.89, 118.46, 117.62, 99.29, 72.10, 71.14, 70.33, 69.04, 62.29, 52.75, 20.11, 20.07, 20.03. LRMS, ESI: m/z 502.7 [M+Na$_4$]$^+$.

5-((((3-nitro-4-(((2S,SR,4S,5R,6R)-3,4,5-triacetoxy-6-(2-methoxy-2-oxoethyl)tetrahydro-2H-pyran-2-yl)oxy)benzyl)oxy)carbonyl)amino)-4-oxopentanoic acid (2S,3S,4S,5R,6R)-2-(4-(hydroxymethyl)-2-nitrophenoxy)-6-(2-methoxy-2-oxoethyl) tetrahydro-2H-pyran-3,4,5-triyl triacetate (20.1 mg, 41.2 µmol) was dissolved in a mixture of DMF (1.0 mL) and acetonitrile (3.0 mL) containing triethylamine (11.4 µL). The reaction mixture was cooled to 0° C. and disuccinimidyl carbonate (15.8 mg, 61.8 µmol) was added. After 1 h 5-aminolevulinic acid hydrochloride (13.8 mg, 82.4 µmol) was added followed immediately by triethylamine (11.4 µL). The solvents were evaporated after 2h and the product extracted with dichloromethane from the water phase acidified to pH=5.0 with diluted HCl. The organic phase was washed with brine (5 mL) and dried over sodium sulphate. Crude product was purified by flash chromatography using dichloromethane methanol gradient giving colorless product (22.0 mg, 34.2 µmol). $^1$H NMR (300 MHz, CDCl$_3$) δ 7.99 (s, 1H), 7.78 (dd, J=4.2, 2.2 Hz, 1H), 7.59-7.45 (m, 1H), 7.34 (d, J=8.5 Hz, 1H), 5.64 (t, J=4.6 Hz, 1H), 5.45-5.14 (m, 5H), 5.07 (s, 2H), 4.69 (s, 2H), 4.24 (m, 2H), 4.11 (d, J=4.9 Hz, 2H), 3.72 (s, 3H), 2.68-2.65 (m, 4H), 2.10 (s, 3H), 2.04 (s, 3H), 2.03 (s, 3H). LRMS, ESI: m/z 641.2 [M−H]$^-$.

(2S,3S,4S,5R,6S)-6-(4-((((4-carboxy-2-oxobutyl)carbamoyl)oxy)methyl)-2-nitrophenoxy)-3,4,5-trihydroxytetrahydro-2H-pyran-2-carboxylic acid 5-((((3-nitro-4-(((2S,SR,4S,5R,6R)-3,4,5-triacetoxy-6-(2-methoxy-2-oxoethyl)tetrahydro-2H-pyran-2-yl)oxy)benzyl)oxy)carbonyl)amino)-4-oxopentanoic acid (10.0 mg, 15.6 µmol) was dissolved in a mixture MeOH (5.0 mL) and 1M sodium hydroxide (5.0 mL) and stirred overnight at ambient temperature. The reaction mixture was neutralized by acetic acid and purified by reverse-phase HPLC using a H$_2$O (0.0025% TFA) and acetonitrile (0.0025%) gradient. The fractions containing the product (9) were freeze-dried yielding a colourless product (6.5 mg, 12.9 µmol, 83.3%).

Example 8

Chemical Stability of Compounds of the Invention as Compared to ALA-Hex

Chemical stability was investigated for compounds of the invention as compared to the known ester ALA-Hex as follows: Chemical stability was assayed at three different pH value by dissolving the compound of interest (or ALA-Hex control) in an appropriate buffer (pH=4.00 acetate buffer; pH=7.40 phosphate buffer; and pH 8.90 borate buffer). The buffer concentration was 20 mM. The solution was kept at 37° C. and assayed at different time points. Quantification of the starting material and degradation products was performed by UPLC using the Thermo Scientific Accela UPLC-MS system. The column used was Macherey-Nagel Nucleodur C18 Gravity 50/2 1.8 µm. 10 µL aliquots were injected and eluted using 10% acetonitrile and 90% ammonium formate buffer (10 mM) isocratic elution. The column was kept at 40° C. and the flow rate was 0.4 mL/min. The quantification was performed by integrating AUCs of the chromatograms of the peaks of interest at 220 nm.

Comparative stability data are presented in FIG. 1 for compound 1 (A) and for compound 7 (B) as compared to the known ester ALA-hex (C) at 5 mM, 37° C. Those data support an increased chemical stability of compounds of the invention around physiological pH as compared to ALA-Hex. The increased stability is a consequence of derivatization at the amino group of the compounds of the invention.

Example 9

In Vitro Enzymatic Activation

The ability of compounds of the invention to release ALA in presence of a phosphatase was investigated as follows: In vitro activation of compounds of interest by alkaline phosphatase was assayed by dissolving the compound of the invention (or ALA-Hex control) in 20 mM borate buffer at pH 8.90 containing 0.5 mM magnesium chloride and 1 U to 100 U of alkaline phosphatase from calf intestine (Applichem). The solution was kept at 37° C. and assayed at different time points. Quantification of the starting material and degradation products was performed by UPLC using the Thermo Scientific Accela UPLC-MS system. The column used was Macherey-Nagel Nucleodur C18 Gravity 50/2 1.8 µm. 10 µL aliquots were injected and eluted using appropriate acetonitrile and ammonium formate buffer (10 mM) ratio with isocratic elution according to the compound of invention. The quantification was performed by integrating AUCs of the chromatograms of the peaks of interest at 220 nm.

Figure 2:
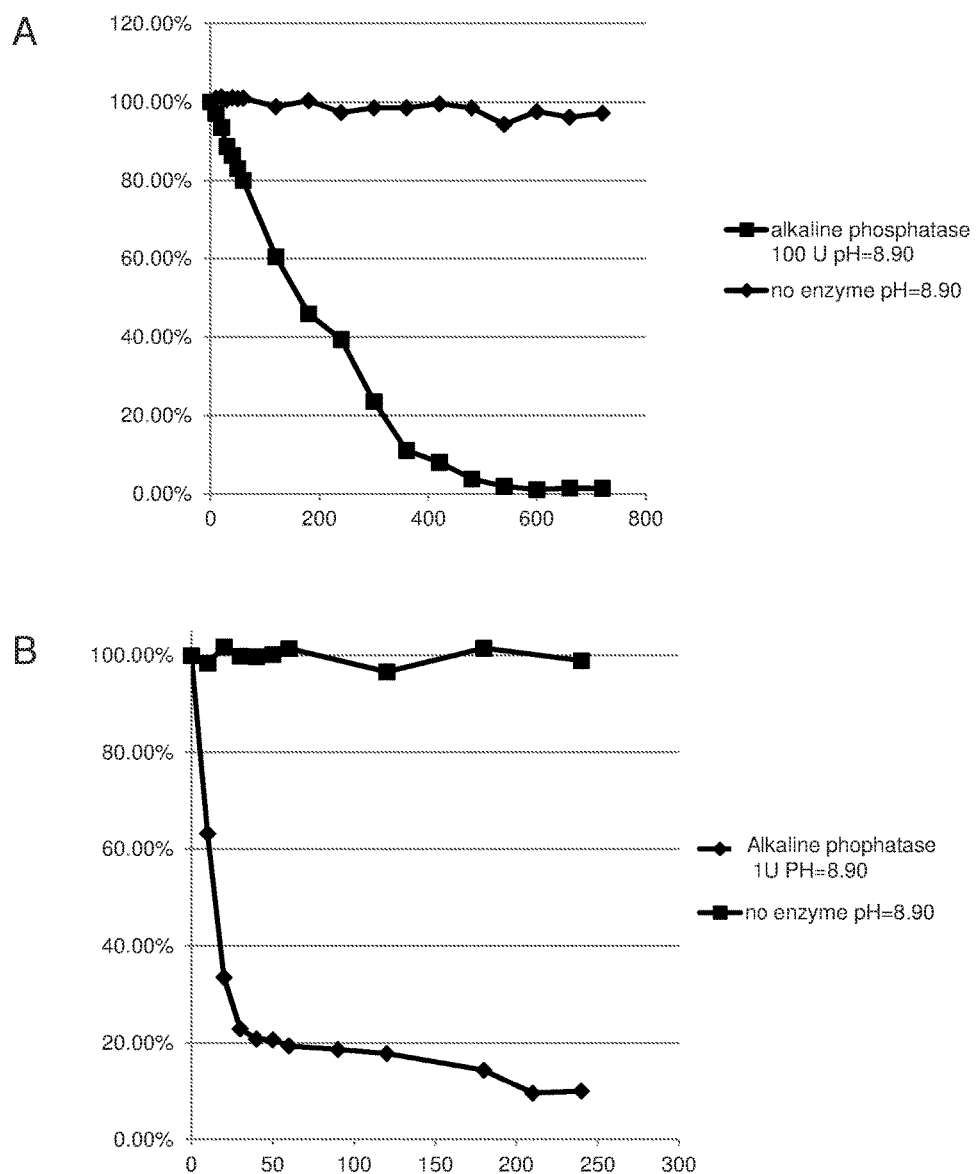
FIG. 2 represents the in vitro enzymatic activation of compounds of the invention in presence of a phosphatase as described in Example 8 as measured by % of compound remaining in solution versus time (in min). A: compound 1; B: compound 7.
Figure 3:
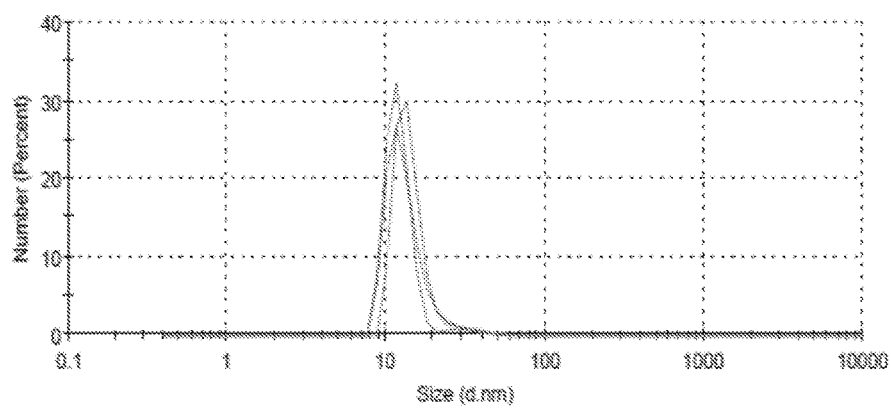
FIG. 3 represents the size distribution of the particles formed by the compounds of the invention (in %) versus the size of the diameter measured by DLS as described in Example 11. A: compound 4; B: compound 6.
Figure 3:
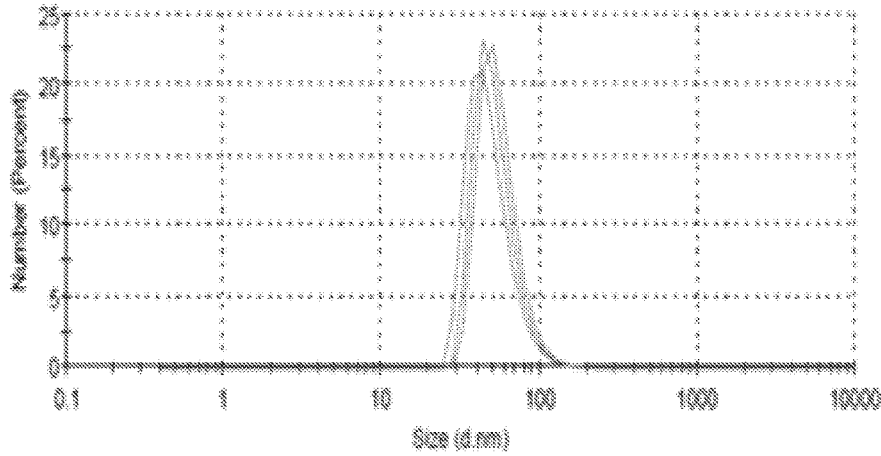

In-vitro enzymatic activation data are presented in FIG. 2 for compound 1 (A) and for compound 7 (B). Those data support the ability of compounds of the invention releasing ALA upon activation of a phosphatase under physiological conditions. The release from compound 7 is slower than the one from compound 1.

Example 10

Cell Viability and Porphyrin Accumulation in Cancer Cells (T24, A549, PC-3 and U-87)

Human bladder carcinoma cell line T24 (ATTC® HTB-4TM), human lung adenocarcinoma cell line A549 (ATTC® CCL-185TM), human prostate cancer cell line PC-3 (ATTC® CRL-1435TM), and human glioblastoma cell line U-87Mg (ATTC® HTB-14TM) were grown as monolayers and maintained in DMEM$^+$GlutaMAX™-I medium, F12K nutrient mix, and MEM, respectively. Culture media was supplemented with 10% fetal calf serum (FCS) and 100 µl/ml streptomycin and 100 IU/ml penicillin. Cells were cultivated at 37° C. in humidified 95% air and 5% CO$_2$ atmosphere and routinely maintained by serial passage in a new medium every 2-5 days, depending on the cell type.

Cell viability was measured using an MTT assay. T24 (5000 cells/well), PC3 (12000 cells/well), A549 (10000 cells/well) and U87Mg (10000 cells/well) were seeded in a 96-well plate and grown 12 to 18 hours. Then, the medium was replaced with medium containing increasing concentrations of different compounds of the invention (from 0.1 to 3.3 mM) and PPIX fluorescence was recorded with a plate reader (Safire, Tecan, Switzerland) at different time points (1, 2, 4, 6, 8 and 24 h). Excitation wavelength was set at 405 nm and emission wavelength at 630 nm. After 24 hours of incubation with different products, the cells were washed twice with DPBS and fresh medium was put into each well. They were then either irradiated with a light dose of 10 J/cm$^2$ or kept in the dark. After background subtraction, porphyrin accumulation was calculated according to the fluorescence intensity at 635 nm.

Fluorescence Kinetics Upon Incubation with Compounds of the Invention Show the Ability of Compounds of the Invention Induce Comparable Porphyrin Synthesis to the One Induced by Ala-Hex in all the Tested Cancer Cells a) PC3 Cell Line Comparative kinetic data for compound 1 (A) and for compound 7 (B) as compared to the known ester ALA-hex at 1 mM supporting comparable porphyrin synthesis capability than Ala-Hex. Further, concentration effects show that the concentration for optimal (highest) porphyrin formation is obtained at concentration 3.3 mM for compound 1 and at concentration 0.33 mM for compound 7.

b) A549 Cell Line

Similar results were obtained in these cell lines for compounds 1 and 7 with concentration for optimal (highest) porphyrin formation is obtained at concentration 0.33 for compound 7 and 3.3 mM for compound 1.

c) U87-MG Cell Line

Similar results were obtained in these cell lines for compounds 1 and 7 with concentration for optimal (highest) porphyrin formation is obtained at concentration 0.1 mM for compound 7 and 1.0 mM for compound 1.

d) T24 Cell Line

Similar results were obtained in these cell lines for compounds 1 and 7 with concentration for optimal (highest) porphyrin formation is obtained at concentration 0.1 mM for compound 7 and 3.3 mM for compound 1.

Phototoxicity Experiments

Cell viability assays were performed 24 hours upon PDT treatment. Cells were first washed with 100 µl DPBS and then 50 µl of MTT (0.650 mg/ml) in complete medium was added into each well. Four hours later, produced formazan crystals were dissolved by adding 100 µl of DMSO. The absorption was measured at 470 nm with a plate reader (Safire, Tecan, Switzerland). The percentage of cell survival was calculated with respect to control samples treated with either complete medium or a solution of DMSO (50%) in complete medium, as follows:

[$A$ (test-conc.)-$A$ (100% dead)/$A$ (100% viable)-$A$ (100% dead)]*100.

Mean values from five wells were determined and expressed as +/−S.D.

Example 11

Preparation of Nanoassembly with Compounds of the Invention Containing a Lipidic Moiety The ability of compounds of the invention when containing a lipidic moiety (as R$^2$ and/or R$^3$) of forming nanoassemblies was tested as follows:

1 mg of compound 4 or compound 6 was dissolved in ethanol (300 µL). This solution was slowly added dropwise using a microsyringe to MilliQ water (1.2 mL) under magnetic stirring (500 RPM). Nanoassemblies formed spontaneously. The organic solvent was evaporated under reduced pressure (100 mbar) at 40° C. yielding the final solution of nanomicelles of 1 mg/mL which were analysed by Dynamic Light scattering (DLS) using Zetasizer Nano ZS machine (Malvern) and stored at ambient temperature. Dynamic Light scattering (DLS) results are presented under FIG. 4 for compound 4 (A) and for compound 6 (B) and show a high homogeneity in size of the particular population with an average diameter of about 73 nm for compound 4 and 98.5 nm for compound 6.

Altogether those data support that this sub-class of compounds of the invention are advantageously able to form stable nanoparticles that would be highly suitable for administration, in particular via injection route.

Example 12

In Vivo Xenographs Models

Tumour Model. RTI 12 cells were grown in culture medium as for the in vitro studies. Once confluent they were washed with IX phosphate buffered saline and trypsinized with 0.05% Trypsin-EDTA (Gibco). The cells were then re-suspended in IX Hanks balanced salt solution. Male Balb/c nude mice, 6-8 weeks old, about 20-25 g were obtained from Animal Resource Centre of Australia. The trypsinized cells (1.5×IQ6) were implanted subcutaneously into the flanks of the nude mice. The mice were housed in micro-isolator cages (5 per cage) fed with filtered air through air vents. Their food, water and bedding were sterilized. The tumour was allowed to grow over the next 7-10 days to a size of 5-8 mm in diameter.

Six groups of balb/c nude 6 mice were used. Group I was used for the intravenous administration of ALA. Group 2 was used for intravenous administration of compound 1. Group 3 was used for intravenous administration of compound 7. Group 4 was used for intravenous administration of particles of compound 4. Group 5 was used for of particles of compound 6. Finally group was used as control for intravenous administration of saline. The nude mice were anaesthetized with a cocktail of Hypnorm (0.3 I5 mg/fentanyl citrate and 10 mg/ml flaunisone, Janssen), Dormic (5 mg/ml midazolam HCl, David Bull Laboratories) and deionised water (I:I:2). The skin overlaying the tumour was carefully removed to expose the tumour. Extreme care was taken to minimize bleeding as this can interfere with the imaging procedure. A white light image of the tumour was obtained using the Karl Storz fluorescence endoscopy system (FES). This is to help later in identifying the tumour and its margins when comparing with the fluorescence image. The tumour was imaged at different time points by the FES using filtered blue light at 460 nm.

Intravenous Administration. Compounds of the invention were dissolved in deionized water and the pH was adjusted to 7.4. The mice were administered with a dose of 250 mg/kg-body weight by tail vein injections. Five animals were used for each time point. They were then kept in darkness. The mice were imaged at various time points, such as 1, 3, 6 h and 24h. The skin overlaying the tumour was removed and the tumours were imaged using the FES. The mice were then sacrificed, the tumours were removed and snap frozen in liquid nitrogen and stored at −80° C. for further analysis.

Instrumentation. The system consists of a fluorescence detection unit, an illumination console, a video displaying and recording unit, and a computing system for image acquisition, display and processing. A 100 W xenon arc lamp (D-Light AF system, Karl Storz, Germany) is used for the white light illumination and the PpIX fluorescence excitation when filtered by a band pass filter (370-450 nm). The excitation power of the blue light at the endoscope tip is approximately 50 mW. Both of the light illumination and the observation of the tissue targeted are achieved via a modified endoscope equipped with a long pass (LP) filter (cut-off wavelength at 470 nm). The white light and ALA fluorescence imaging were achieved by a 3-chip colour CCD video camera (Tricam SL_PDD, Karl Storz, Germany) connected to the modified endoscope.

Example 13

In Vivo Chicken Acute Toxicity

5-ALA-Hex is known for its pronounced acute toxicity after intravenous injection and the $LD_{50}$ of the compounds of the invention was determined by escalating doses of compounds dissolved in milliQ™ water and pH adjusted to 7.4 administered to embryos via intravenous injection. The viability of chick embryos has been evaluated after 24h after injection. Compound 7 was better tolerated with $LD_{50}$ values of 200 μmol/kg, therefore higher than $LD_{50}$ for 5-ALA-Hex (75 μmol/kg). This higher $LD_{50}$ value is believed to be a consequence of the rapid conversion into 5-ALA-Hex. Therefore, the very high doses of Compound 1 that were tolerated by chick embryos ($LD_{50}$ of 500 μmol/kg) are consistent since this compound is much more slowly converted into 5-ALA-Hex (and 5-ALA) in all tissues expressing alkaline phosphatase.

Those data support that the compounds of the invention achieve a surprisingly reduced acute toxicity (several fold for PSI-ALA-Hex and 7-fold increase in LD50 in chick embryos for P-ALA-Hex) compared to 5-ALA-Hex.

Example 14

In Vivo CAM U87Mg Spheroid Tumor Model

Compounds of the invention were tested in vivo in using the chorioallantoic membrane (CAM) model U87-Mg tumor spheroids were obtained using a modified procedure (De Magalhaes et al., 2010, 20-26) using $2.5 \times 10^4$ cells/mL. Spheroids grew 4 days before inoculation into the CAM. On embryonic development day (EDD) 7, the hole in the eggshell was enlarged to allow access to the CAM vasculature, using a needle (25 Gauge) a hole was drilled in the CAM. A binocular lens Leica M80 (Wetzlar, Germany) was used to perform the inoculation. Once the hole was pierced in the CAM, the spheroid (approximately of 200 μm) was placed in the cavity beneath the hole. Cell medium (20 μL) was placed on the spheroid to allow the tumor to attach to the CAM membrane and develop. Then, the eggs were sealed with parafilm and returned to the incubator to let spheroids grow until EDD13. Compounds were injected intravenously into the CAM vasculature (10-40 μL), preferentially into a large blood vessels using a needle (gauge 33, 51 mm, tap N type) attached to a 100 μL syringe (Hamilton, Reno, Nev.). Fluorescence imaging of tumor nodules was done with 12-bit monochrome CDD camera (Retiga EX Q-Imaging Canada) connected to fluorescence Eclipse E600 FN microscope with a CFI achromat objective characterized by magnification 4×, numerical aperture of 0.10 and a working distance of 30 mm (Nikon, Tokyo, Japan). A conical holder was used to place the eggs during experimentation under the objective of fluorescence microscope. A mercury arc lamp HBO 103/W/2 (MS Scientific Berlin, Germany) was used to provide illumination. For the detection of PpIX a BV-2A cube (Nikon, Tokkyo, Japan) with an excitation filter: 400-440 nm, a dichroic mirror (455 nm) and an emission filter (470 nm) was used. A hollow slider filter 650/50 nm was added. Band pass filter 560/40 was used to image the autofluorescence of tumors. All pictures were taken with a 90 ms exposure and gain set at 50. Tumor imaging was performed at time 0, 30, 60 and 120 min after injection. Autofluorescence images were taken before injection. Images were processed using Openlab software version 3.1.5. Image resolution was 678×518 pixels with a binning set at 2 and the brightness and contrast for all images. Data was analysed using multiple t-tests and statistical significance determined at each time point.

Figure 4:
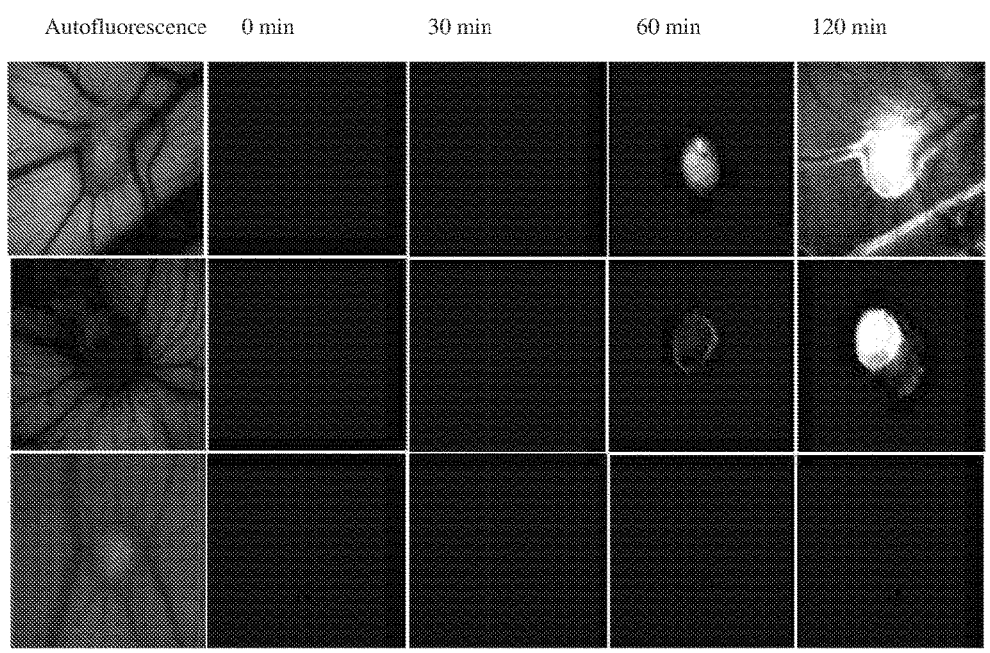
FIG. 4 shows the in vivo fluorescence of CAM U87Mg spheroid tumor as described in Example 14. Injection of non-fluorescent Compound 7 (100 μmol/kg, top), Compound 1 (300 μmol/kg, middle) and fluorescent PpIX (100 μmol/kg, bottom). Tumor auto-fluorescence images at time 0 (left) and fluorescence images at times 0, 30, 60 and 120 min.

In accordance with in vitro data, Compound 7 started to outline the tumors as early as 30 min post injection followed by an excellent and statistically significant signal to background at 1 h and also at 2h (FIG. 4). As expected, Compound 1 displayed delayed onset of the fluorescence signal but a robust contrast nevertheless. The fluorescence decreased to background levels in chick embryos in 5h which is a clinically relevant advantage. Interestingly, PpIX that was injected as one of the controls, to demonstrate that the PpIX was produced within the tumors and not in other developing tissues in the embryos, showed no preferential accumulation and fluorescence in the tumors (FIG. 4).

Altogether, those data support that compounds of the invention exhibit clearly improved chemical stability at acidic, neutral and basic pH values and structure-dependent sensitivity to alkaline phosphatase. The achieved robust production of PpIX and red fluorescence in U87Mg glioblastoma cancer cell lines is better than the state of the art fluorescence levels of ALA-Hex. Further, they present a reduced acute toxicity as compared to 5-ALA-Hex. Finally, clinically translational fluorescence profiles in CAM implanted U87Mg tumor spheroids were observed after the injection of compounds of the invention and statistically significant fluorescence was observed throughout the tumor mass within the clinically acceptable time-frame. Therefore, those compounds are believed to be particularly useful in fluorescence-guided tumor resection (FGR) and fluorescence-based detection.

The invention claimed is:
1. A 5-Aminolevulinic derivative of Formula (I) and any pharmaceutically acceptable salts thereof:

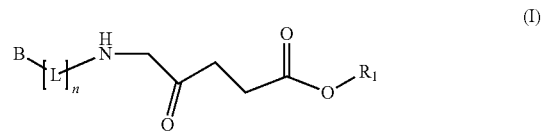

wherein B is a biocompatible non-peptidic moiety cleavable by ubiquitous enzymes present in mammalian cells, L is a biocompatible self-removable linker and $R_1$ is selected from H, optionally substituted $C_1$-$C_{30}$ alkyl, optionally substituted $C_2$-$C_{30}$ alkenyl, optionally substituted $C_2$-$C_{30}$ alkynyl, optionally substituted alkoxy, optionally substituted aryl, optionally substituted heteroaryl and optionally substituted aryl $C_1$-$C_6$ alkyl and n is an integer selected from 0 and 1, wherein said biocompatible non-peptidic moiety cleavable by ubiquitous enzymes present in mammalian cells is not an acetyl group.

2. The derivative according to claim 1 wherein n is 1.
3. The derivative according to claim 1 wherein n is 0.
4. The derivative according to claim 1 wherein the biocompatible self-removable linker L is of Formula (L):

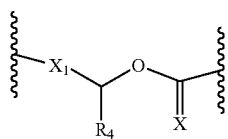

(L)

wherein $R^4$ is selected from H, optionally substituted $C_1$-$C_{30}$ alkyl (e.g. methyl), optionally substituted $C_2$-$C_{30}$ alkenyl, optionally substituted $C_2$-$C_{30}$ alkynyl, optionally substituted alkoxy, optionally substituted aryl, optionally substituted heteroaryl, optionally substituted aryl alkyl and optionally substituted aryl alkyl, X is absent or selected from O and S and $X_1$ is selected from the following groups:

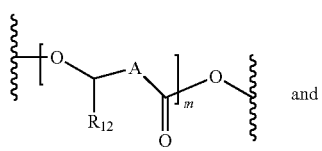

(XIa)

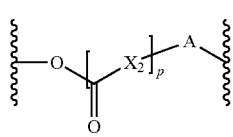

(XIb)

and wherein m is an integer selected from 0 or 1 and p is an integer selected from 0 or 1, $X_2$ is selected from O, S, NH, $R_{12}$ is selected from H, optionally substituted $C_1$-$C_{30}$ alkyl, optionally substituted $C_2$-$C_{30}$ alkenyl, optionally substituted $C_2$-$C_{30}$ alkynyl, optionally substituted alkoxy, optionally substituted aryl and optionally substituted alkyl-aryl and A is an optionally substituted aromatic ring.

5. The 5-Aminolevulinic derivative according to claim 1 wherein B is a biocompatible non-peptidic moiety cleavable by phosphatases or glycosidases.
6. The derivative according to claim 1 wherein B is a phosphate group.
7. The derivative according to claim 1 wherein B is at least one glucuronic acid group.
8. The derivative according to claim 1 wherein B is a group selected from the following groups:

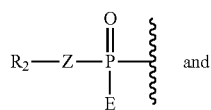

(B1)

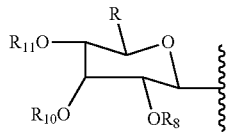

(B2)

wherein Z is selected from O and NH and E is selected from —$OR^3$ and a group D2:

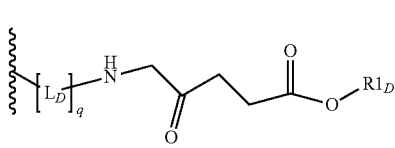

(D2)

wherein $R_2$ and $R_3$ are independently selected from H, optionally substituted $C_1$-$C_{30}$ alkyl, optionally substituted $C_2$-$C_{30}$ alkenyl, optionally substituted C2-C30 alkynyl, optionally substituted alkoxy, optionally substituted aryl, optionally substituted heteroaryl, optionally substituted $C_3$-$C_8$-cycloalkyl, optionally substituted heterocycloalkyl and a lipidic group; R1D is selected from H, optionally substituted $C_1$-$C_{30}$ alkyl, optionally substituted $C_2$-$C_{30}$ alkenyl, optionally substituted $C_2$-$C_{30}$ alkynyl, optionally substituted alkoxy, optionally substituted aryl and optionally substituted aryl $C_1$-$C_6$ alkyl and q is an integer selected from 0 and 1 and LD is a biocompatible self-removable linker, R is selected from —$COOR^9$ and —$CH_2OH$, $R^8$, $R^{10}$ and $R^{11}$ are independently selected from H, or an appropriate protective group for hydroxyl groups and $R^9$ is selected from H, optionally substituted $C_1$-$C_{30}$ alkyl, optionally substituted $C_2$-$C_{30}$ alkenyl, optionally substituted $C_2$-$C_{30}$ alkynyl, optionally substituted alkoxy, optionally substituted aryl, optionally substituted heteroaryl, optionally substituted $C_3$-$C_8$-cycloalkyl and optionally substituted heterocycloalkyl.

9. The derivative according to claim 1 wherein B is a group B1.
10. The derivative according to claim 1, wherein $R_3$ is H.
11. The derivative according to claim 1, wherein $R_2$ is an optionally substituted phenyl.
12. The derivative according to claim 1, wherein $R_2$ is a lipid group.
13. The derivative according to claim 12 wherein $R_2$ is a squalene.
14. The derivative according to claim 1, wherein B is a group B2.
15. The derivative according to claim 1 selected from:

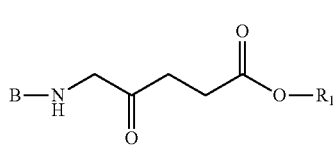

(Ia)

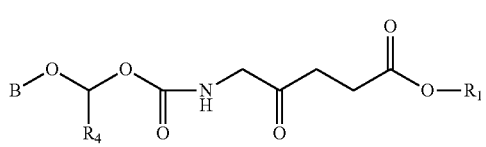

(Ib)

-continued (Ic)
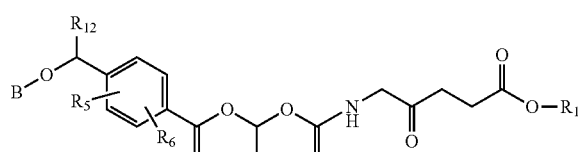

(Id)
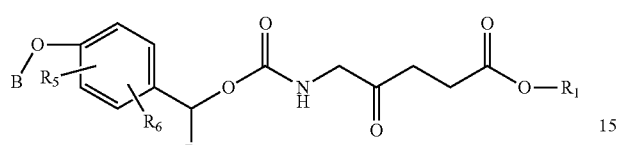

(Ie)
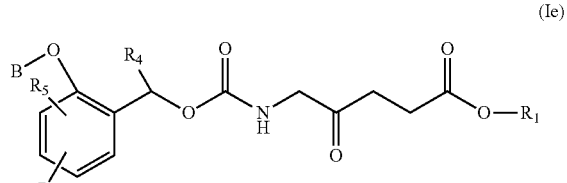

(If)
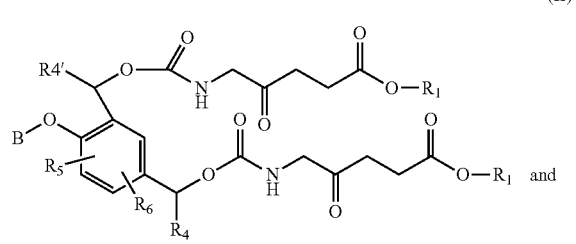

(Ig)
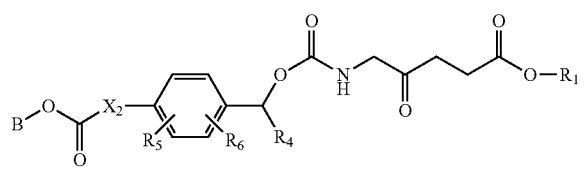

wherein:
R₁ is selected from H, optionally substituted C₁-C₃₀ alkyl, optionally substituted C₂-C₃₀ alkenyl, optionally substituted C₂-C₃₀ alkynyl, optionally substituted alkoxy, optionally substituted aryl, optionally substituted heteroaryl and optionally substituted aryl C₁-C₆ alkyl; R₂ and R₃ are independently selected from H, optionally substituted C₁-C₃₀ alkyl, optionally substituted C₂-C₃₀ alkenyl, optionally substituted C2-C30 alkynyl, optionally substituted alkoxy, optionally substituted aryl, optionally substituted heteroaryl, optionally substituted C₃-C₈-cycloalkyl, optionally substituted heterocycloalkyl and a lipidic group; R1D is selected from H, optionally substituted C₁-C₃₀ alkyl, optionally substituted C₂-C₃₀ alkenyl, optionally substituted C₂-C₃₀ alkynyl, optionally substituted alkoxy, optionally substituted aryl and optionally substituted aryl C₁-C₆ alkyl;
R₄ is selected from H, optionally substituted C₁-C₃₀ alkyl (e.g. methyl), optionally substituted C₂-C₃₀ alkenyl, optionally substituted C₂-C₃₀ alkynyl, optionally substituted alkoxy, optionally substituted aryl, optionally substituted heteroaryl, optionally substituted aryl alkyl and optionally substituted aryl alkyl;

R₁₂ is selected from H, optionally substituted C₁-C₃₀ alkyl, optionally substituted C₂-C₃₀ alkenyl, optionally substituted C₂-C₃₀ alkynyl, optionally substituted alkoxy, optionally substituted aryl and optionally substituted alkyl-aryl;
R₄' is R₄ or selected from H, optionally substituted C₁-C₃₀ alkyl, optionally substituted C₂-C₃₀ alkenyl, optionally substituted C₂-C₃₀ alkynyl, optionally substituted alkoxy, optionally substituted aryl and optionally substituted alkyl-aryl, R₅ and R₆ are independently selected from H, halogen, amino, nitro or optionally at least one group among R₅ and R₆ is a group of Formula D3:

(D3)
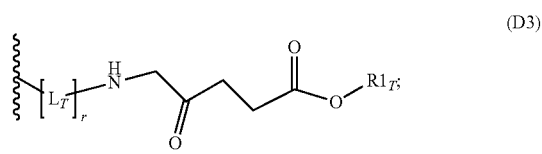

and
R1$_T$ is selected from H, optionally substituted C₁-C₃₀ alkyl, optionally substituted C₂-C₃₀ alkenyl, optionally substituted C₂-C₃₀ alkynyl, optionally substituted alkoxy, optionally substituted aryl, optionally substituted C₁-C₆ alkyl aryl and optionally substituted heteroaryl, q is an integer R1$_T$ is selected from H, optionally substituted C₁-C₃₀ alkyl, optionally substituted C₂-C₃₀ alkenyl, optionally substituted C₂-C₃₀ alkynyl, optionally substituted alkoxy, optionally substituted aryl, optionally substituted C₁-C₆ alkyl aryl and optionally substituted heteroaryl, r is an integer selected from 0 and 1 and L$_T$ is a biocompatible self-removable linker.

16. The derivative according to claim 1 selected from the group consisting of:
triethylammonium salt of hexyl 5-((hydroxy(phenoxy) phosphoryl)amino)-4-oxopentanoate;
triethylammonium salt of methyl 5-((hydroxy(phenoxy) phosphoryl) amino)-4-oxopentanoate
triethylammonium salt of benzyl 5-((hydroxy(phenoxy) phosphoryl) amino)-4-oxopentanoate;
hexyl 5-((hydroxy(((4E,8E,12E,16E)-4,8,13,17,21-pentamethyldocosa-4,8,12,16,20-pentaen-1-yl)oxy)phosphoryl)amino)-4-oxopentanoate;
Bis(hexyl) 5-((hydroxy(phenoxy)phosphoryl)bis(amino)-4-oxopentanoate);
Bis-hexyl 5-((hydroxy(((4E,8E,12E,16E)-4,8,13,17,21-pentamethyldocosa-4,8,12,16,20-pentaen-1-yl)oxy) phosphoryl)bis-amino)-4-oxopentanoate;
hexyl 4-oxo-5-((((phosphonooxy)methoxy)carbonyl) amino)pentanoate;
(2S,3S,4S,5R,6R)-6-(((4-((((5-(hexyloxy)-2,5-dioxopentyl)carbamoyl)oxy)methyl) phenyl)carbamoyl)oxy)-3,4,5-trihydroxytetrahydro-2H-pyran-2-carboxylic acid; and
(2S,3S,4S,5R,6R)-6-(4-(((((4-carboxy-2-oxobutyl)carbamoyl)oxy)methyl)-2-nitrophenoxy)-3,4,5-trihydroxytetrahydro-2H-pyran-2-carboxylic acid.

17. A pharmaceutical formulation comprising a derivative according to claim 1 or a particle thereof and at least one pharmaceutically acceptable carrier.

* * * * *

UNITED STATES PATENT AND TRADEMARK OFFICE
CERTIFICATE OF CORRECTION

PATENT NO. : 10,258,690 B2
APPLICATION NO. : 15/575025
DATED : April 16, 2019
INVENTOR(S) : Andrej Babic and Norbert Lange It is certified that error appears in the above-identified patent and that said Letters Patent is hereby corrected as shown below:

In the Specification

Column 66,
Lines 24-36, "$R1_T$ is selected from H, optionally substituted $C_1$-$C_{30}$ alkyl, optionally substituted $C_2$-$C_{30}$ alkenyl, optionally substituted $C_2$-$C_{30}$ alkynyl, optionally substituted alkoxy, optionally substituted aryl, optionally substituted $C_1$-$C_6$ alkyl aryl and optionally substituted heteroaryl, q is an integer $R1_T$ is selected from H, optionally substituted $C_1$-$C_{30}$ alkyl, optionally substituted $C_2$-$C_{30}$ alkenyl, optionally substituted $C_2$-$C_{30}$ alkynyl, optionally substituted alkoxy, optionally substituted aryl, optionally substituted $C_1$-$C_6$ alkyl aryl and optionally substituted heteroaryl, r is an integer selected from 0 and 1 and $L_T$ is a biocompatible self-removable linker." should read -- $R1_T$ is selected from H, optionally substituted $C_1$-$C_{30}$ alkyl, optionally substituted $C_2$-$C_{30}$ alkenyl, optionally substituted $C_2$-$C_{30}$ alkynyl, optionally substituted alkoxy, optionally substituted aryl, optionally substituted $C_1$-$C_6$ alkyl aryl and optionally substituted heteroaryl, r is an integer selected from 0 and 1 and $L_T$ is a biocompatible self-removable linker.--.

Signed and Sealed this
Twenty-eighth Day of January, 2020

Andrei Iancu
*Director of the United States Patent and Trademark Office*